United States Patent
Dax et al.

(10) Patent No.: US 6,380,224 B1
(45) Date of Patent: *Apr. 30, 2002

(54) AMINE AND AMIDE DERIVATIVES AS LIGANDS FOR THE NEUROPEPTIDE Y Y5 RECEPTOR USEFUL IN THE TREATMENT OF OBESITY AND OTHER DISORDERS

(75) Inventors: Scott L. Dax, Landenberg; James McNally, Souderton; Mark Youngman, Warminster, all of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/626,856

(22) Filed: Jul. 27, 2000

Related U.S. Application Data

(60) Provisional application No. 60/146,069, filed on Jul. 28, 1999.

(51) Int. Cl.[7] ............... A61K 31/44; C07D 241/04; C07D 211/70; C07D 233/61; C07D 333/20
(52) U.S. Cl. ............... 514/357; 514/396; 514/269; 514/438; 514/471; 544/392; 546/333; 548/340.1; 549/75; 549/491
(58) Field of Search ............... 514/357, 396, 514/269, 438, 471; 546/333; 548/340.1; 549/75, 491; 544/392

(56) References Cited

FOREIGN PATENT DOCUMENTS

| WO | 9719682 A | 6/1997 |
|---|---|---|
| WO | 9835957 A | 8/1998 |
| WO | 9955667 A | 11/1999 |

OTHER PUBLICATIONS

M.A. Youngman Et Al. "Alpha–substituted N–(sulfonamido) alkyl–beta–aminotetralins: potent and selective neuropeptide Y Y5 receptor antagonists" Journal of Medicinal Chemistry., vol. 43, No. 3, Feb. 2000, pp. 346–350, XP002153193, American Chemical Society, Washington., US ISSN: 0022–2623 the whole document.

*Primary Examiner*—Richard L. Raymond
*Assistant Examiner*—Tamthom N. Truong
(74) *Attorney, Agent, or Firm*—Ralph Palo

(57) ABSTRACT

Amine and amide derivatives of the formula:

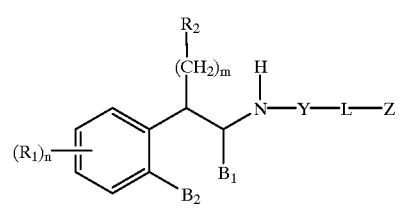

which are ligands for the neuropeptide Y Y5 (NPY5) receptor, methods of preparation and pharmaceutical compositions containing amines and amides of formula A as the active ingredient are described. The amines and amides of formula A are useful in the treatment of disorders and diseases associated with NPY receptor subtype Y5.

9 Claims, No Drawings

AMINE AND AMIDE DERIVATIVES AS LIGANDS FOR THE NEUROPEPTIDE Y Y5 RECEPTOR USEFUL IN THE TREATMENT OF OBESITY AND OTHER DISORDERS

This application claims the benefit of Provisional Application No. 60/146,069 filed Jul. 28, 1999.

FIELD OF THE INVENTION

This invention relates to a series of amine and amide derivatives, pharmaceutical compositions containing them and intermediates used in their preparation. The compounds of the invention are ligands for the neuropeptide Y Y5 (NPY5) receptor, a receptor which is associated with a number of central nervous system disorders and affective conditions. In addition, many of the compounds of the invention reduce food consumption in a rodent model of feeding.

BACKGROUND OF THE INVENTION

Regulation and function of the mammalian central nervous system is governed by a series of interdependent receptors, neurons, neurotransmitters, and proteins. The neurons play a vital role in this system, for when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to humans, neuropeptides have been discovered in a number of animal species. In some instances the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein which is enzymatically processed to yield the active substance. Based upon these differences, compared to small molecule neurotransmitters, neuropeptide-based strategies may offer novel therapies for CNS diseases and disorders. Specifically, agents that affect the binding of neuropeptides to their respective receptors or ameliorate responses that are mediated by neuropeptides are potential therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders and diseases have been treated with small molecules and peptides which modulate neuronal responses to endogenous neurotransmitters.

One example of the class of neuropeptides is neuropeptide Y (NPY). NPY was first isolated from porcine brain (Tatemoto, K. et al. Nature 1982, 296, 659) and was shown to be structurally similar to other members of the pancreatic polypeptide (PP) family such as peptide YY, which is primarily synthesized by endocrine cells in the gut, and pancreatic polypeptide, which is synthesized by the pancreas. Neuropeptide Y is a single peptide protein that consists of thirty-six amino acids containing an amidated C-terminus. Like other members of the pancreatic polypeptide family, NPY has a distinctive conformation that consists of an N-terminal polyproline helical region and an amphiphilic α-helix joined by a characteristic PP-fold (Vladimir, S. et. Al. Biochemistry 1990, 20, 4509). Furthermore, NPY sequences from a number of animal species have been elucidated and all show a high degree of amino acid homology to the human protein (>94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Six different receptor subtypes [Y1, Y2, Y3, Y4(PP), Y5, Y6 (formerly designated as a Y5 receptor)] are recognized today based upon binding profile, pharmacology and/or composition if identity is known (Wahlestedt, C. et. al. Ann. NY Acad. Sci. 1990, 611, 7; Larhammar, D. et. al. J. Biol. Chem. 1992, 267, 10935; Wahlestedt, C. et. al. Regul. Pept. 1986, 13, 307; Fuhlendorff, J. U. et. al. Proc. Natl. Acad. Sci. USA 1990, 87, 182; Grundemar, L. et. al. J. Pharmacol. Exp. Ther. 1991, 258, 633; Laburthe, M. et. al. Endocrinology 1986, 118, 1910; Castan, I. et. al. Endocrinology 1992, 131, 1970; Gerald, C. et. al. Nature 1996, 382, 168; Weinberg, D. H. et. al. Journal of Biological Chemistry 1996, 271, 16435; Gehlert, D. et. al. Current Pharmaceutical Design 1995, 1, 295; Lundberg, J. M. et. al. Trends in Pharmaceutical Sciences 1996, 17, 301). Most and perhaps all NPY receptor proteins belong to the family of so-called G-protein coupled receptors (GPCRs). The neuropeptide Y5 receptor, a putative GPCR, is negatively coupled to cellular cyclic adenosine monophosphate (cAMP) levels via the action of adenylate cyclase (Gerald, C. et. al. Nature 1996, 382, 168; Gerald, C. et. al. PCT WO 96/16542). For example, NPY inhibits forskolin-stimulated cAMP production/levels in a neuroblastoma cell line. A Y5 ligand that mimics NPY in this fashion is an agonist whereas one that competitively reverses the NPY inhibition of forskolin-stimulated cAMP production is an antagonist.

Neuropeptide Y itself is the archetypal substrate for the NPY receptors and its binding can elicit a variety of pharmacological and biological effects in vitro and in vivo. When administered to the brain of live animals (intracerebroventricularly (icv) or into the amygdala), NPY produces anxiolytic effects in established animal models of anxiety such as the elevated plus-maze, Vogel punished drinking and Geller-Seifter's bar-pressing conflict paradigms (Heilig, M. et. al. Psychopharmacology 1989, 98, 524; Heilig, M. et. al. Reg. Peptides 1992, 41, 61; Heilig, M. et. al. Neuropsycho-pharmacology 1993, 8, 357). Thus compounds that mimic NPY are postulated to be useful for the treatment of anxiolytic disorders.

The immunoreactivity of neuropeptide Y is notably decreased in the cerebrospinal fluid of patients with major depression and those of suicide victims (Widdowson, P. S. et. al. Journal of Neurochemistry 1992, 59, 73), and rats treated with tricyclic antidepressants display significant increases of NPY relative to a control group (Heilig, M. et.

al. *European Journal of Pharmacology* 1988, 147, 465). These findings suggest that an inadequate NPY response may play a role in some depressive illnesses, and that compounds that regulate the NPY-ergic system may be useful for the treatment of depression.

Neurdpeptide Y improves memory and performance scores in animal models of learning (Flood, J. F. et. al. *Brain Research* 1987, 421, 280) and therefore may serve as a cognition enhancer for the treatment of neurodegenerative diseases such as Alzheimer's Disease (AD) as well as AIDS-related and senile dementia.

Elevated plasma levels of NPY are present in animals and humans experiencing episodes of high sympathetic nerve activity such as surgery, newborn delivery and hemorrhage (Morris, M. J. et. al. *Journal of Autonomic Nervous System* 1986, 17, 143). Thus chemical substances that alter the NPY-ergic system may be useful for alleviating migraine, pain and the condition of stress.

Neuropeptide Y also mediates endocrine functions such as the release of luteinizing hormone (LH) in rodents (Kalra, S. P. et. al. *Frontiers in Neuroendrocrinology* 1992, 13, 1). Since LH is vital for mammalian ovulation, a compound that mimics the action of NPY could be useful for the treatment of infertility, particularly in women with so-called luteal phase defects.

Neuropeptide Y is a powerful stimulant of food intake; as little as one-billionth of a gram, when injected directly into the CNS, causes satiated rats to overeat (Clark, J. T. et. al. *Endocrinology* 1984, 115, 427; Levine, A. S. et. al. *Peptides* 1984, 5, 1025; Stanley, B. G. et. al. *Life Sci.* 1984, 35, 2635; Stanley, B. G. et. al. *Proc. Nat. Acad. Sci. USA* 1985, 82, 3940). Thus NPY is orexigenic in rodents but not anxiogenic when given intracerebroventricularly and so antagonism of neuropeptide receptors may be useful for the treatment of diabetes and eating disorders such as obesity, anorexia nervosa and bulimia nervosa.

In recent years, a variety of potent, structurally distinct small molecule Y1 antagonists has been discovered and developed (Hipskind, P. A. et. al. *Annu. Rep. Med. Chem.* 1996, 31, 1–10; Rudolf, K. et. al. *Eur. J. Pharmacol.* 1994, 271, R11; Serradeil-Le Gal, C. et. al. *FEBS Lett.* 1995, 362, 192; Wright, J. et. al. *Bioorg. Med. Chem. Lett.* 1996, 6, 1809; Poindexter, G. S. et. al. U.S. Pat. No. 5,668,151; Peterson, J. M. et. al. WO9614307 (1996)). However, despite claims of activity in rodent models of feeding, it is unclear if inhibition of a feeding response can be attributed to antagonism of the Y1 receptor.

Several landmark studies strongly suggest that an "atypical Y1" receptor and/or the Y5 receptor, rather than the classic Y1 receptor, is responsible for invoking NPY-stimulated food consumption in animals. It has been shown that the NPY fragment NPY2-36 is a potent inducer of feeding despite poor binding at the classic Y1 receptor (Stanley, B. G. et. al. *Peptides* 1992, 13, 581). Conversely, a potent and selective Y1 agonist has been reported to be inactive at stimulating feeding in animals (Kirby, D. A. et. al. *J. Med. Chem.* 1995, 38, 4579). More pertinent to the invention described herein, [D-Trp$^{32}$]NPY, a selective Y5 receptor activator has been reported to stimulate food intake when injected into the hypothalamus of rats (Gerald, C. et. al. *Nature* 1996, 382, 168). Since [D-Trp$^{32}$]NPY appears to be a full agonist of the Y5 receptor with no appreciable Y1 activity, the Y5 receptor is hypothesized to be responsible for the feeding response. Accordingly compounds that antagonize the Y5 receptor should be effective in inhibiting food intake, particularly that stimulated by NPY.

A variety of structurally diverse compounds that antagonize the Y5 receptor have been described in various publications. In PCT WO 97/19682, aryl sulfonamides and sulfamides derived from arylalkylamines are described as Y5 antagonists and are reported to reduce food consumption in animals. In PCT WO 97/20820, PCT WO 97/20822 and PCT WO 97/20823, sulfonamides containing heterocyclic systems such as quinazolin-2,4-diazirines, are likewise claimed as Y5 antagonists and reported to reduce feeding. In PCT WO 99/10330, a series of heterocyclic ketones is claimed to be NPY Y5 antagonists. In PCT WO 99/01128, certain diarylimidazole derivatives are claimed as a new class of NPY specific ligands. In PCT WO 98/35944, a series of α-alkoxy and α-thioalkoxyamides are claimed to be NPY Y5 receptor antagonists. In PCT WO 98/35957, a series of amide derivatives are claimed as selective neuropeptide Y receptor antagonists; however, these compounds are structurally different from the compounds of this invention. The amides and amines of this invention that are described herein are novel molecular entities that may have binding motifs that are different from these and other Y5 ligands that have been disclosed in patent applications or publications.

SUMMARY OF THE INVENTION

The present invention is related to compounds of formula A

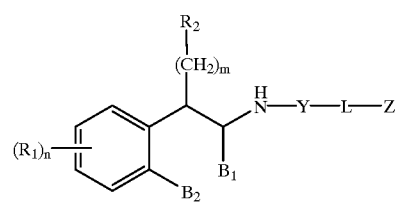

$R_1$ is independently selected from the group consisting of hydrogen; hydroxy; halo; $C_{1-8}$alkyl; substituted $C_{1-8}$ alkyl wherein the substituent is selected from halo, such as chloro, bromo, fluoro and iodo; $C_{1-8}$alkoxy; substituted $C_{1-8}$ alkoxy wherein the substituent is selected from halo, such as chloro, bromo, fluoro and iodo; trifluoroalkyl; $C_{1-8}$ alkylthio and substituted $C_{1-8}$alkylthio wherein the substituent is selected from halo, such as chloro, bromo, fluoro and iodo, trifluoro$C_{1-8}$alkyl and $C_{1-8}$alkoxy; $C_{3-6}$cycloalkyl; $C_{3-8}$cycloalkoxy; nitro; amino; $C_{1-6}$alkylamino; $C_{1-8}$dialkylamino; $C_{4-8}$cycloalkylamino; cyano; carboxy; $C_{1-5}$alkoxycarbonyl; $C_{1-5}$alkylcarbonyloxy; formyl; carbamoyl; phenyl and substituted phenyl wherein the substituent is selected from halo, hydroxyl, nitro, amino and cyano;

n is 1–2

$B_1$ is hydrogen;

$B_2$ is hydrogen;

or $B_1$ and $B_2$ may be methylene and joined together form a five or six-membered ring;

m 0–3

$R_2$ is independently selected from the group consisting of hydrogen; hydroxy; $C_{1-6}$alkyl; $C_{2-6}$alkenyl; halo, such as fluoro and chloro; $C_{3-7}$cycloalkyl; phenyl; substituted phenyl wherein the substituent is selected from halo, $C_{1-6}$alkyl, $C_{1-6}$alkoxy, trifluoro$C_{1-6}$alkyl, cyano, nitro, amino, $C_{1-6}$alkylamino, and $C_{1-6}$dialkylamino; naphthyl; substituted naphthyl wherein the substituent is selected from halo, $C_{1-6}$alkyl, $C_{1-6}$alkoxy, trifluoro$C_{1-6}$alkyl, cyano, nitro, amino, $C_{1-6}$alkylamino, and $C_{1-6}$dialkylamino; phenoxy; substituted phenoxy wherein the substituent is selected from halo, $C_{1-6}$alkyl, $C_{1-6}$alkoxy, trifluoro$C_{1-6}$alkyl, cyano and nitro; a heteroaryl group such as pyridyl, pyrimidyl, furyl, thienyl, and imidazolyl; substituted heteroaryl wherein the substitutent is selected from $C_{1-6}$alkyl and halo; and heterocycloalkyl such as pyrrolidino or piperidino;

Y is methylene (—CH$_2$—) or carbonyl (C=O)

L is selected from the group consisting of
  $C_{1-8}$alkylene; $C_{2-10}$alkenylene; $C_{2-10}$alkynylene; $C_{3-7}$cycloalkylene; $C_{3-7}$cycloalkyl$C_{1-4}$alkylene; aryl$C_{1-4}$alkylene;
  α-amino$C_{4-7}$alkylene;

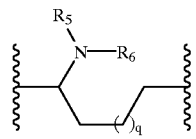

(N-methylene)piperidin-4-yl;

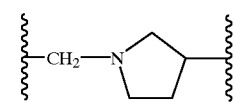

(N-methylene)piperidin-4-yl;

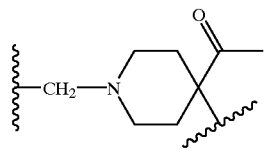

(N-methylene)pyrrolidin-3-yl;

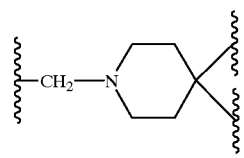

(N-methylene)-4-acetyl-piperidin-4-yl;

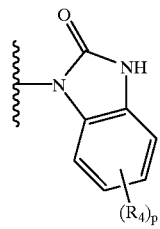

and (N-methylene)piperidin-4,4-diyl;

Z is selected from the group consisting of:
  aryl;

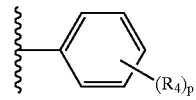

N-sulfonamido;

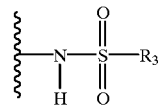

N-(aryl)sulfonamido;

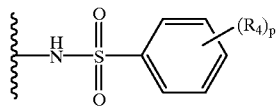

arylamido;

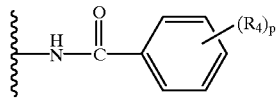

arylureido;

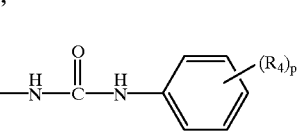

arylacetamido:

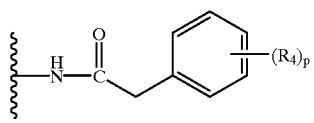

(aryloxy)carbonylamino;

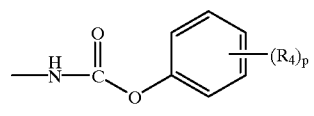

2,3-dihydro-2-oxo-1H-benzimidazol-1-yl;

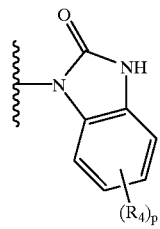

and 1-aryl-2,3-dihydro-4-oxo-imidazol-5,5-diyl;

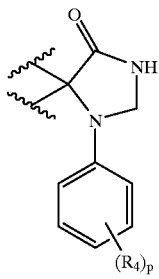

The aryl group in each case may be substituted as shown.

R$_3$ is independently selected from the group consisting of C$_1$alkyl; substituted C1alkyl wherein the substituent is selected from C,alkoxy and halo; cycloalkyl; substituted cycloalkyl wherein the substituent is selected from C1alkoxy and halo; naphthyl; substituted naphthyl wherein the substituent is selected from halo, nitro, amino and cyano; heteroaryl wherein the heteroaryl group is selected from pyridyl, pyrimidyl, furyl, thienyl and imidazolyl; and substituted heteroaryl wherein the substituent is selected from halo, nitro, amino and cyano;

R$_4$ is independently selected from the group consisting of hydrogen; C$_{1-8}$alkyl; substituted C$_{1-8}$alkyl wherein the substituent is selected from alkoxy and halo; hydroxy; halogen; cyano; nitro; amino; C$_{1-8}$alkylamino and C$_{1-8}$dialkylamino; C$_{1-8}$alkoxy; substituted C$_{1-8}$alkoxy wherein the substituent is halo; hydroxy; halogen; cyano, nitro; amino and C$_{1-8}$alkylamino and C$_{1-8}$dialkylamino;

R$_5$ is independently selected from the group consisting of hydrogen; C$_{1-8}$alkyl; C$_{1-8}$alkylcarbonyl; aroyl; carbamoyl; amidino; (C$_{1-8}$alkylamino)carbonyl; (arylamino)carbonyl and arylC$_{1-8}$alkylcarbonyl;

R$_6$ is independently selected from the group consisting of hydrogen and C$_{1-8}$alkyl;

p is 1–3;

q is 1–3;

and enantiomers, diastereomers, and pharmaceutically acceptable salts thereof, provided that:

when L is C$_{1-8}$alkylene, C$_{2-10}$alkenylene, C$_{2-10}$alkynylene, C$_{3-7}$cycloalkylene, C$_{3-7}$cycloalkylC$_{1-4}$alkylene, arylC$_{1-4}$alkylene or α-aminoalkylene;

then Z is phenyl, N-sulfonamido or N-(aryl)sulfonamido;

when L is (N-methylene)piperazin4-yl;

then Z is phenyl or naphthyl;

when L is (N-methylene)pyrrolidin-3-yl or (N-methylene)piperidin-4-yl;

then Z is N-sulfonamido, N-(aryl)sulfonamido, 2,3-dihydro-2-oxo-1H-benzimidazol-1-yl; benzamido, phenylureido, phenylacetamido or (phenoxy)carbonylamino;

when L is (N-methylene)4-acetyl-piperidin4-yl;

then Z is phenyl or naphthyl and Y is carbonyl;

when L is (N-methylene)piperidin-4,4-diyl;

then Z is 1-aryl-2,3-dihydro4-oxo-imidazol-5,5-diyl and Y is carbonyl;

and when B$_1$ and B$_2$ are both methylene thus forming a six-membered ring (an aminotetralin) and when L is selected from the group consisting of C$_{1-8}$alkylene; C$_{2-10}$alkenylene; C$_{2-10}$alkynylene or arylC$_{1-4}$alkylene;

then Z cannot be N-sulfonamido, N-(aryl)sulfonamido or phenyl;

all enantiomers and diastereomers of compounds of formula A are part of the present invention, as are pharmaceutically acceptable salts thereof.

Preferred compounds among the compounds of this invention are those wherein B$_1$ and B$_2$ form a six-membered ring and m=1–3.

As used herein unless otherwise noted the terms "alkyl" and "alkoxy" whether used alone or as part of a substituent group, include straight and branched chains having 1–8 carbon atoms. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. The term "aryl" is intended to include phenyl and naphthyl and aroyl is intended to include arylacyl. The term "acyl" is intended to include C$_{1-8}$alkylcarbonyl. The term "halo", unless otherwise indicated, includes bromo, chloro, fluoro and iodo. The term "cycloalkyl" is intended to include cycloalkyl groups having 3–7 carbon atoms. With reference to substituents, the term "independently" means that when more than one of such substituent is possible, such substituents may be the same or different from each other.

Those compounds of the present invention which contain a basic moiety can be converted to the corresponding acid addition salts by techniques known to those skilled in the art. Suitable acids which can be employed for this purpose include hydrochloric, hydrobromic, hydriodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. In general, the acid addition salts can be prepared by reacting the free base of compounds of formula A with the acid and isolating the salt.

Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

For the treatment of disorders of the central nervous system, the pharmaceutical compositions described herein will typically contain from 1 to about 1000 mg of the active ingredient per dosage; one or more doses per day may be administered. Determination of optimum doses and frequency of dosing for a particular disease state or disorder is within the experimental capabilities of those knowledgeable in the treatment of central nervous system disorders. The preferred dose range is 1–100 mg/kg.

As modulators of the NPY5 receptor, the compounds of Formula A are useful for treating feeding disorders such as obesity, anorexia nervosa and bulimia nervosa, and abnormal conditions such as epilepsy, depression, anxiety and sexual/reproductive disorders in which modulation of the NPY5 receptor may be useful. The compounds compete with the endogenous ligands NPY and PYY and possibly non-endogenous ligands, and bind to the NPY5 receptor. In addition, the compounds demonstrate antagonist activity by antagonizing the action of NPY upon binding to the Y5 receptor.

The compounds described herein are ligands of the NPY5 receptor, but are not necessarily limited solely in their pharmacological or biological action due to binding to this or any neuropeptide, neurotransmitter or G-protein coupled receptor. For example, the described compounds may also undergo binding to dopamine or serotonin receptors. The compounds described herein are potentially useful in the regulation of metabolic and endocrine functions, particularly those associated with feeding, and as such, may be useful for the treatment of obesity. In addition, the compounds described herein are potentially useful for modulating other endocrine functions, particularly those controlled by the pituitary and hypothalamic glands, and therefore may be useful for the treatment of inovulation/infertility due to insufficient release of luteinizing hormone (LH) or luteal phase defect.

The present invention comprises pharmaceutical compositions containing one or more of the compounds of Formula A. In addition, the present invention comprises intermediates used in the manufacture of compounds of Formula A.

Examples of particularly preferred compounds of formula A include:

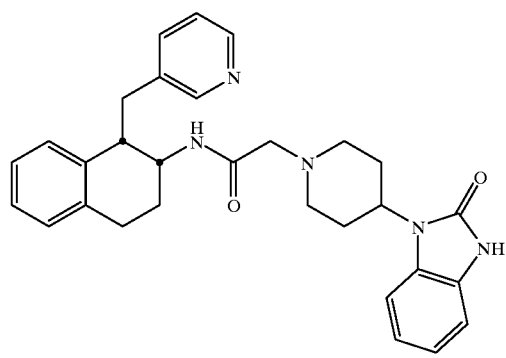

-continued

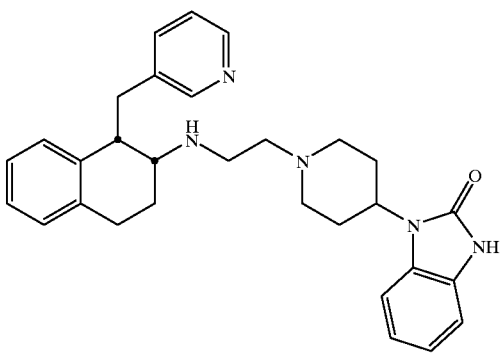

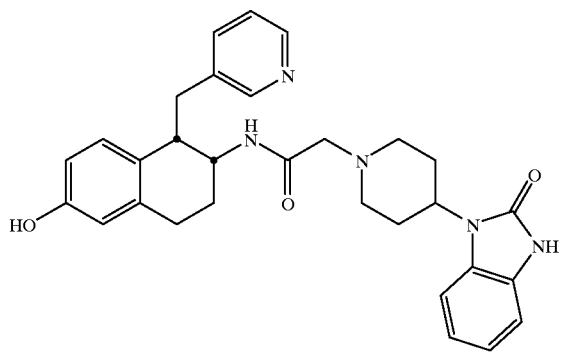

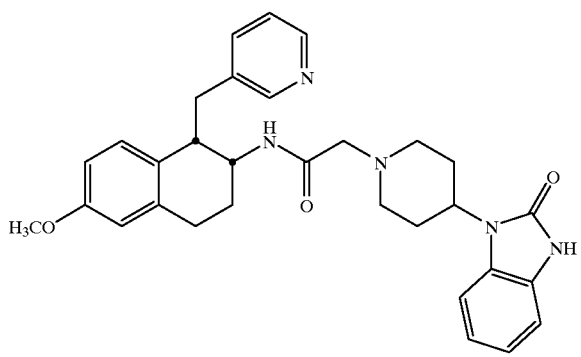

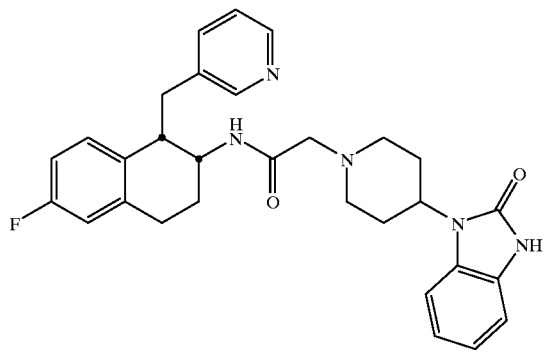

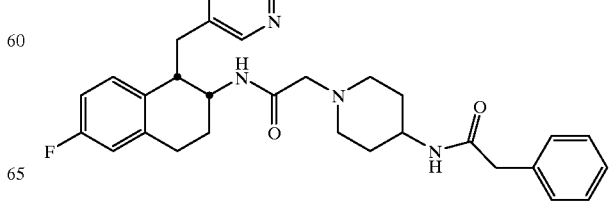

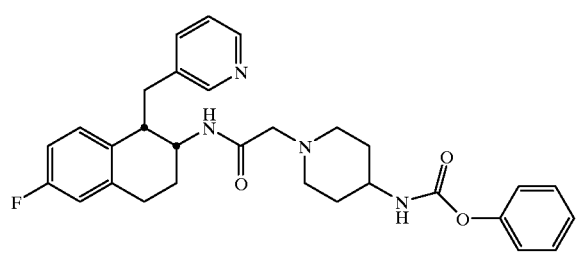
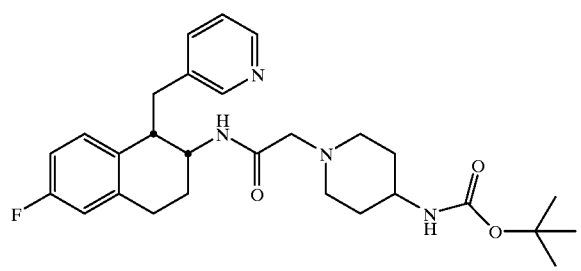
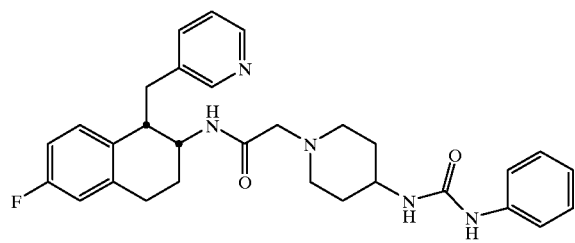
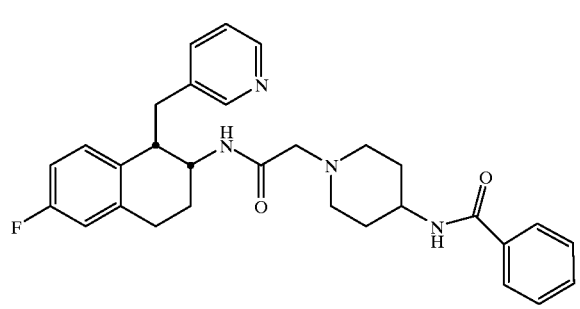
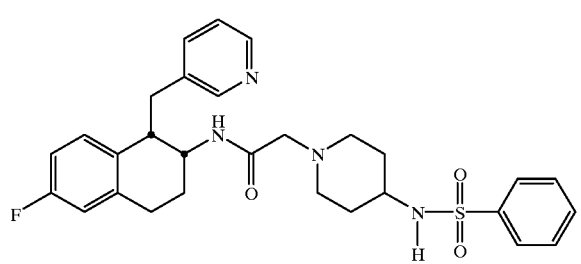
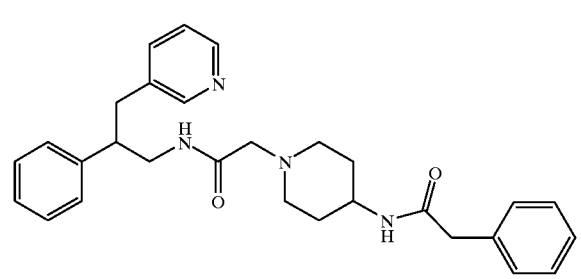

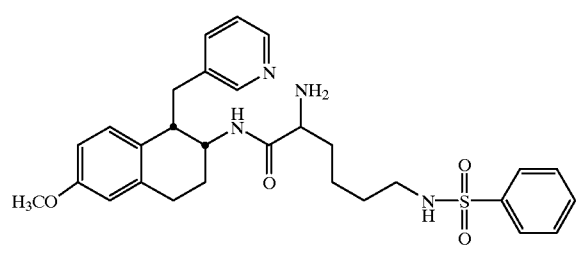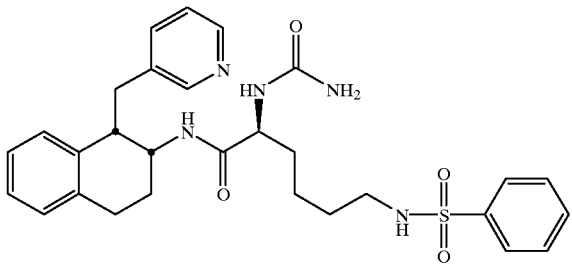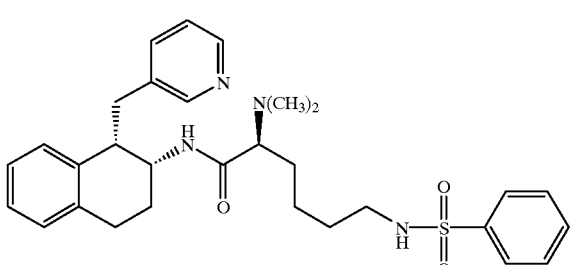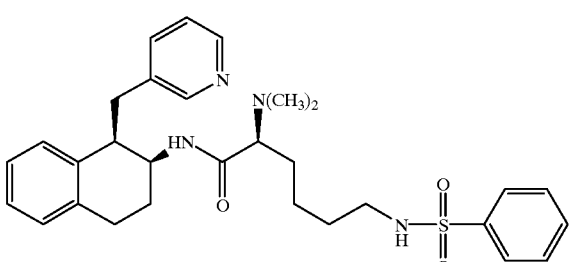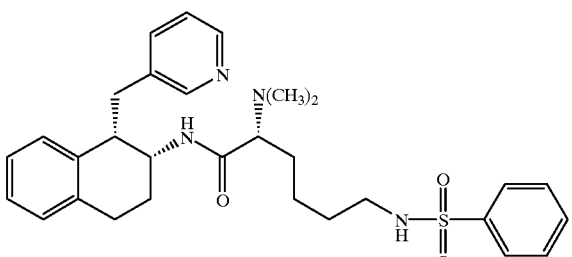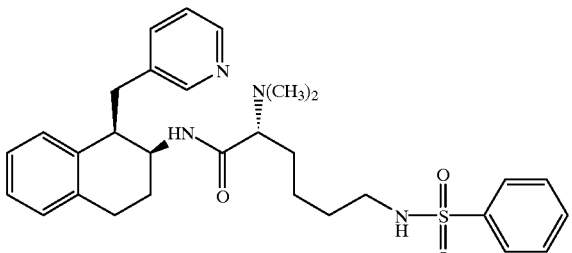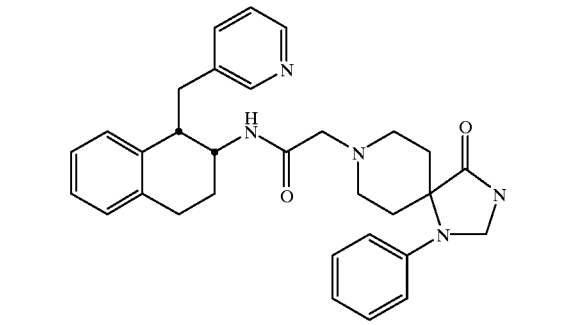

-continued
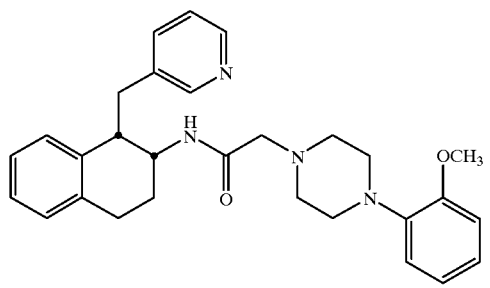
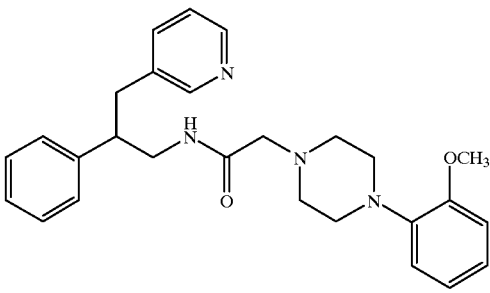
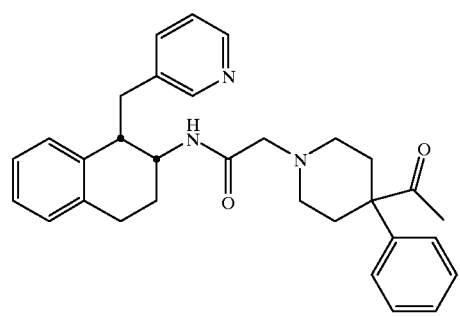
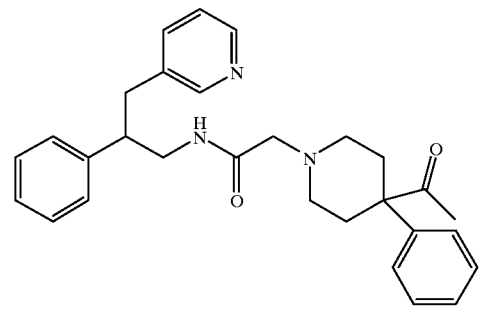
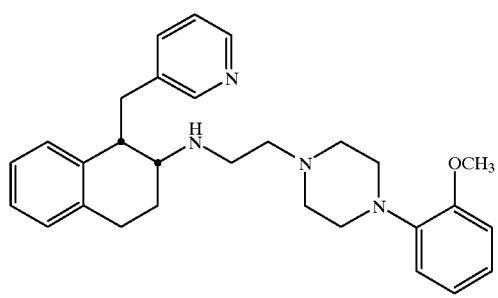
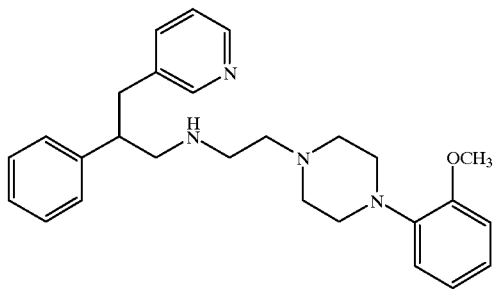
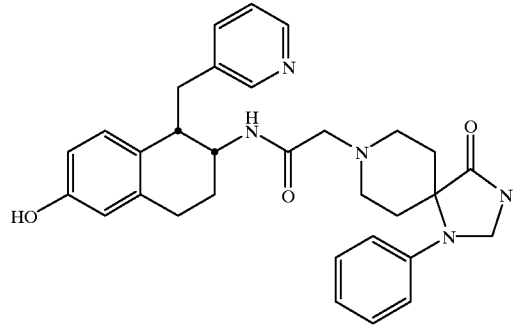
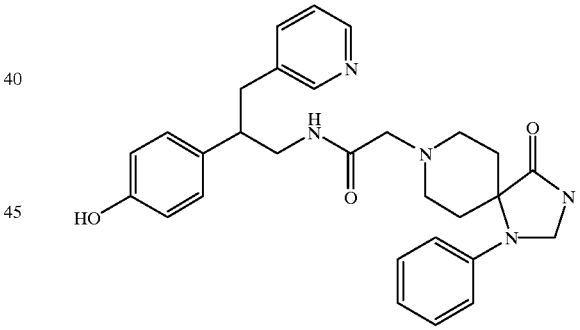
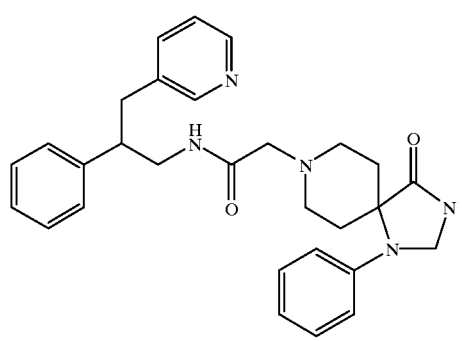
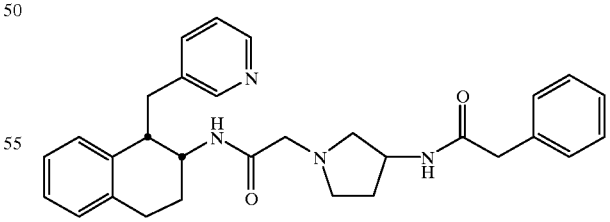
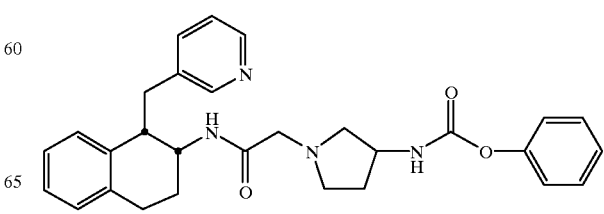

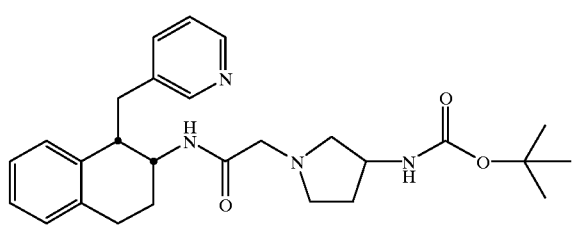
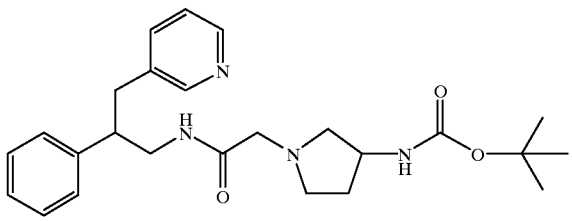
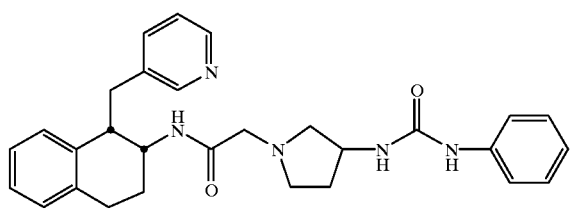
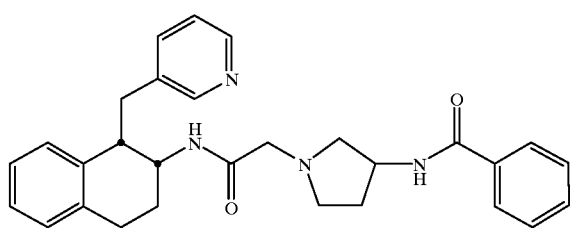
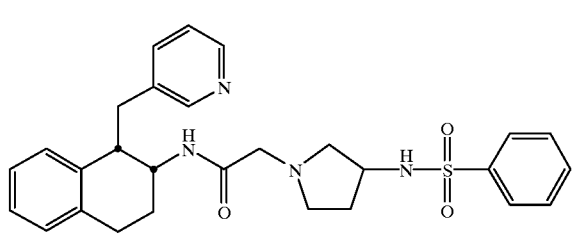
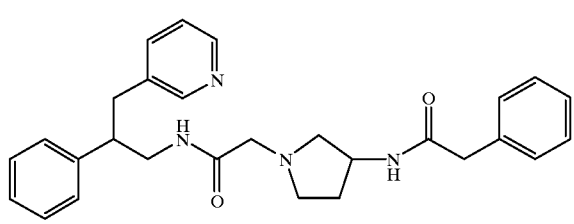
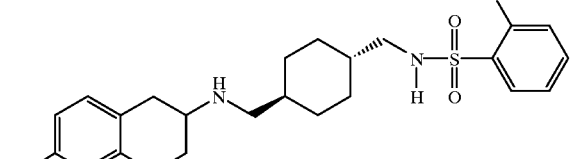
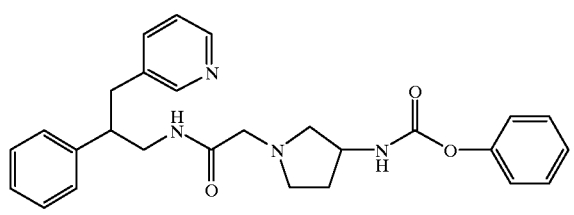
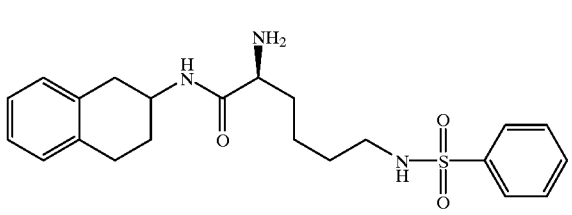

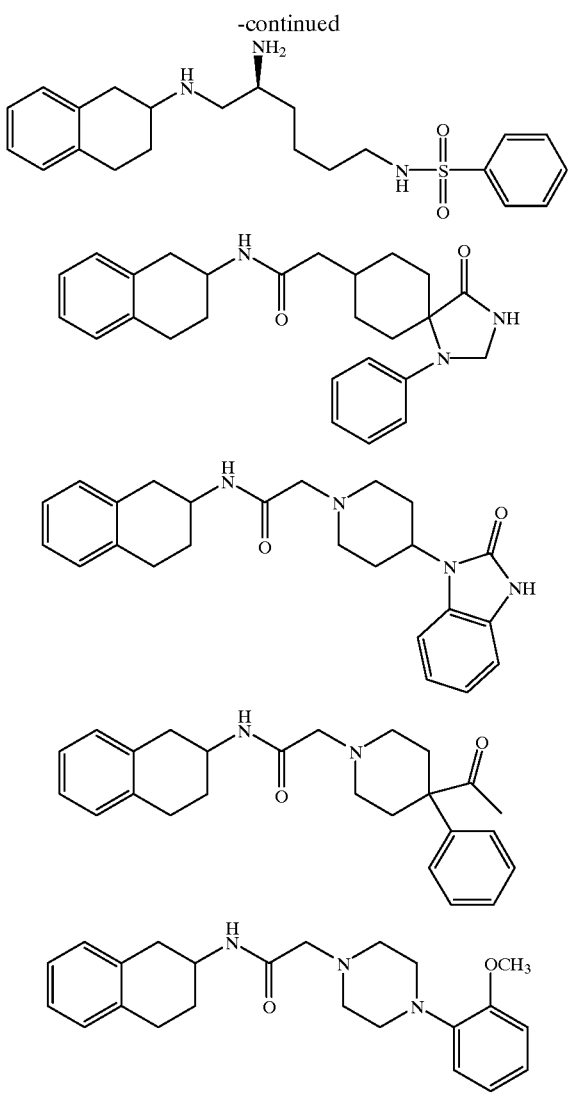

DETAILED DESCRIPTION OF THE INVENTION

The amines and amides of formula A that comprise this invention are synthesized via several distinct chemical syntheses as outlined in Schemes 1–26; each synthetic route consists of several sequential chemical operations that can be generalized as described below. In cases in which $B_1$ and $B_2$ together form a six-membered ring or a five-membered ring (an aminotetralin or an aminoindane, respectively), the general synthesis entails the following operations:

Introduction of the α-substituent onto the tetralone (or indanone) nucleus

Conversion to the corresponding α-substituted-β-aminotetralin (or α-substituted-aminoindane)

Acylation of the aminotetralin (or aminoindane) to afford amides of formula A

Reduction to produce amines of formula A

Protecting group manipulations may be needed at various stages of the syntheses.

In cases where $B_1$ and $B_2$ are hydrogen, the general synthesis consists of the following operations:

Introduction of the α-substituent onto a phenylacetonitrile

Reduction to the corresponding β-substituted phenethylamine

Acylation of the phenethylamine to afford amides of formula A

Reduction to produce amines of formula A

Protecting group manipulations may be needed at various stages of the syntheses.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halohydrocarbon solvents. In those cases wherein the product is isolated as the acid addition salt the free base may be obtained by techniques known to those skilled in the art. In those cases in which the product is isolated as an acid addition salt, the salt may contain one or more equivalents of the acid.

Specifically, an appropriately substituted β-tetralone (II) is reacted with an aryl or heteroaryl aldehyde in the presence of a base such as piperidine, in an inert halohydrocarbon, ethereal or hydrocarbon solvent, such as benzene, from ambient temperature to reflux, to afford the corresponding α-benzylidenyl-β-tetralone or α-heteroarylmethylidenyl-β-tetralone (III). The β-tetralone (III) is dissolved in an inert hydrocarbon, ethereal, ester or alcohol solvent, such as methanol, and reacted with hydrogen gas at a pressure from ambient pressure to 100 p.s.i. in the presence of a suitable catalyst such as palladium on carbon. The reaction is performed at a temperature from ambient temperature to reflux, to yield the desired α-substituted-β-tetralone (IV) (Scheme 1).

An alternative method for the preparation of α-substituted-β-tetralones (IV) involves the reaction of an appropriately substituted β-tetralone (II) with a base such as pyrrolidine in an inert halohydrocarbon solvent such as dichloromethane or hydrocarbon solvent such as benzene, under Dean-Stark conditions (removal of water) or in an alcohol solvent such as methanol, from ambient temperature to reflux, to afford enamine (V). Alkylation of enamine (V) is accomplished by reaction with a benzylic, heterocyclicalkyl or an allylic halide in an inert solvent such as acetonitrile, at a temperature from ambient temperature to reflux, to afford the α-substituted-β-iminium salt (VI). Hydrolysis of the salt (VI) to produce the desired α-substituted-β-tetralone product (IV) is accomplished by reaction of (VI) with water and an inorganic or organic acid such as hydrochloric or glacial acetic acid in an inert hydrocarbon, ethereal, alcohol or halohydrocarbon solvent, or a mixture thereof, such as methanol and dichloromethane (Scheme 1).

Scheme 1

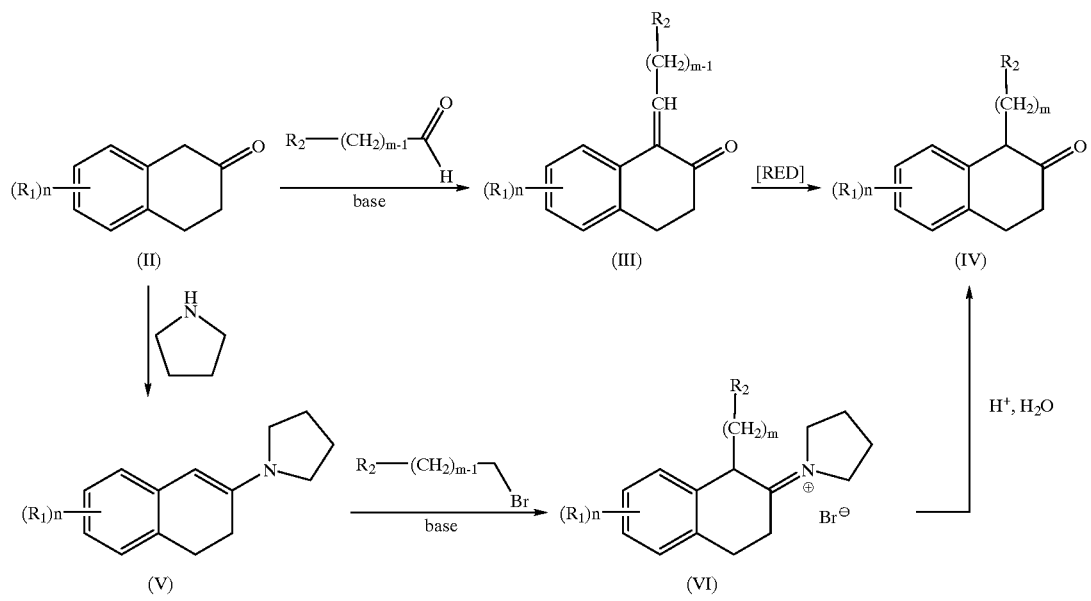

wherein m = 1–3

The α-substituted-β-tetralones (IV) are converted to the corresponding aminotetralins via reaction with an ammonium salt such as ammonium acetate in the presence of a reducing agent such as sodium cyanoborohydride, for example, in an inert halohydrocarbon, hydrocarbon, ethereal or alcohol solvent such as methanol to produce the cis-aminotetralin (VII). In some cases, the trans-aminotetralin (VIII) is also formed as a minor product; both sets of diastereomers are part of this invention. The aminotetralins (VII) can also be isolated as acid addition salts by treatment with an organic or an inorganic acid, such as trifluoroacetic acid or hydrochloric acid, for example (Scheme 2).

-continued

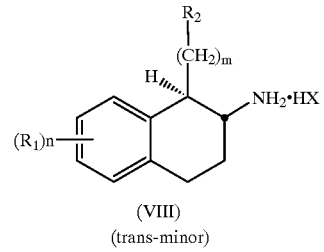

wherein HX is the acid

Compounds in which m=0 are prepared from an appropriately substituted aminotetralin (VII; m=0) starting from 1-tetralones using the synthetic sequence shown in Scheme 2a.

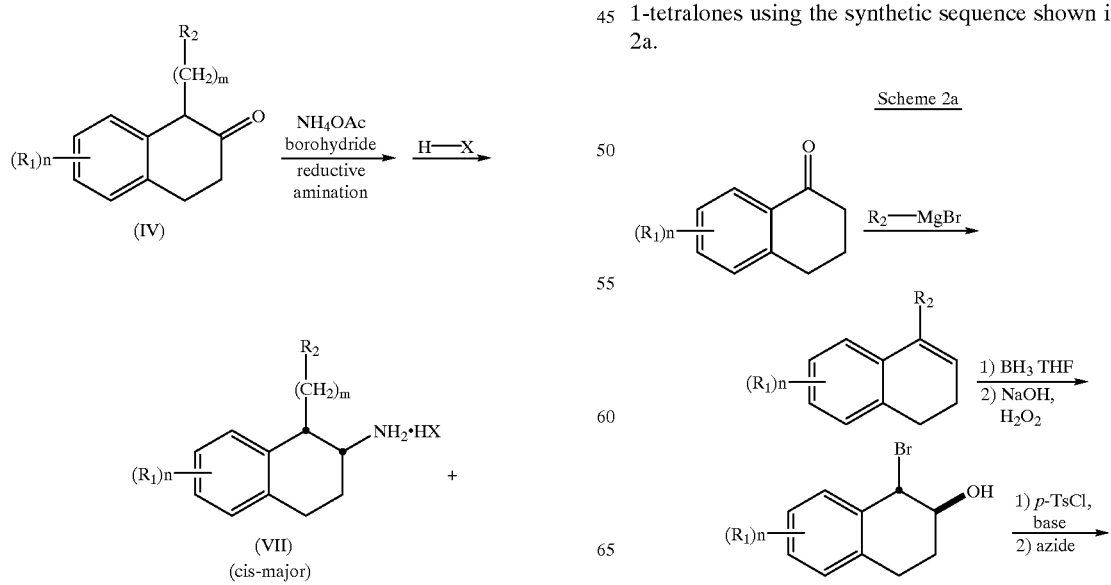

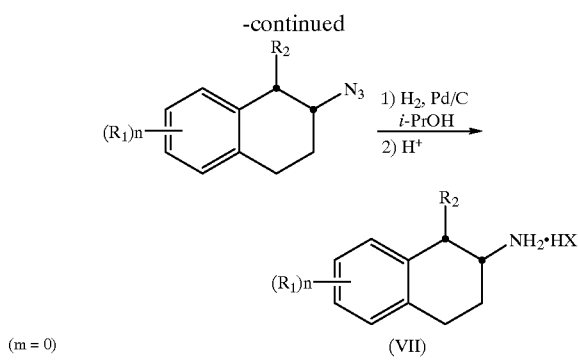

Substituted phenethylamines (XI) are prepared by reacting an appropriately substituted phenylacetonitrile (IX) with an aryl or heteroaryl aldehyde in the presence of a base, such as sodium methoxide, in an inert alcohol solvent, such as methanol, at a temperature from ambient temperature to reflux, to afford α,β-unsaturated nitrile (X). Subsequent reduction of nitrile (X), for example, via reaction with hydrogen gas in the presence of a platinum oxide catalyst at a pressure from atmospheric pressure to approximately 100 psi, in an inert solvent such as aqueous alcohol, at a temperature from ambient temperature to reflux, affords β-substituted phenethylamine (XI). Alternatively, reaction of phenylacetonitrile (X) with an arylalkyl-, heteroarylalkyl- or alkyl halide, for example, such as allyl bromide in the presence of a base such as sodium methoxide or sodium hydride, in an inert solvent such as tetrahydrofuran or acetonitrile respectively, at a temperature from ambient to reflux, affords α-substituted phenylacetonitrile (XII). Subsequent reduction of nitrile (XII), for example, by hydrogenolysis, produces β-substituted phenethylamine (XI) (Scheme 3).

The β-aminotetralins (VII) and the phenethylamines (XI) described above are acylated via suitable amidation methods (see Gross and Meienhofer, Eds., "The Peptides", Vols. 1–3, Academic Press, New York, N.Y., 1979–1981). A carboxylic acid is converted to an activated ester via peptide coupling methods known to those skilled in the art, and subsequently reacted with an aminotetralin (VII) or phenethylamine (XI), to afford the corresponding amides.

For example, a carboxylic acid such as trans-4-(2-fluorobenzenesulfonamido)methylcyclohexane carboxylic acid or 4-(tert-butoxycarbonyl)aminomethylcyclohexane carboxylic acid is reacted with HBTU (2-(1H-benzotriazole-1-yl)-1,1,3,3-tetramethyluronium hexafluorophosphate and an appropriate phenethylamine (XI), in the presence of a base such as diisopropylethylamine, in an inert solvent such as N,N-dimethylformamide, at a temperature from ambient temperature to reflux, to afford amide (XIII) or amide (XIV) respectively. Cleavage of the BOC (butoxycarbonyl) protecting group from carbamate (XIV) with trifluoroacetic acid produces the free amine, which is sulfonylated to yield amide (XIII).

The N-substituted phenethylamine compounds A of the invention are prepared via reduction of amide (XIII) by reaction with a suitable reducing agent such as borane-tetrahydrofuran complex or lithium aluminum hydride in an inert hydrocarbon solvent such as toluene or ethereal solvent such as tetrahydrofuran, at a temperature from ambient temperature to reflux. The final product can be isolated as an acid addition salt upon treatment with a suitable organic acid such as trifluoroacetic acid or an inorganic acid such as hydrochloric acid (Scheme 4).

Scheme 3

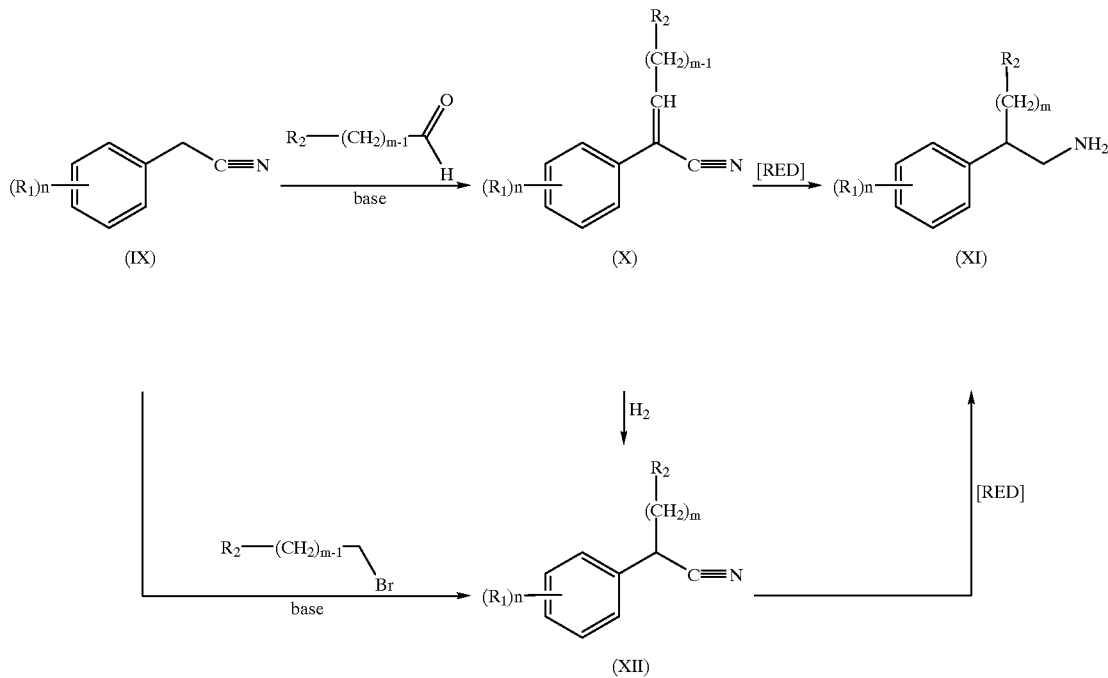

Scheme 4
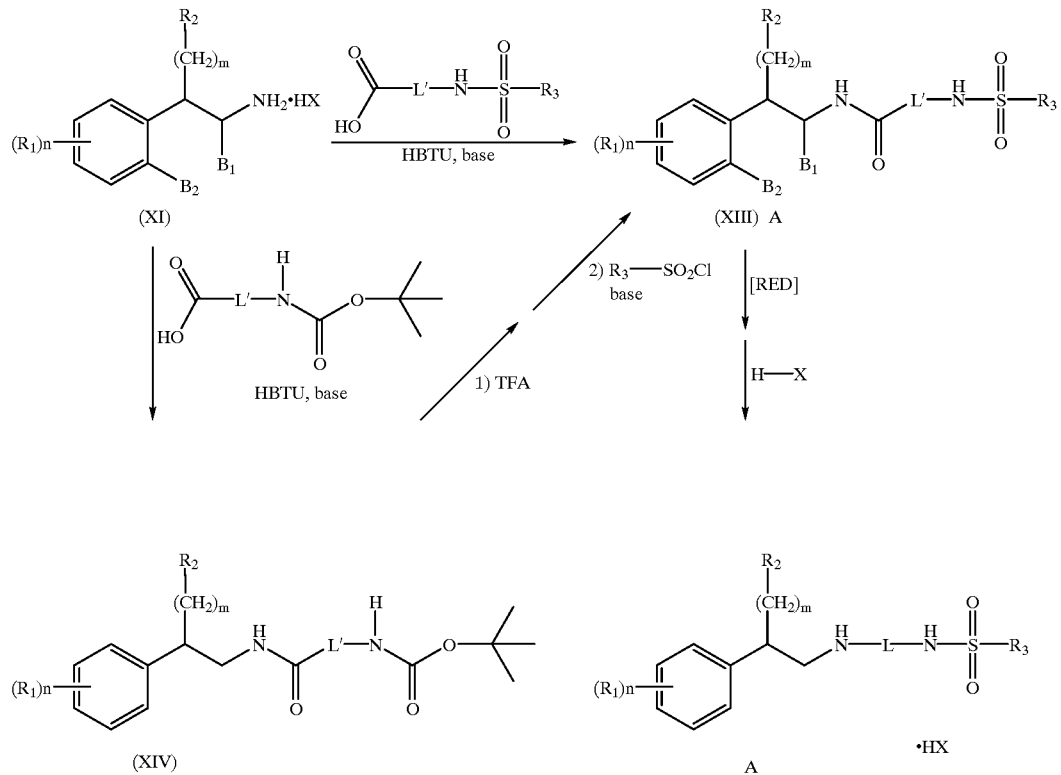
L' = L less one —CH$_2$—
B$_1$ and B$_2$ = H
Aminotetralin analogs (B$_1$ and B$_2$ each are methylene) are prepared using the chemistry described above but replacing the phenethylamine (XI) starting material with an aminotetralin (VII) (Scheme 5).
Scheme 5
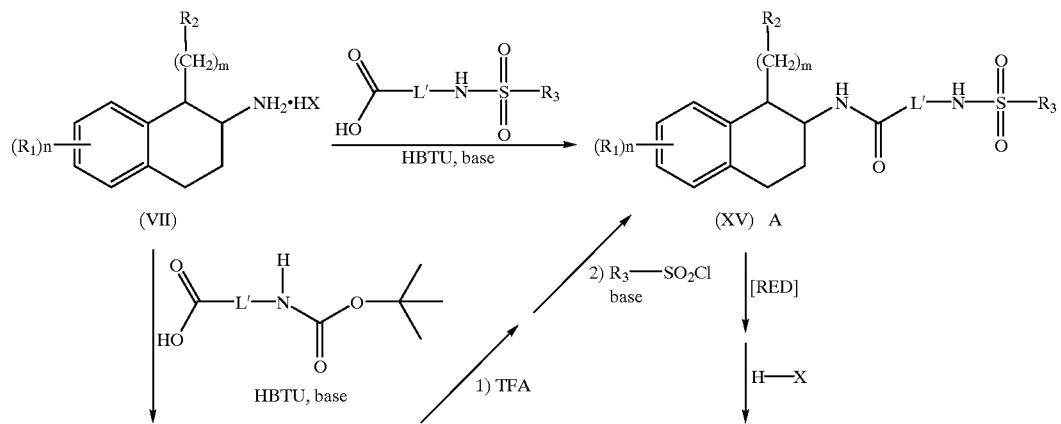

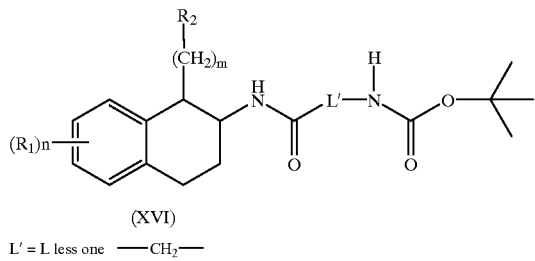

(XVI)

L' = L less one —CH$_2$—

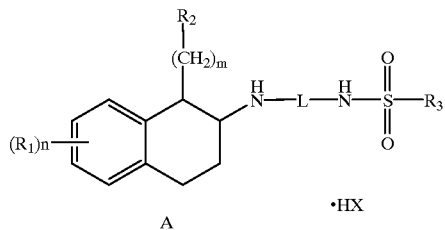

A

·HX

Compounds of formula A in which Z=2,3-dihydro-2-oxo-1H-benzimidazol-1-yl and L=(N-methylene)piperidin-4-yl are prepared from β-aminotetralins (VII) or phenethylamines (XI) and [4-(2-keto-1-benzimidazolinyl)piperidin-1-yl]acetic acid (Schemes 6–7). For example, 4-(2-keto-1-benzimidazolinyl)piperidine is reacted with a bromoacetic acid ester, such as ethyl bromoacetate, in the presence of an amine base, such as diisopropylethylamine, in an inert solvent such as acetonitrile, at a temperature ranging from ambient temperature to reflux, to afford ethyl [4-(2-keto-1-benzimidazolinyl)piperidin-1-yl]acetate. This ester is subjected to hydrolysis under basic conditions, for example, by treatment with sodium hydroxide in an alcoholic solution such as aqueous methanol, to yield, upon acidification with an inorganic or organic acid such as hydrochloric or acetic acid for example, [4-(2-keto-1-benzimnidazolinyl)piperidin-1-yl]acetic acid. This carboxylic acid is reacted directly with β-aminotetralins (VII) or phenethylamines (XI), in the presence of an amine base, under peptide coupling conditions described above, to afford benzimidazolinones (XVII) and (XVIII) of formula A in which Y=carbonyl and L=(N-methylene)piperidin-4-yl (Schemes 6–7).

Scheme 6

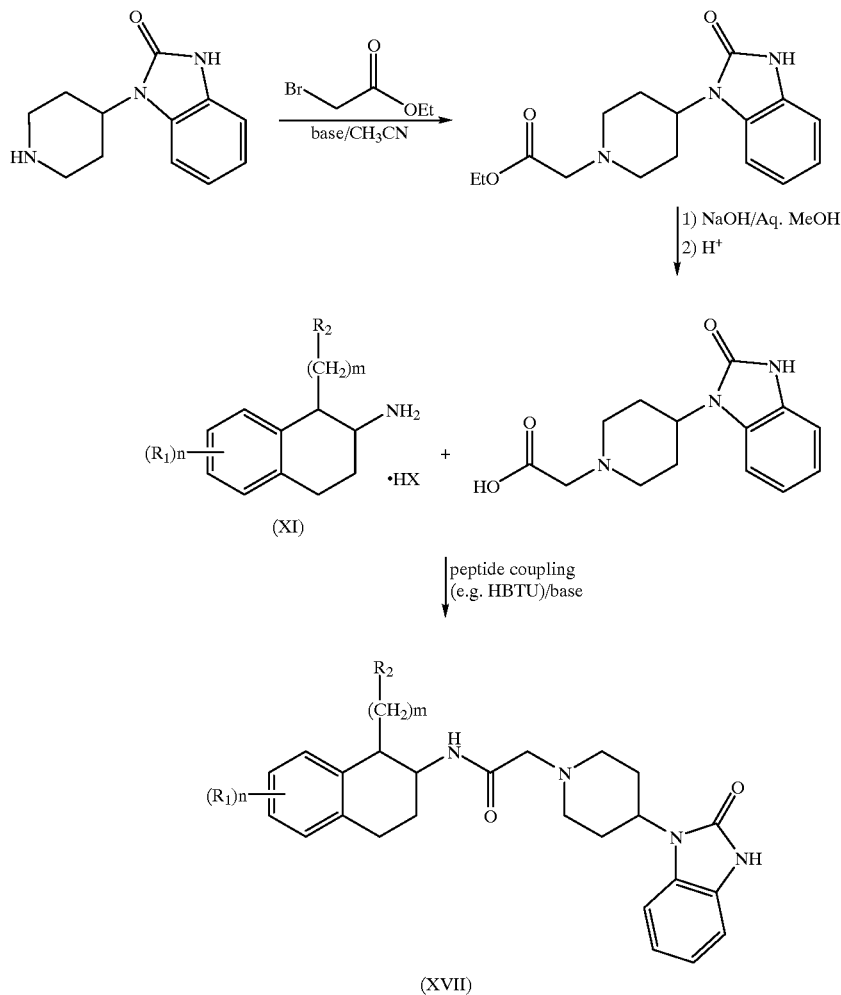

Scheme 7

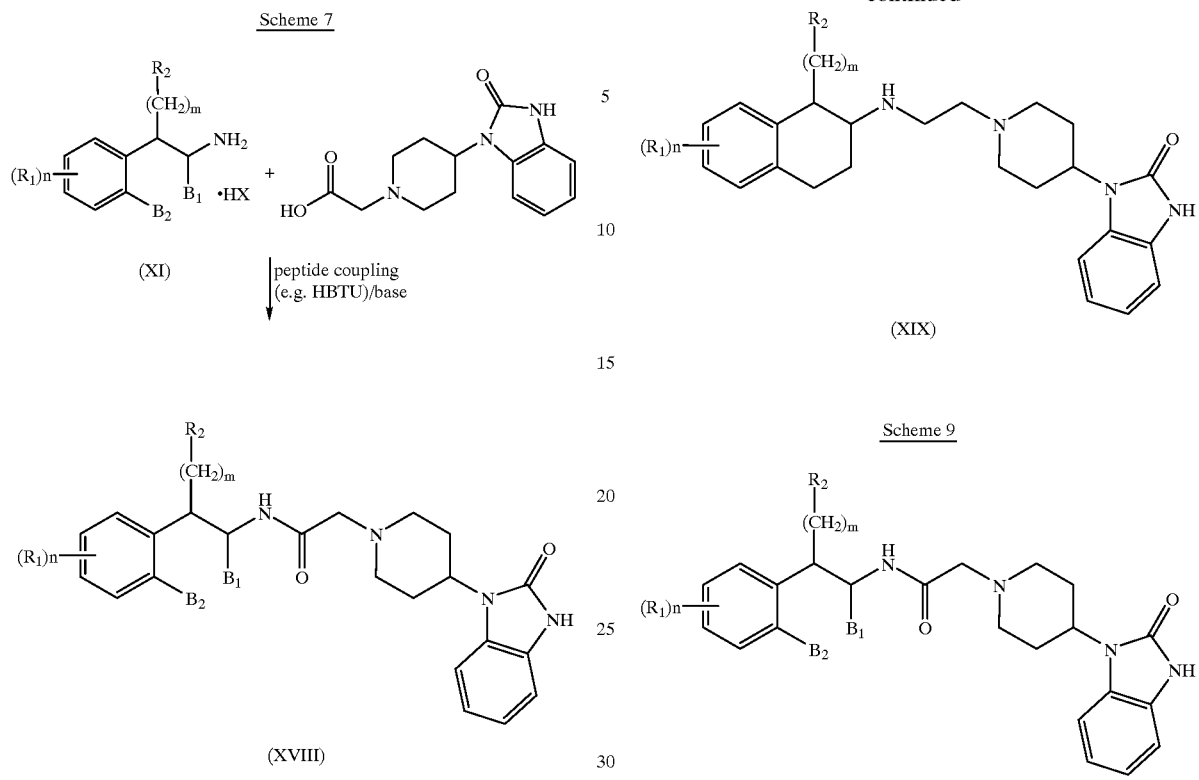

Compounds of formula A in which Y=methylene and L=(N-methylene)piperidin4-yl and Z=2,3-dihydro-2-oxo-1H-benzimidazol-1-yl are prepared by reduction of amide (XVII) and amide (XVIII) with a reducing agent such as borane-tetrahydrofuran complex or lithium aluminum hydride as described above. The use of an aminotetralin (VII) starting material gives rise to products (XIX) (Scheme 8) whereas phenethylamines give the analogous amines (XX) (Scheme 9).

Scheme 8

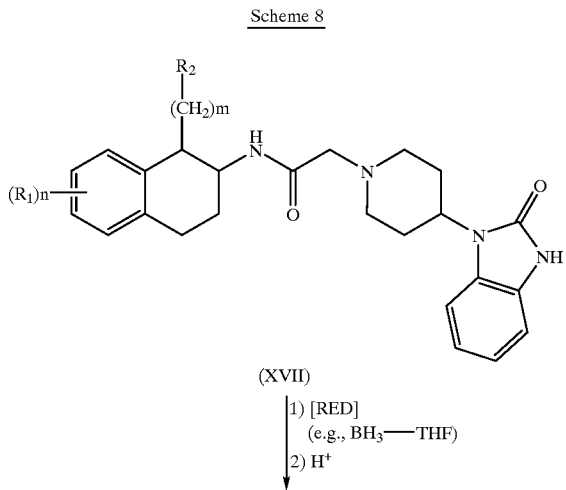

Compounds of formula A in which Y=carbonyl, L=(N-methylene)piperazin-4-yl and Z=phenyl are prepared by reacting a phenylpiperazine with a haloacetic acid ester, such as, for example, ethyl bromoacetate, in the presence of an amine base, such as diisopropylethylamine, in an inert solvent such as acetonitrile, at a temperature ranging from ambient temperature to reflux, to afford ethyl (4-arylpiperazin-1-yl)acetate. This ester is subjected to hydrolysis under basic conditions, for example, by treatment with sodium hydroxide in an aqueous methanol, to yield, upon acidification with an inorganic or organic acid such as hydrochloric or acetic acid for example, (4-arylpiperazin-1-yl)acetic acid. This carboxylic acid is reacted with β-aminotetralins (VII) or phenethylamines (XI), in the presence of a base, such as triethylamine for example, under peptide coupling conditions described above, to afford arylpiperidines (XXI) and (XXII) respectively, of formula A in which Y=carbonyl, L=(N-methylene)piperazin-4-yl and Z=aryl or substituted aryl (Schemes 10–11).

Scheme 10
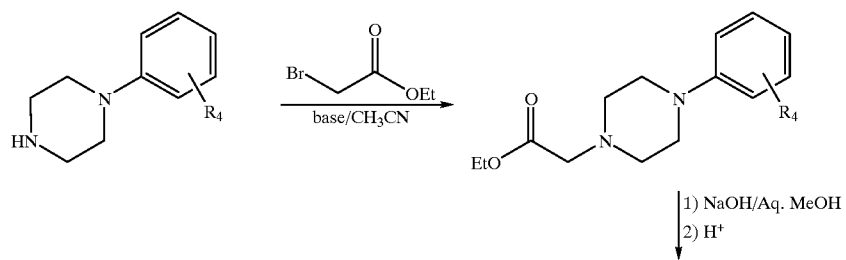
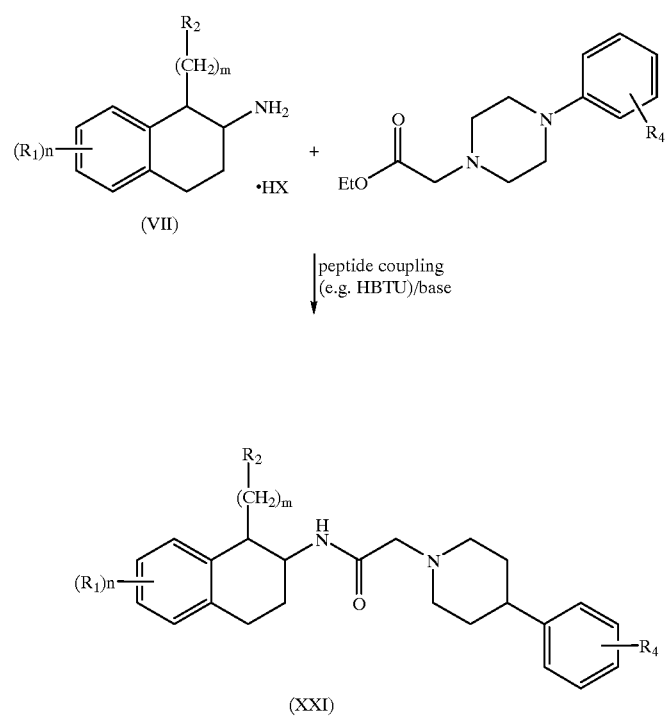
Scheme 11
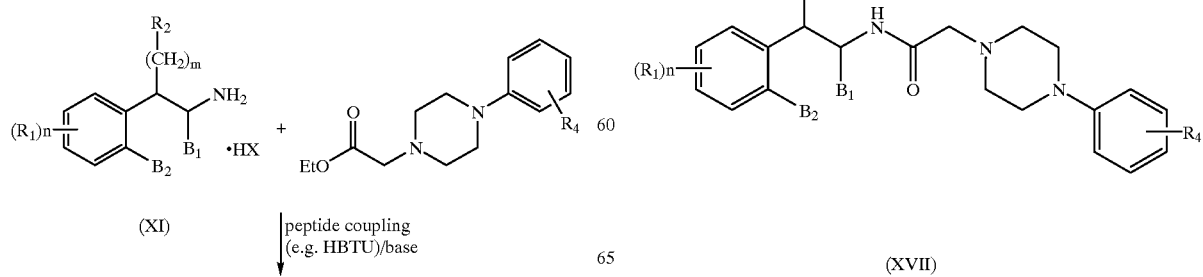

Compounds of formula A in which Y=methylene, L=(N-methylene)piperazin-4-yl and Z=aryl are prepared by reduction of amides (XXI) and (XXII) with a reducing agent such as borane-tetrahydrofuran complex or lithium aluminum hydride (see Scheme 9) to afford aminotetralins (XXIII) and phenethylamines (XIV) respectively (Schemes 12–13).

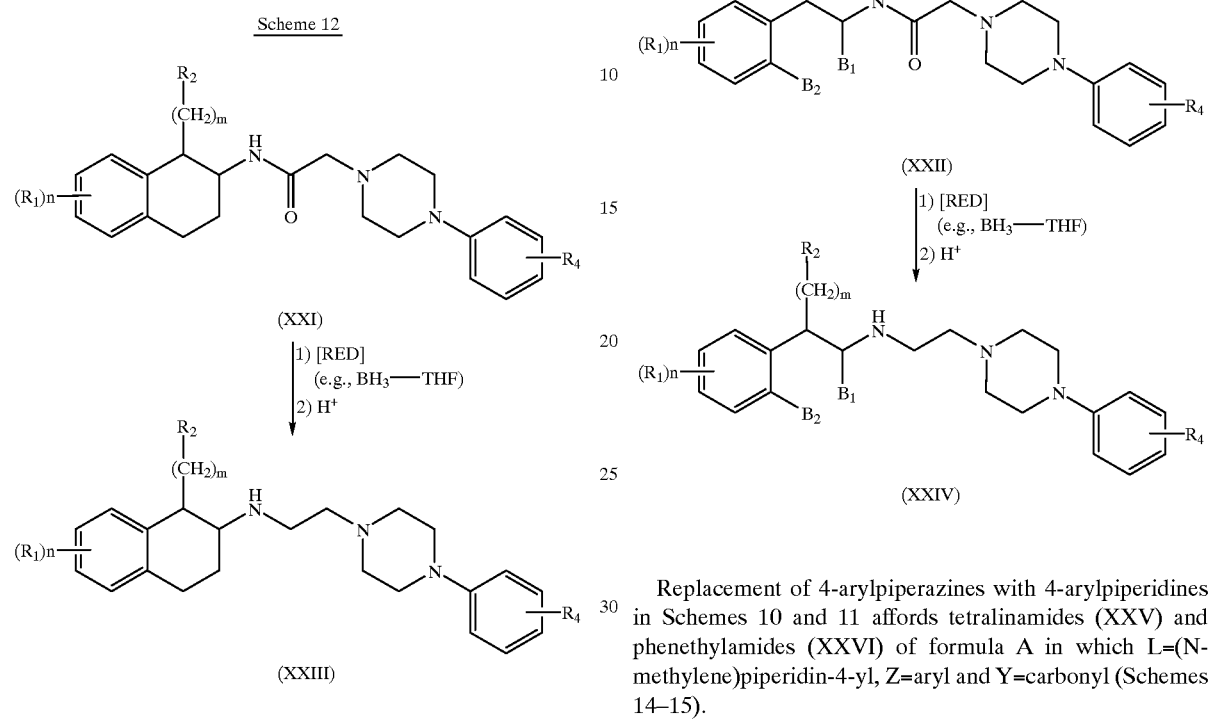

Replacement of 4-arylpiperazines with 4-arylpiperidines in Schemes 10 and 11 affords tetralinamides (XXV) and phenethylamides (XXVI) of formula A in which L=(N-methylene)piperidin-4-yl, Z=aryl and Y=carbonyl (Schemes 14–15).

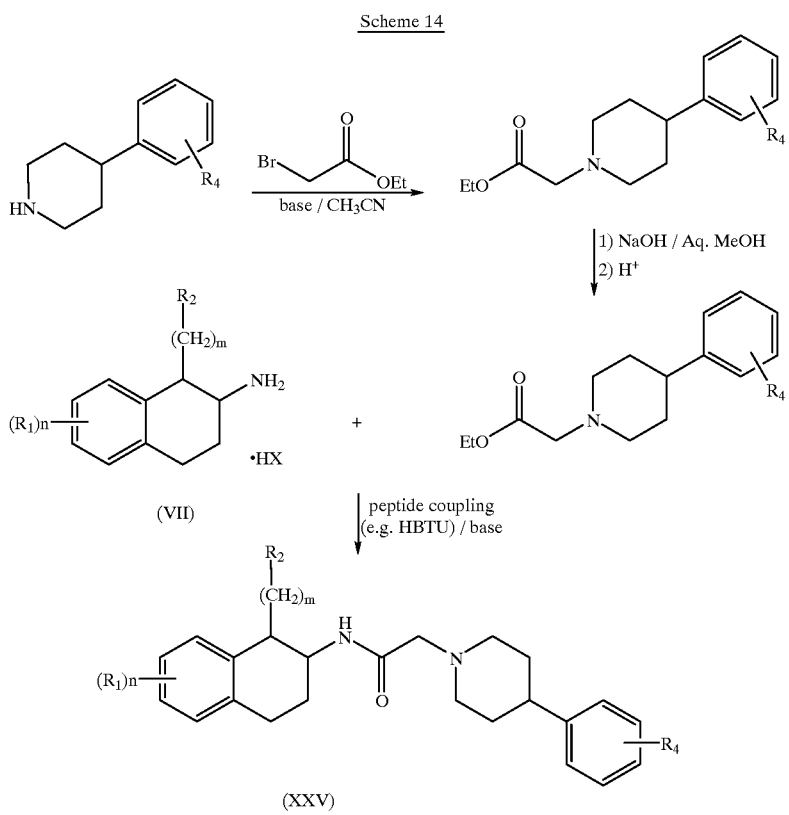

Scheme 15

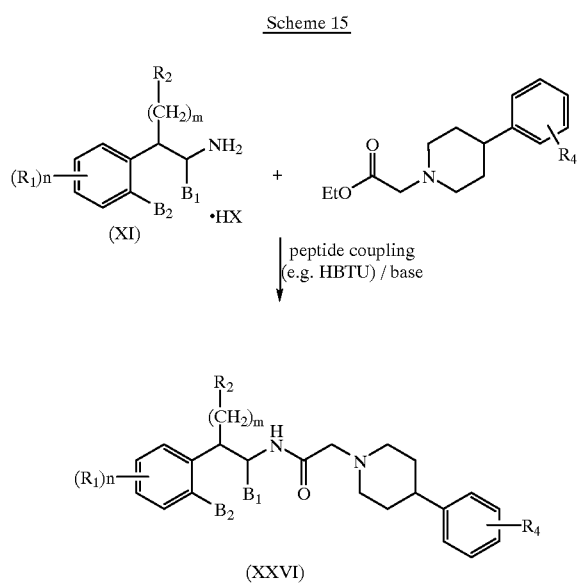

Separately, reduction of amides (XXV) and (XXVI) with a reducing agent such a borane-tetrahydrofuran complex, affords amines (XXVII) and (XXVIII) of formula A in which L=(N-methylene)piperidin4-yl, Z=aryl and Y=methylene (Scheme 16).

Compounds of formula A in which Y=carbonyl, L=(N-methylene)pyrrolidin-3-yl and Z=N-(aryl)sulfonamido are prepared by reacting a suitably protected aminopyrrolidine, such as (3-t-butoxycarbonylamino)pyrrolidine with a haloacetic acid ester, such as, for example, ethyl bromoacetate, in the presence of an amine base, such as diisopropylethylamine, in an inert solvent such as acetonitrile, at a temperature ranging from ambient temperature to reflux, to afford ethyl [(3-t-butoxycarbonylamino)pyrrolidin-1-yl]acetate. This ester is subjected to hydrolysis under basic conditions, for example, by treatment with sodium hydroxide in an aqueous methanol, to yield, upon acidification with an inorganic or organic acid such as hydrochloric or acetic acid for example, [(3-t-butoxycarbonylamino)pyrrolidin-1-yl]acetic acid. This carboxylic acid is reacted with β-aminotetralins (VII) or phenethylamines (XI), in the presence of a base, such as triethylamine for example, under peptide coupling conditions described above, to afford tetralinamides (XXIX) and phenethyamides (XXX) respectively. Subsequent treatment with an organic or inorganic acid, such as trifluoroacetic acid and hydrochloric acid for example, produces the free terminal amines (XXXI) and (XXXII). These materials are sulfonylated by reaction with sulfonyl halides such as benzenesulfonyl chloride for example, in the presence of a base, to afford tetralinamides (XXXIII) and phenethyamides (XXXIV) (Schemes 17–18).

Scheme 16

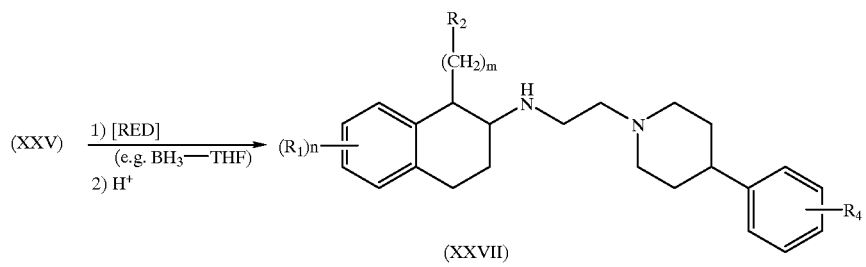

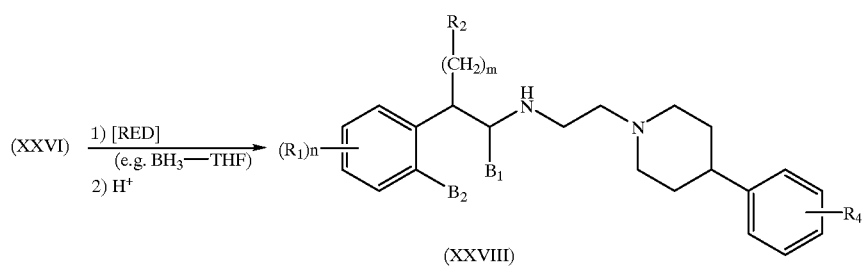

Scheme 17

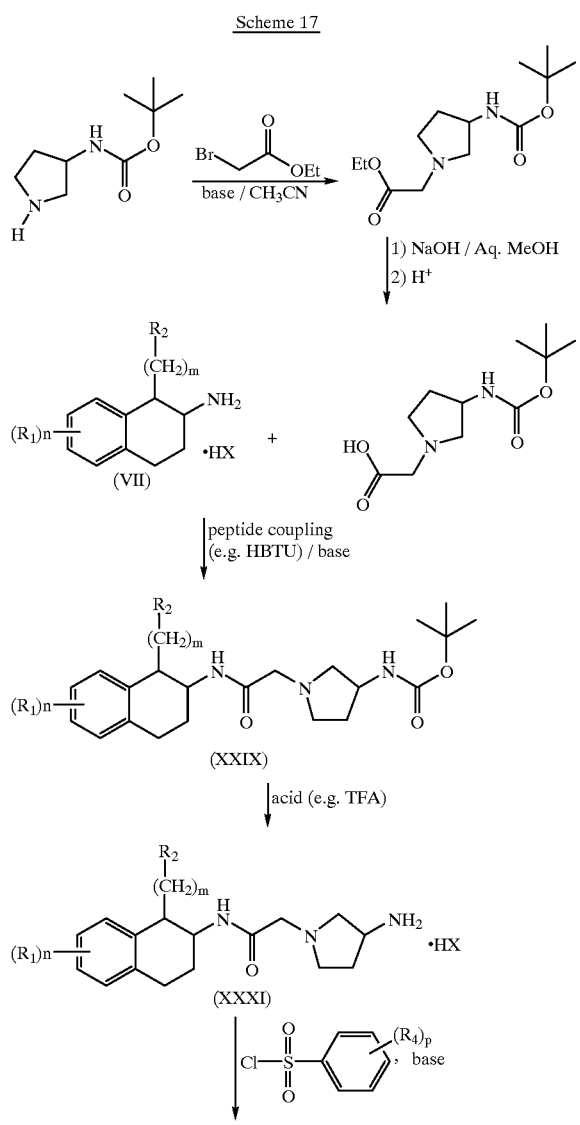

Scheme 18

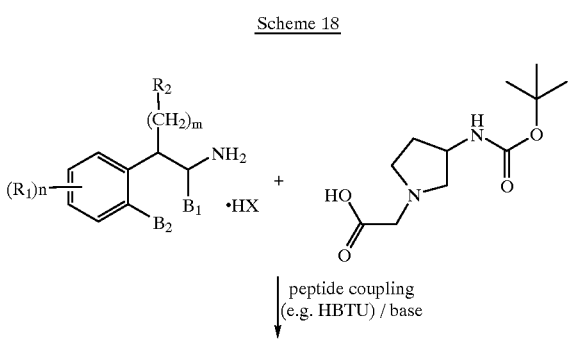

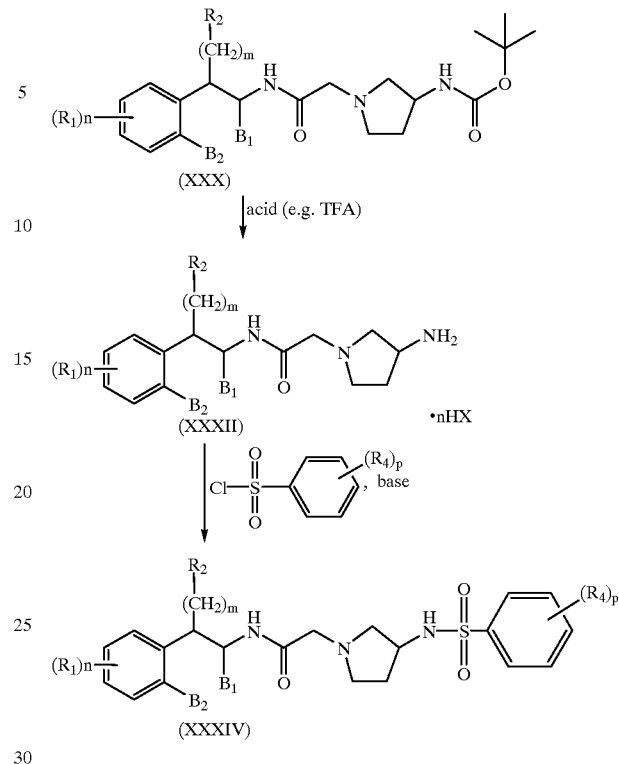

Separately, reduction of amides (XXXIII) and (XXXIV) with a reducing agent such a borane-tetrahydrofuran complex, affords amines (XXXV) and (XXXVI) of formula A in which L=N-(methylene)pyrrolidin-3-yl and Z=sulfonamido or (aryl)sulfonamido, Y=methylene (Scheme 19).

Scheme 19

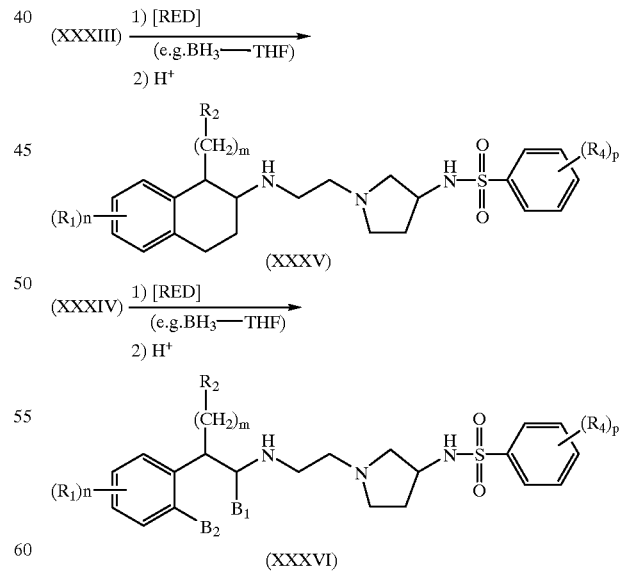

Tetralinamides and phenethylamides of formula A in which Y=carbonyl, L=(N-methylene)pyrrolidin-3-yl and Z=benzamido, phenylureido, phenylacetamido and phenoxycarbonylamino (or butoxycarbonylamino) are prepared by reacting amines (XXXI) and (XXXII) respectively, in an inert solvent at a temperature from ambient temperature to reflux, in the presence of a base such as an amine or hydroxide, with an aroyl halide, an arylisocyanate, an arylacetyl halide or a chloroformate such as phenylchloroformate (or di-tert-butyl dicarbonate) to afford benzamides (XXXVII) and (XXXXI), phenylureas (XXXVIII) and (XXXXII), phenylacetamides (XXXIX) and (XXXXIII) and phenylcarbamate (XXXX) and (XXXIV) respectively (Schemes 20–21).

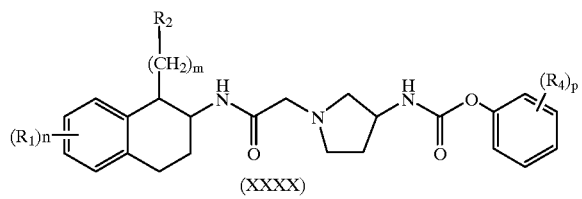

(XXXX)

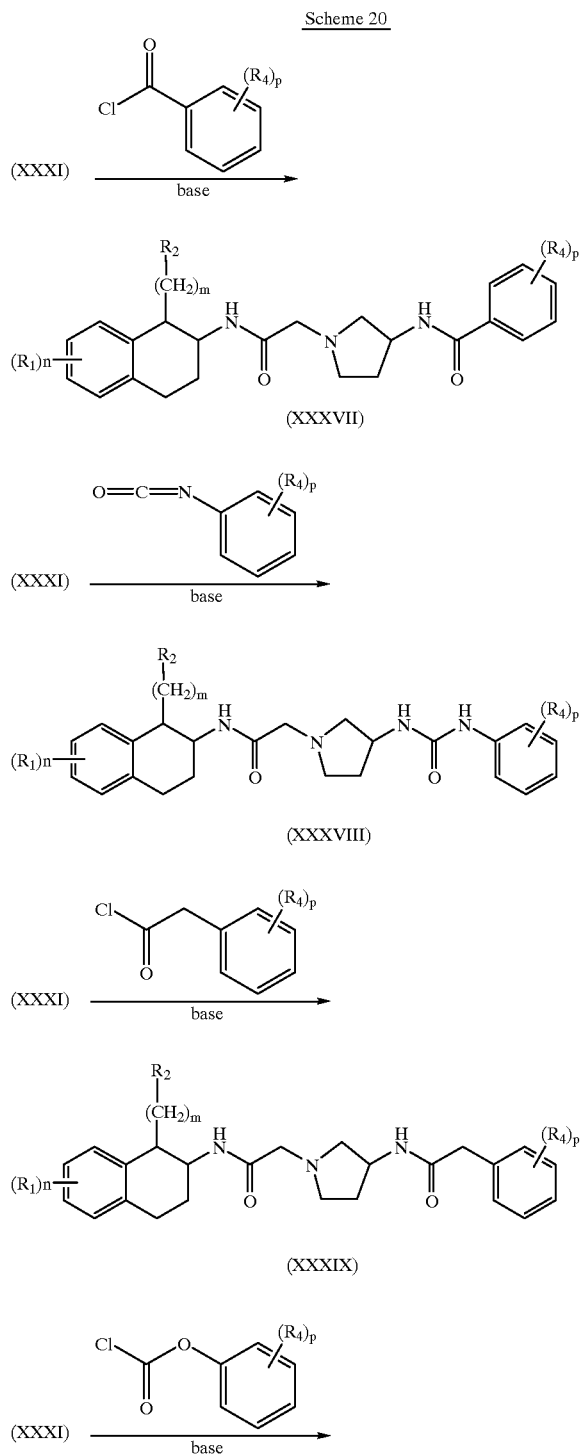

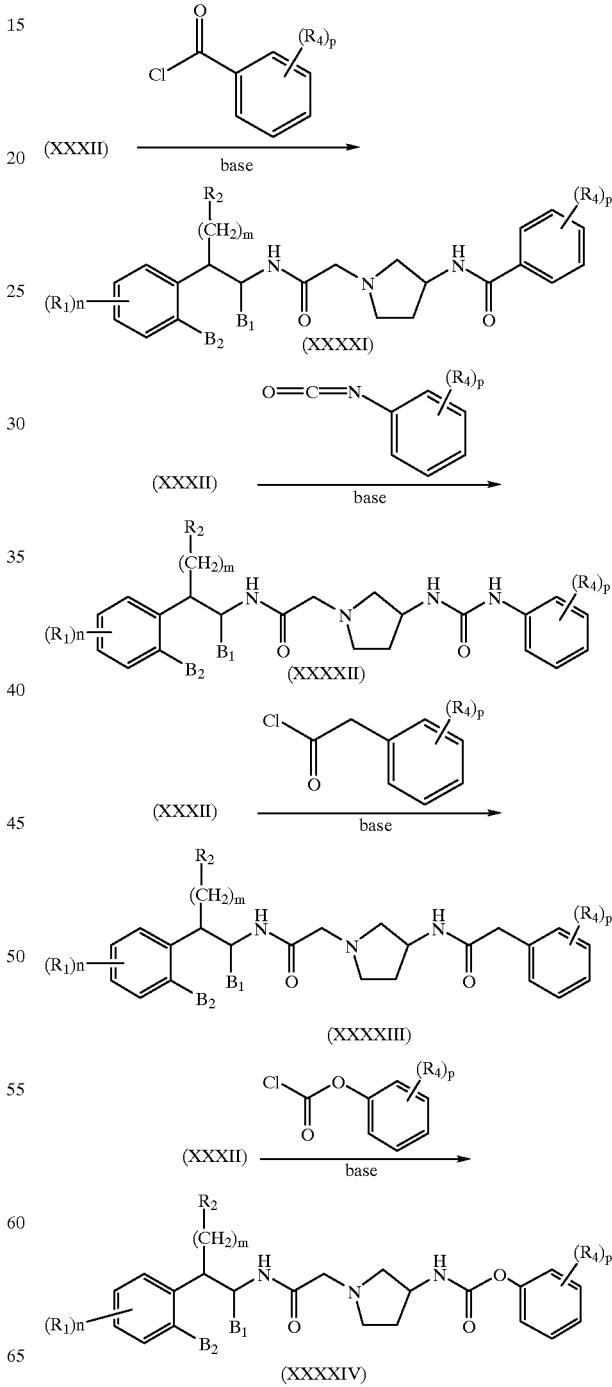

Compounds of formula A in which Y=methylene, L=N-(methylene)pyrrolidin-3-yl and Z=benzamido, phenylureido, phenylacetamido and phenylcarbonylamino (or butoxycarbonylamino) are prepared by reducing amides (XXXI) and (XXXII) to their respective amines (XXXXV) and (XXXXVI) by treatment with a reducing agent such as borane-tetrahydrofuran complex or lithium aluminum hydride. Amines (XXXXV) and (XXXXVI) are subsequently separately reacted with an aroyl halide, an arylisocyanate, an arylacetyl halide or an arylchloroformate (or carbonate such as di-tert-butyl carbonate), in the presence of a base in an inert solvent as described in Scheme 20–21, to afford benzamides (XXXXVII) and (XXXXXI), phenylureas (XXXXVIII) and (XXXXXII), phenylacetamides (XXXXIX) and (XXXXXIII) and phenylcarbamates (XXXXX) and (XXXXXIV), respectively (Schemes 22–24).

Scheme 22

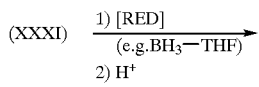

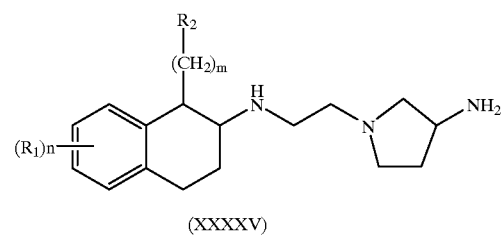

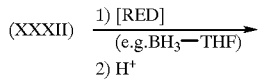

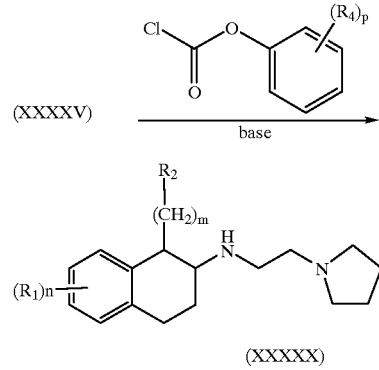

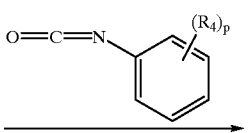

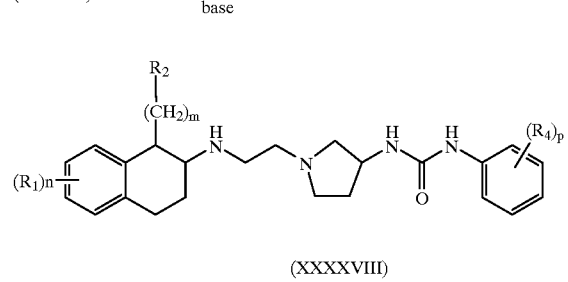

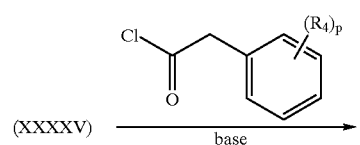

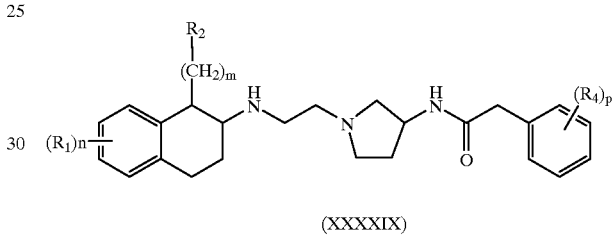

Scheme 23

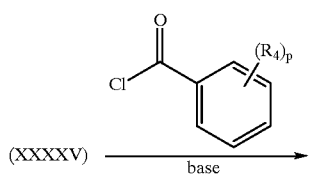

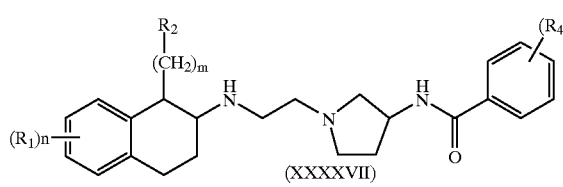

Scheme 24

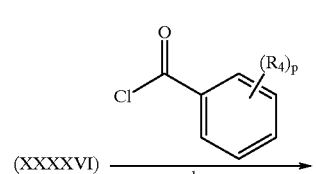

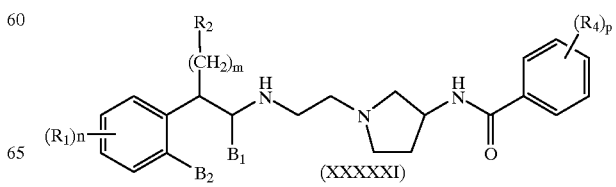

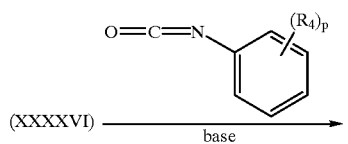

(XXXXVI)

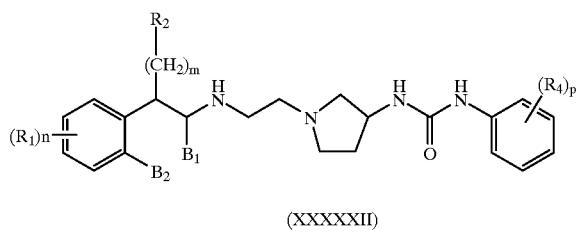

(XXXXXII)

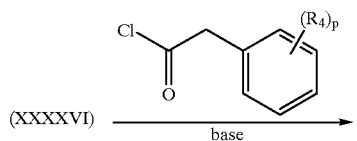

(XXXXVI)

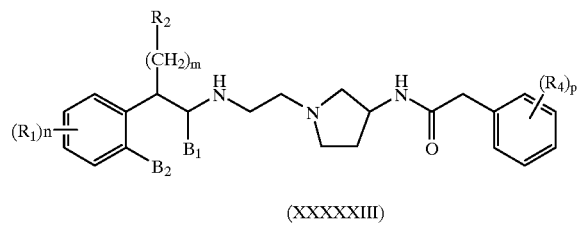

(XXXXXIII)

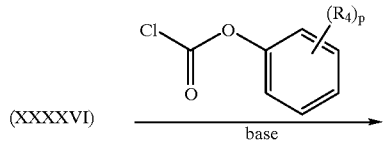

(XXXXVI)

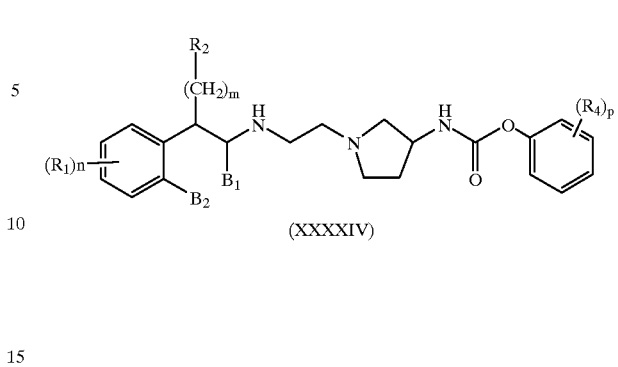

(XXXXIV)

Substituting an appropriately protected aminopiperidine, such as (4-t-butoxycarbonylamino)piperidine for (3-t-butoxycarbonylamino)pyrrolidine in Schemes 17–24 affords compounds of formula A in which L=(N-methylene)piperidin-4-yl, Y=methylene or carbonyl and Z=N-(aryl)sulfonamido, sulfonamido, benzamido, phenylureido, phenylacetamido or (phenoxy)carbonylamino.

Compounds of formula A in which Y=carbonyl, L=(N-methylene)piperidin-4,4-diyl and Z=1-aryl-2,3-dihydro-4-oxo-imidazol-5,5-diyl are prepared by reacting 1-aryl-1,3,8-triazaspiro-[4,5]decan-4-one with a haloacetic acid ester, such as ethyl bromoacetate, in the presence of an amine base, such as diisopropylethylamine, in an inert solvent such as acetonitrile, at a temperature from ambient temperature to reflux, to afford ethyl (1-aryl-1,3,8-triazaspiro-[4,5]decan-4-one-8-yl)acetate. This ester is subjected to hydrolysis under basic conditions, for example, by treatment with sodium hydroxide in an alcoholic solution such as aqueous methanol, to yield upon acidification with an inorganic or organic acid such as hydrochloric or acetic acid for example, (1-aryl-1,3,8-triazaspiro-[4,5]decan-4-one-8-yl)acetic acid. This carboxylic acid is reacted directly with β-tetralins (VII) or phenethylamines (XI), in the presence of a base such as triethylamine for example, under peptide coupling conditions described above, to afford aminotetalinamides (XXXXXV) and phenethylamides (XXXXXVI) respectively, of formula A in which Y=carbonyl, L=(N-methylene)piperidin-4,4-diyl and Z=1-aryl-2,3-dihydro-4-oxo-imidazol-5,5-diyl (Schemes 25–26).

Scheme 25

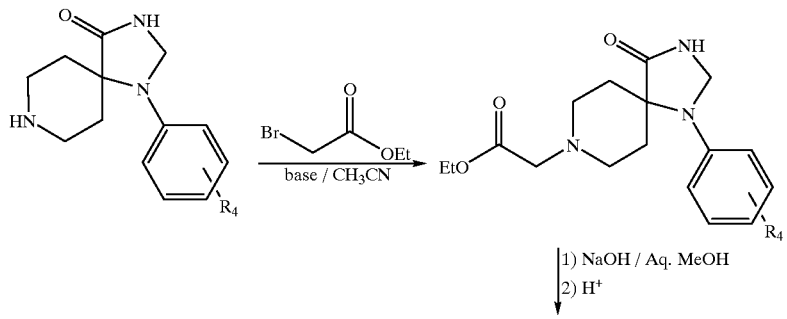

-continued

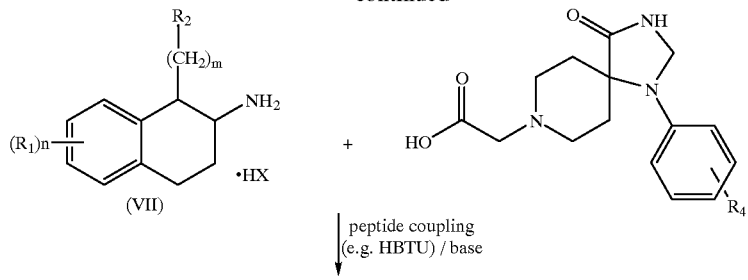

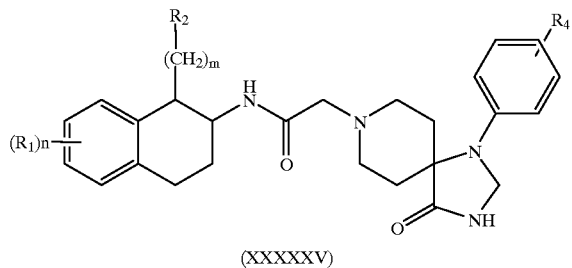

(XXXXXV)

Scheme 26

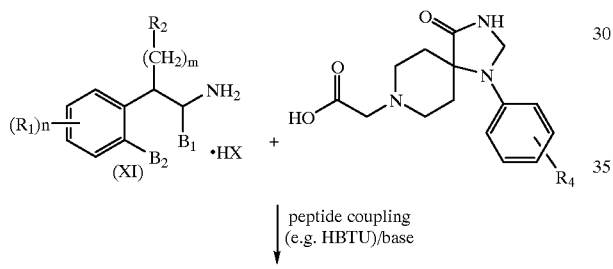

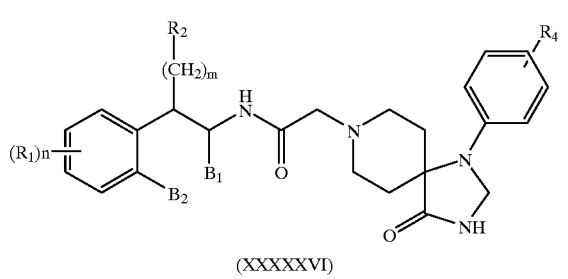

(XXXXXVI)

Compounds of formula A in which L (N-methylene)4-acetyl-piperidin-4-yl and Z=phenyl are prepared by reacting 4-acetyl-4-phenylpiperidine with a haloacetic acid ester, such as, for example, ethyl bromoacetate, in the presence of an amine base, such as diisopropylethylamine, in an inert solvent such as acetonitrile, at a temperature ranging from ambient temperature to reflux, to afford ethyl [(4-acetyl-4-phenylpiperidin-1-yl]acetate. This ester is subjected to hydrolysis under basic conditions, for example, by treatment with sodium hydroxide in an aqueous methanol, to yield, upon acidification with an inorganic or organic acid such as hydrochloric or acetic acid for example, [(4-acetyl-4-phenylpiperidin-1-yl]acetic acid. This carboxylic acid is reacted with β-aminotetralins (Vll) or phenethylamines (XI), in the presence of a base, such as triethylamine for example, under peptide coupling conditions described above, to afford (tetralinamido)arylpiperidines (XXXXXVII) and (phenethylamido)arylpiperidines (XXXXXVIII) respectively, of formula A in which Y=carbonyl, L=(N-methylene)-4-acetyl-piperidin-4-yl and Z=phenyl (Schemes 27–28).

Scheme 27

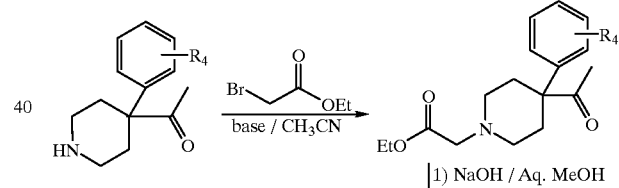

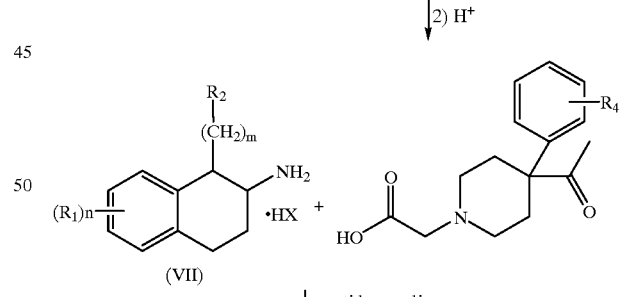

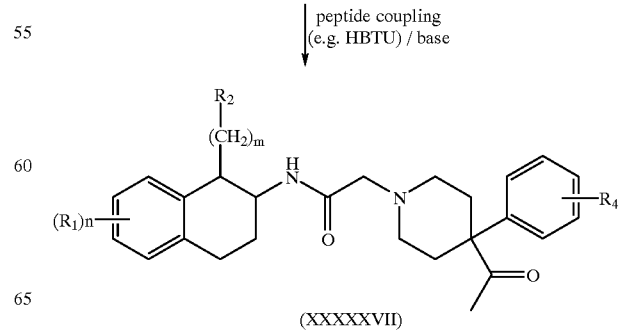

(XXXXXVII)

Scheme 28

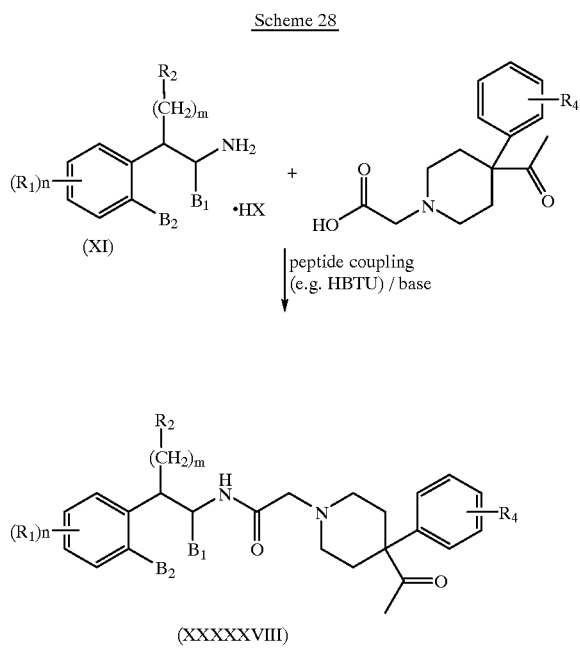

(XI)

(XXXXXVIII)

Other compounds of this invention having the formula A can be prepared using the methods described herein; modifications of the experimental protocols described above are known or obvious or within the ability of those skilled in the art. For example, a variety of β-tetralones are known or readily prepared by reaction of phenylacetic acids with ethylene gas in the presence of a Lewis acid (for example, Stjernlof, P. et. al. *J. Med. Chem.* 1995, 38, 2202); these compounds can be directly converted to aminotetralins (VII) via reductive amination (Scheme 2). Phenethylamine intermediates (XI) are accessible from phenylacetonitriles using literature methods (Jounral, Hawes and Wibberley, *J. Chem. Soc. C.* 1966, 315 and 320; also see *J. Am. Chem. Soc.* 1989, 111, 5954 and *Synthesis* 1997, 11, 1268) and can be used to prepare compounds of formula A in which $B_1$ and $B_2$ are both hydrogen (Scheme 3). Compounds in which the $R_1$ group(s) is varied can be obtained using the chemistry described above; in some cases, protecting group manipulations are used and these are obvious or known to those skilled in the art. Examples include masking an amine group as a carbamate, amide or phthalamide, and masking an hydroxyl group as an ether or ester. Other $R_1$ substituents are available through functional group manipulations such as, for example, reduction of a nitro group to an amine or dehydration of an amide to a nitrile.

Variation of the $R_2$ group is readily accomplished by using substituted benzaldehydes, naphthylaldehydes and heteroaryl carboxaldehydes, or by using alkyl, alkylenic, alkynylic and benzylic halides, or by using phenoxyalkyl and haloalkyl halides in Schemes 1 and 3. Compounds in which the L group is varied, are derived from piperazines, piperidines or pyrrolidines as described in Schemes 6, 10, 14, 17 and 25. Compounds in which L is alkylene, alkenylene, alkynylene, cycloalkylene or cycloalkylalkylene are derived from amino-carboxylic acids such as aminohexanoic acid, aminohexenoic acid, aminohexynoic acid. Compounds in which L is α-aminoalkylene are derived from amino acids such as lysine which can be used in the racemic or enantiomeric form.

Compounds of formula A where Z is sulfonamido or (aryl)sulfonamido, in which either the $R_3$ or the $R_4$ group is varied, are accessible by sulfonylation; there are hundreds of sulfonyl halides or sulfonic acids that are commercially available and more that are known. Compounds of formula A where Z is sulfonamido or (aryl)sulfonamido, in which the $R_3$ substituent is heteroaryl can be prepared by substituting a pyridinyl, thienyl or furyl sulfonylchloride for a benzenesulfonamide as described in Schemes 4–5. Similarly, alkylsulfonyl and cycloalkylsulfonyl halides, alone or in the presence of an activating agent such as a Lewis acid, can be used to prepare sulfonamides of formula A in which the $R_3$ substituent is alkyl or cycloalkyl respectively. Compounds in which Z is phenyl or aryl are obtained directly from arylpiperazines and arylpiperidines as described in Schemes 10 and 14 respectively; hundreds of arylpiperazines and arylpiperidines are known or commercially available and can be used to make compounds of this invention. Compounds of formula A where Z is benzamido, phenylureido, phenylacetamido, (phenoxy)carbonylamino are prepared from aroyl halides, isocyanates, phenylacetyl halides and chloroformates as described in Schemes 20–21 and 23–24 and hundreds of reagents of these kinds are commercially available or known.

Compounds of formula A in which $B_1$ and $B_2$ are joined together to form a five-membered ring (an aminoindane) are prepared starting from an indanone and using the chemistry described herein. It is preferable to use a symmetrical indan-2-one to avoid the formation of regiochemical isomers which are difficult to separate.

EXAMPLES

The following examples describe the invention in greater detail and are intended to illustrate the invention, but not to limit it. All compounds were identified by a variety of methods including nuclear magnetic resonance spectroscopy, mass spectrometry and, in some cases, infrared spectroscopy and elemental analysis. Nuclear magnetic resonance (300 MHz NMR) data are reported in parts per million downfield from tetramethylsilane. Mass spectra data are reported in mass/charge (m/z) units. Unless otherwise noted, the materials used in the examples were obtained from readily available commercial sources or synthesized by standard methods known to those skilled in the art.

Examples 1–2

2-Amino-6-[(2-fluorophenylsulfonyl)amino]-N-[cis-1,2,3,4-tetrahydro-6-methoxy-1-(3-pyridinylmethyl)-2-naphthenyl]-(2S)-hexanamide bis-hydrochloride 7

N-[5-amino-6-[[cis-1,2,3,4-tetrahydro-6-methoxy-1-(3-pyridinylmethyl)-2-naphthalenyl]amino]hexyl]-2-fluorobenzenesulfonamide tris-hydrochloride 8

A. 6-Methoxy-β-tetralone 1 (2.0 g, 11.3 mmol) and diisopropylethylamine (0.20 mL, 1.1 mmol) were dissolved in benzene (60 mL) with stirring in a 100 mL round-bottom flask. 3-Pyridylcarboxaldehyde (1.1 mL, 11.7 mmol) was added and the reaction vessel was flushed with argon and a Dean-Stark trap with reflux condenser was attached. The mixture was heated at reflux for 19 hours. After cooling, HPLC analysis indicated that no products had formed. Piperidine (0.094 mL, 1.1 mmol) was added at this time and heating at reflux was continued for 23 hours. The solvents were removed in vacuo to yield a glassy orange solid. Chromatographic purification [silica gel column (dimensions 5×29 cm) eluting with a gradient of: 100% hexane (400 mL), 75%/25% hexane/ethyl acetate (v/v) (400 mL), 50%/50% hexane/ethyl acetate (v/v) (400 mL), 25%/75% hexane/ethyl acetate (v/v) (400 mL), and finally with 100% ethyl acetate] was performed. After evaporation of the appropriate fractions, 3,4-dihydro-6-methoxy-1-((3-pyridinyl)methylidenyl)-2-naphthalenone 2 (1.484 g, 5.59 mmol) was obtained as an orange oil which solidified upon standing in the refrigerator. MS (MH+) 266; $^1$H NMR (CDCl$_3$) δ 2.67 (t, 2H), 3.02 (t, 2H), 3.83 (s, 3H), 6.60 (dd, 1H), 6.82 (d, 1H), 7.19 (m, 2H), 7.51 (s, 1H), 7.71 (d, 1H), 8.49 (dd, 1H), 8.65 (d, 1H).

B. The naphthalen-2-one 2 (1.442 g, 5.44 mmol) obtained above was dissolved in absolute ethanol (50 mL) and transferred to a 250 mL Parr hydrogenation bottle. Separately, ethanol was carefully added to 10% palladium on carbon (0.020g) and this slurry was added to the Parr bottle. The mixture was hydrogenated under a pressure of 50 psi for 16 hours. The catalyst was removed by filtration over Celite. Spectroscopic evidence indicated the presence of some starting material and so more palladium catalyst (0.081 g) was added to the ethanol solution and the hydrogenation was repeated for 20 hours. The catalyst was then removed by filtration over Celite. Removal of the solvents in vacuo yielded 3,4-dihydro-6-methoxy-1-(3-pyridinylmethyl)-2(1H)-naphthalenone 3 as an orange oil which was used in the next step without further purification. MS (MH+) 268.

C. Naphthalen-2-one 3 obtained above was dissolved in methanol (275 mL) in a 1 L round-bottom flask. Ammonium acetate (4.27 g, 55.4 mmol) was added to the stirred methanol solution and was allowed to completely dissolve before proceeding. Sodium cyanoborohydride (1.703 g, 27.5 mmol) was then added to the methanol solution. The reaction vessel was flushed with nitrogen and the solution refluxed for 18 hours. The solvents were then removed in vacuo to yield a yellow solid which was dissolved in ethyl ether (500 mL) and 0.1 M sodium hydroxide solution (275 mL). The organic layer was removed and washed with an additional 0.1 M sodium hydroxide solution (275 mL) and with water (250 mL). The combined aqueous washes were back extracted with ethyl ether (3×100 mL). The organic extracts were combined and dried over sodium sulfate. The solvents were removed in vacuo and the residue was taken up in ethyl ether and a minimum amount of dichloromethane. An excess of 1 M hydrogen chloride in ethyl ether was added and a dark tan precipitate formed. The solvents were removed in vacuo and the resulting solid was triturated with ether and dried in a vacuum oven to yield 1,2,3,4-tetrahydro-6-methoxy-1-(3-pyridinylmethyl)-2-naphthalenamine bis-hydrochloride 4 as a tan-orange solid (1.208 g, 3.54 mmol) MS (MH+) 269; $^1$H NMR (DMSO-d$_6$) δ 1.95–2.20 (m, 2H), 2.68–3.29 (m, 4H), 3.30–3.48 (m, 2H), 3.69 (s, 3H), 5.98 (d, 1H), 6.41 (dd, 1H), 6.75 (d, 1H), 7.98 (dd, 1H), 8.36 (d, 1H), 8.68–8.89 (m, 5H) (Scheme 28B).

SCHEME 28B

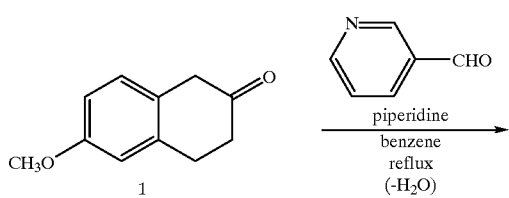

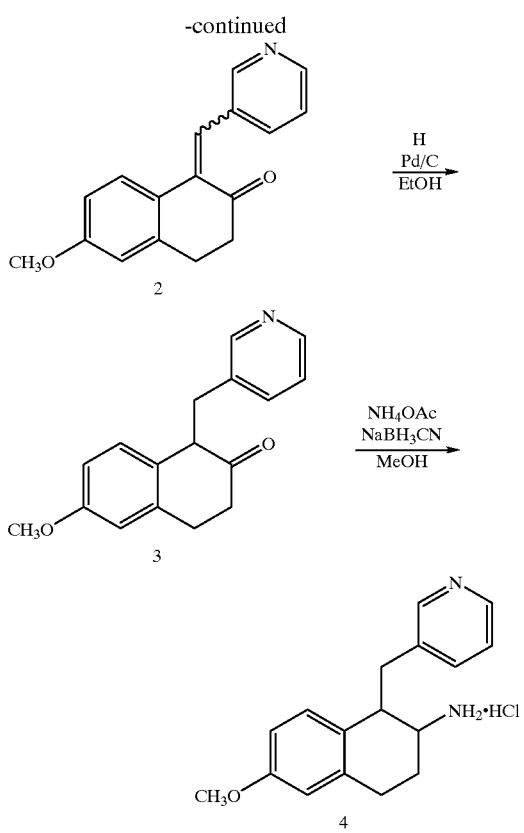

D. N-tert-Butoxycarbonyl-L-Lysine (2.49 g, 10.1 mmol) was placed in a 200 mL round-bottom flask. A magnetic stir bar was added followed by 10 mL dioxane and 21 mL 1 N sodium hydroxide solution. The solution was stirred for several minutes until complete dissolution had occurred. A solution of 2-fluorobenzenesulfonyl chloride (2.00 g, 10.3 mmol) in dioxane (11 mL) was added via pipette. The reaction vessel was flushed with argon, capped and allowed to stir at ambient temperature for approximately 1.5 hours. The stir bar was then removed and the solvent evaporated under reduced pressure until only water remained. To this mixture water was added to bring the volume to about 50 mL and 1N hydrochloric acid (22 mL) was added which resulted in the formation of a gooey precipitate. This mixture was extracted with methylene chloride (3×50 mL) and the combined organics were washed with 1N hydrochloric acid (1×50 mL) and then brine (1×50 mL). The organics were dried over magnesium sulfate, filtered and concentrated in vacuo to yield the sulfonylated N-t-butoxycarbonyl-lysine 5 (3.93 g, 9.7 mmol) as an off-white glassy semi-solid. NMR (d$_6$-DMSO): δ 12.42 (s, 1H), 7.90 (t, 1H), 7.79 (t, 1H), 7.71 (m, 1H), 7.49–7.34 (m, 2H), 7.02 (d, 1H), 3.78 (m, 1H), 2.83 (m, 2H), 1.63–1.16 (m, 15H); MS: M–H=403.

E. The sulfonylated L-lysine 5 from the previous reaction (3.92 g, 9.69 mmol) was placed in a 300 mL round-bottom flask along with 1,2,3,4-tetrahydro-6-methoxy-1-(3-pyridinylmethyl)-2-naphthalenamine bis-hydrochloride 4 (3.53 g, 10.34 mmol) and a stir bar. N,N-Dimethylformamide (DMF) (50 mL) was added followed by diisopropylethylamine (5.6 mL, 32.1 mmol) and the mixture was stirred. After dissolution, 2-(1H-benzotriazole-1-yl)-1,1,3,3-tetramethyluronium hexafluorophosphate (HBTU) (3.72 g, 9.81 mmol) was added and the flask was flushed with argon, capped and allowed to stir at ambient temperature for 30 minutes. Water (~5 mL) was then added to quench the reaction and the solvents were removed in vacuo to give a brown oil. This material was purified by column chromatography on a silica gel column (dimensions 6×12 cm) eluting with a gradient of methylene chloride-acetone-methanol. After evaporation of the appropriate fractions, adduct 6 (as a tan-green foam, 4.63 g, 7.07 mmol) was obtained as a mixture of diastereomers. MS: MH+=655.

F. The sulfonylated lysino-tetralinamide 6 from the previous reaction (4.59 g, 7.01 mmol) was placed in a 200 mL round-bottom flask with a stir bar and methylene chloride (100 mL) was added. With stirring, a solution of 95% TFA/5% $H_2O$ (v/v) (10 mL) was added and the reaction mixture was allowed to stir under nitrogen at ambient temperature for 3.5 hours. The reaction mixture was then concentrated in vacuo and the residue was triturated with diethyl ether. The liquid was decanted and more ether was added. The resultant solid was filtered and dried under vacuum to give the desired tetralinamide lysino-sulfonamide bis-hydrochloride 7 (4.28 g, 5.47 mmol) as a mixture of diastereomers. A portion of this material (4.01 g) was separated into racemic sets of diastereomers via reverse-phase chromatography (Bondapak C18, 6×(40×100 mm) column using a gradient of $H_2O/CH_3CN$ (+0.1% TFA)). The appropriate fractions were isolated and lyophilized to yield diastereomer a (2.17 g, 2.77 mmol) and diasteromers b (1.78 g, 2.27 mmol) as bis-TFA salts (absolute configurations of the diastereomers were not determined). Diastereomer a: de=96%; NMR($d_6$-DMSO): δ 8.57 (m, 2H), 8.30 (s, 1H), 8.11 (br, 3H), 7.96 (t, 1H), 7.80–7.64 (m, 3H), 7.55 (dd, 1H), 7.48–7.32 (m, 2H), 6.7 (s, 1H), 6.58–6.46 (m, 2H), 4.03 (m, 1H), 3.79 (m, 1H), 3.69 (s, 3H), 3.24 (m, 1H), 3.03–2.73 (m, 6H), 2.08–1.91 (m, 1H), 1.85–1.58 (m, 3H), 1.53–1.31 (m, 4H); MS: MH+=555. Diastereomer b: de=100%; NMR($d_6$-DMSO): δ 8.68 (d, 1H), 8.57 (d, 1H), 8.49 (s, 1H), 8.21 (br, 3H), 8.01 (d, 1H), 7.93 (t, 1H), 7.78 (dt, 1H), 7.73 (m, 2H), 7.52–7.37 (m, 2H), 6.75 (s, 1H), 6.56 (m, 2H), 3.99 (m, 1H), 3.85 (m, 1H), 3.71 (s, 3H), 3.23 (m, 1H), 3.08–2.76 (m, 6H), 2.00–1.59 (m, 4H), 1.53–1.22 (m, 4H); MS: MH+=555 (Scheme 29).

G. Diastereomer a 7 from the previous reaction (2.02 g, 2.58 mmol) was placed in a 200 mL round-bottom flask along with a stir bar and THF (60 mL) was added. After stirring, a solution of borane in THF (40 mL of a 1M solution, 40 mmol) was added and the flask was flushed with nitrogen and a reflux condenser was attached. The mixture was heated at reflux for 24 hours at which time an additional portion of the borane solution (10 mL) was added. The reaction mixture was heated at reflux for an additional 14 hours. The reaction mixture was allowed to cool and water (10 mL) was carefully added to quench the reaction. Hydrochloric acid (20 mL of a 1N solution) was added and the reaction mixture was heated at reflux for 2 hours. The solvents were removed in vacuo and the residue was suspended in water (250 mL). This mixture was made slightly acidic via the addition of 1N hydrochloric acid. This aqueous solution was washed with methylene chloride (3×250 mL) and the aqueous layer was separated. Ammonium hydroxide solution was added until the pH was basic. The water was then removed in vacuo giving a white solid. The resultant material was triturated with methylene chloride and the borane salts that precipitated were removed by filtration. The remaining organics were concentrated in vacuo to give the crude product as a foam. This material was purified by flash chromatography on a silica gel column (dimensions 6×11 cm) eluting with a gradient of methylene chloride-methanol-ammonium hydroxide. After evaporation of the appropriate fractions, the residue was treated with an excess of ethanolic-hydrogen chloride, followed by evaporation and drying under vacuum, to obtain aminotetralin sulfonamide 8 as a yellow tris-hydrochloride salt (0.898 g, 1.38 mmol). NMR($d_6$-DMSO): δ 10.83 (br, 1H), 10.08 (br, 1H), 8.80 (d, 1H), 8.73 (m, 4H), 8.43 (d, 1H), 7.97 (m, 2H), 7.81 (t, 1H), 7.71 (m, 1H), 7.51–7.33 (m, 2H), 6.75 (s, 1H), 6.37 (d, 1H), 5.83 (d, 1H), 3.80 (m, 1H), 3.71–3.30 (m, 8H), 3.11 (m, 1H), 2.98–2.69 (m, 4H), 2.34–2.13 (m, 2H), 1.73–1.55 (m, 2H), 1.54–1.29 (m, 4H); MS: MH+=541 (Scheme 29).

Scheme 29

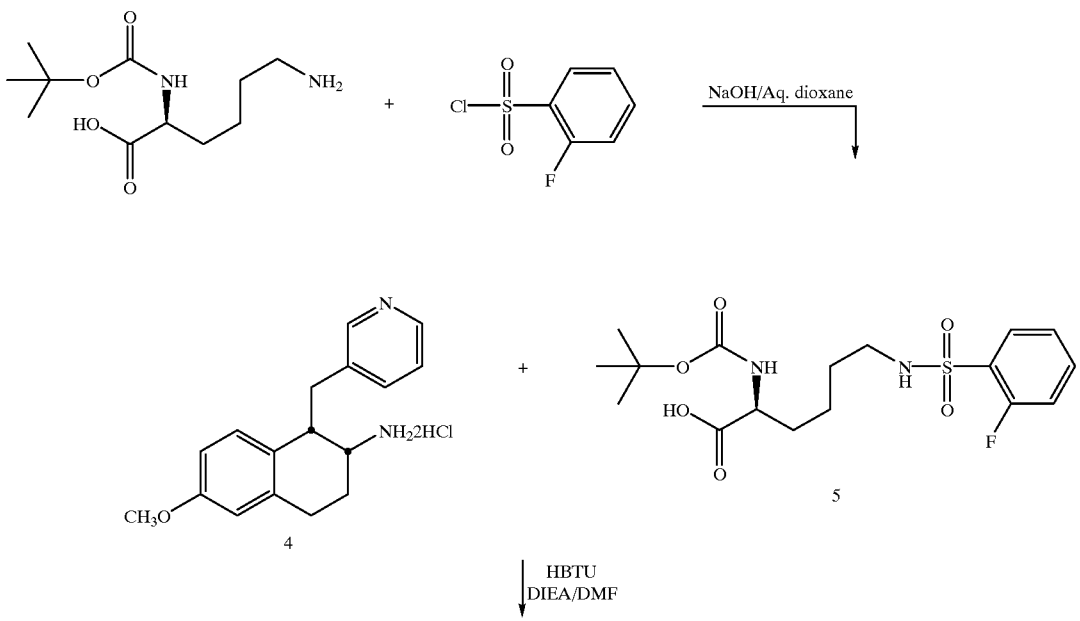

-continued

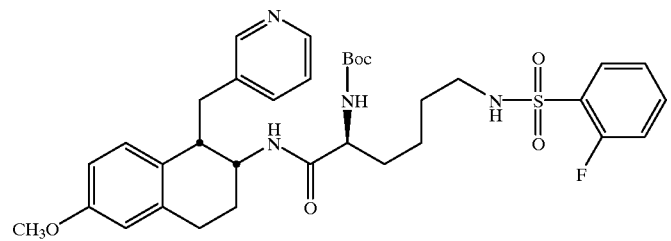

6

1) TFA—H₂O
2) HCl

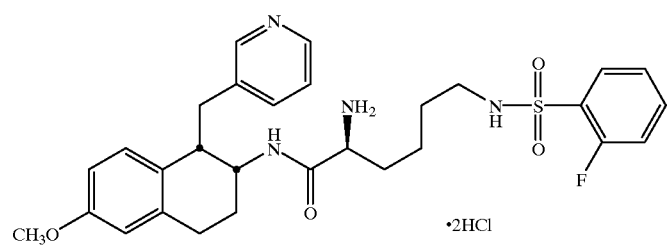

7 •2HCl

1) BH₃—THF
2) HCl

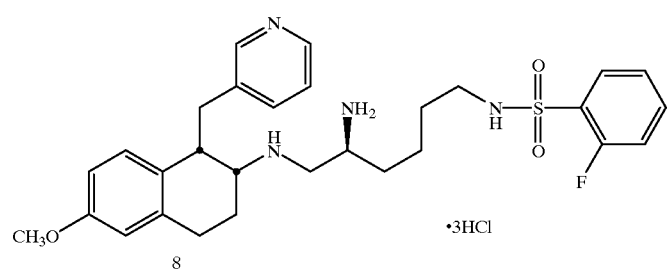

8 •3HCl

Example 3

N-[5-amino-6-[[cis-1,2,3,4-tetrahydro-6-hydroxy-1-(3-pyridinylmethyl)-2-naphthalenyl]amino]hexyl]-2-fluorobenzenesulfonamide tris-hydrochloride 9

Aminotetralin sulfonamide 8 from the previous reaction (0.160 g, 0.246 mmol) was placed in a 50 mL round-bottom flask along with a stir bar. Methylene chloride (25 mL) was added and the slurry was cooled on an ice bath for several minutes. Boron tribromide in methylene chloride (1M, 1.25 mL, 1.25 mmol) was added to the reaction. The flask was flushed with argon, capped and allowed to warm up to ambient temperature and the mixture was stirred over 16 hours at which time the reaction was quenched by the addition of methanol (1 mL). The solvents were removed in vacuo and an additional aliquot of methanol was added to the resultant residue. Evaporation of the solvent from this mixture afforded crude product which was purified via reverse-phase chromatography (Bondapak C18, 3×(40×100 mm), gradient of H₂O/CH₃CN (+0.1% TFA)). The appropriate fractions were collected and lyophilized. The resultant material was subsequently treated with ethanolic-hydrogen chloride, followed by evaporation and drying under vacuum to give the phenolic product 9 as a white tris-hydrochloride salt (0.145 g, 0.228 mmol). NMR(d₆-DMSO): δ 10.77 (br, 1H), 10.01 (br, 1H), 9.31 (br, 1H), 8.79 (d, 1H), 8.67 (m, 4H), 8.37 (d, 1H), 7.97 (m, 2H), 7.81 (dt, 1H), 7.72 (m, 1H), 7.52–7.36 (m, 2H), 6.57 (s, 1H), 6.22 (dd, 1H), 5.69 (d, 1H), 3.79 (m, 1H), 3.68–3.30 (m, 5H), 3.04 (m, 1H), 2.92–2.68 (m, 4H), 2.33–2.10 (m, 2H), 1.73–1.56 (m, 2H), 1.55–1.32 (m, 4H); MS: MH+=527 (Scheme 30).

Scheme 30

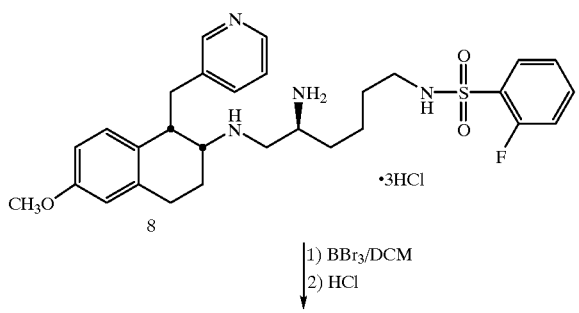

8 •3HCl

1) BBr₃/DCM
2) HCl

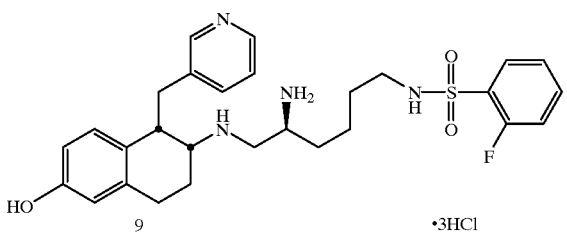

Example 4

(2S)-2-(Acetylamino)-6-[(2-fluorophenylsulfonyl) amino]-N-[cis-1,2,3,4-tetrahydro-6-methoxy-1-(3-pyridinylmethyl)-2-naphthenyl]hexanamide bis-hydrochloride 10

Diasteromerically mixed tetralinamide lysinosulfonamide 7 (0.195 g, 0.249 mmol) was placed into a 50 mL round-bottom flask along with a stir bar. Acetonitrile (25 mL) was added followed by triethylamine (0.122 mL, 0.875 mmol). With stirring, acetyl chloride (0.021 mL, 0.295 mmol) was added and the flask was flushed with argon, capped and stirred overnight at ambient temperature. The solvents were removed in vacuo and the residue was taken up in methylene chloride (75 mL). This mixture was washed with 1N sodium hydroxide (2×25 mL) and then with brine (1×25 mL). The organics were dried over magnesium sulfate, filtered and concentrated in vacuo to give the acetate product 10 as a tan solid (0.139 g, 0.233 mmol) as a 1:1 diastereomeric mixture. NMR(CDCl$_3$): δ 8.52 (d, 0.5H), 8.43 (d, 0.5H), 8.28 (d, 1H), 7.89 (m, 1H), 7.57 (m, 1H), 7.44 (d, 0.5H), 7.39–7.13 (m, 3.5H), 6.92 (t, 0.5H), 6.77 (d, 0.5H), 6.70–6.54 (m, 3H), 6.48 (dd, 1H), 6.34 (d, 0.5H), 5.59 (t, 0.5H), 4.40–4.06 (m, 2H), 3.78 (d, 3H), 3.29 (m, 1H), 3.19–2.82 (m, 6H), 2.02 (d, 3H), 1.92–1.71 (m, 2H), 1.72–1.32 (m, 6H); MS: MH+=597 (Scheme 31).

Example 5

(2S)-2-(Acetylamino)-6-[(2-fluorophenylsulfonyl) amino]-N-[cis-1,2,3,4-tetrahydro-6-hydroxy-1-(3-pyridinylmethyl)-2-naphthenyl]hexanamide bis-hydrochloride 11

The bis-amide 10 from the previous reaction (0.114 g, 0.191 mmol) was placed in a 50 mL round-bottom flask along with a stir bar. Methylene chloride (20 mL) was added and the solution was cooled on an ice bath for several minutes. Boron tribromide in methylene chloride (1 M, 1.0 mL, 1.0 mmol) was added to the reaction mixture. The flask was flushed with argon, capped and allowed to warm up to ambient temperature and the mixture was stirred over 16 hours at which time the reaction was quenched by the addition of methanol (1 mL). The solvents were removed in vacuo and the resultant material treated with an additional aliquot of methanol. This mixture was evaporated in vacuo to yield crude phenolic tetralinamide 11 which was purified via reverse-phase column chromatography which allowed for separation and purification of the racemic pairs of diastereomers (Bondapak C18, 3×(40×100 mm), gradient of H$_2$O/CH$_3$CN (+0.1% TFA)). After lyophilization of the appropriate fractions, each diastereomer was treated with ethanolic-hydrogen chloride, subjected to evaporation and lastly dried under vacuum to give the individual racemic diastereomers as tan hydrochloride salts; diastereomer a (0.036 g, 0.058 mmol) and diastereomer b (0.057 g, 0.092 mmol) (absolute configurations of the diastereomers were not determined). Diastereomer a: de=100%; NMR(d$_6$-DMSO): δ 9.22 (v. br, 1H), 8.79 (d, 1H), 8.48 (s, 1H), 8.20 (d, 1H), 8.08–7.87 (m, 4H), 7.83–7.63 (m, 2H), 7.50–7.33 (m, 2H), 6.54 (s, 1H), 6.43–6.28 (m, 2H), 4.19 (q, 1H), 3.93 (m, 1H), 3.18 (m, 1H), 3.08–2.67 (m, 6H), 1.92 (m, 1H), 1.84 (s, 3H), 1.73 (m, 1H), 1.58–1.16 (m, 6H); MS: MH+=583. Diastereomer b: de=66%; NMR(d$_6$-DMSO): δ 9.20 (v. br, 1H), 8.77 (d, 1H), 8.57 (s, 1H), 8.28–8.14 (m, 2H), 8.08–7.84 (m, 3H), 7.83–7.62 (m, 2H), 7.50–7.32 (m, 2H), 6.54 (s, 1H), 6.47–6.29 (m, 2H), 4.10 (q, 1H), 3.85 (m, 1H), 3.27–3.08 (m, 2H), 3.03–2.66 (m, 5H), 1.90 (s, 3H), 1.87–1.63 (m, 2H), 1.57–1.13 (m, 6H); MS: MH+=583 (Scheme 31).

Scheme 31

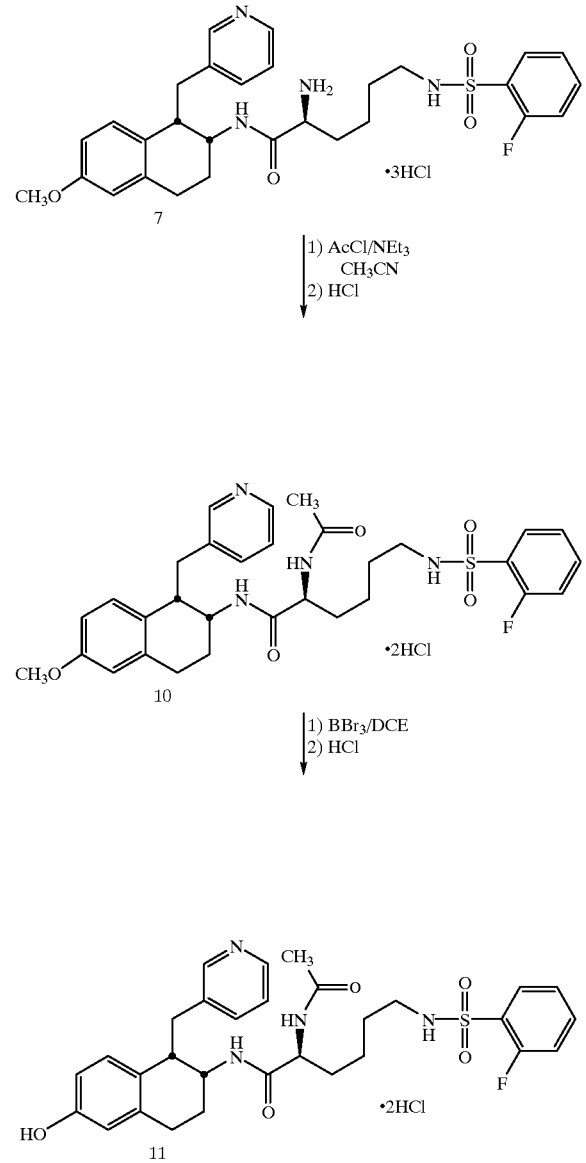

Example 6

3-[(Phenylsulfonyl)amino]-N-[cis-1,2,3,4-tetrahydro-6-fluoro-1-(3-pyridinylmethyl)-2-naphthalenyl]-1-pyrrolidineacetamide bis-trifluoroacetate 17

A. Racemic 3-(N-butoxycarbonyl)aminopyrrolidine (5.13 g, 27.5 mmol) was placed into a 300 mL round-bottom flask along with a stir bar. Acetonitrile (100 mL) was added which gave a slurry to which was added diisopropylethylamine (7.2 mL, 41.3 mmol) followed by ethyl bromoacetate (3.1 mL, 28.0 mmol). The flask was flushed with nitrogen and a reflux condenser was attached. The reaction mixture was heated at reflux for 1.5 hours then allowed to cool and stir at ambient temperature overnight. The solvents were removed in vacuo to give an oily solid. This material was taken up in methylene chloride (200 mL) and washed successively with sodium bicarbonate solution (1×200 mL), water (1×200 mL) and brine (200 mL). The organics were dried over magnesium sulfate, filtered and the solvents removed in vacuo to give a thick oil which slowly crystallized upon standing to give the pyrrolidinylacetate ester 12 (6.96 g, 25.6 mmol). NMR(CDCl$_3$): δ 4.98 (br d, 1H), 4.27–4.13 (m, 3H), 3.33 (s, 2H), 2.98 (m, 1H), 2.83–2.66 (m, 2H), 2.48 (m, 1H), 2.27 (m, 1H), 1.67 (m, 1H), 1.44 (s, 9H), 1.28 (t, 3H).

B. Pyrrolidinylacetate ester 12 from the previous reaction (6.95 g, 25.5 mmol) was put into a 300 mL round-bottom flask. A stir bar and methanol (100 mL) was added. The mixture was stirred until all of the starting material had dissolved. Sodium hydroxide solution (1N, 75.0 mL, 75.0 mmol) was added to the resulting solution. The reaction vessel was capped and the mixture was allowed to stir for 20 hours at which time hydrochloric acid was added (1N, 75.0 mL, 75.0 mmol). The resultant mixture was allowed to stir for several minutes. The solvents were removed in vacuo and the resulting solid was treated with methylene chloride. The organic extract was dried over magnesium sulfate, filtered and concentrated in vacuo to give pyrrolidinylacetic acid 13 as a white powder (6.30 g, 25.8 mmol). NMR(d$_6$-DMSO): δ 7.21 (br d, 1H), 4.05 (m, 1H), 3.38 (s, 2H), 3.23 (m, 1H), 3.02 (m, 2H), 2.78 (m, 1H), 2.12 (m, 1H), 1.73 (m, 1H), 1.39 (s, 9H); MS: MH+=245.

C. 1,2,3,4-Tetrahydro-6-fluoro-1-(3-pyridinylmethyl)-2-naphthalenamine bis-hydrochloride 14 (0.331 g, 1.01 mmol), prepared from 6-fluoro-β-tetralone using the chemistry described in EXAMPLE 1 (FIG. 1), was placed in a 25 mL round-bottom flask along with a stir bar and DMF (5 mL) was added. The pyrrolidinylacetic acid 13 (0.250 g, 1.02 mmol) from the previous reaction was added followed by diisopropylethylamine (0.580 mL, 3.33 mmol) and then HBTU (0.387 g, 1.02 mmol). The flask was flushed with argon, capped and allowed to stir at ambient temperature for 2 hours. The reaction was diluted with brine (50 mL) and methylene chloride (150 mL) and the layers separated. The organics were washed with more brine (2×50 mL). The combined aqueous brine washes were extracted with methylene chloride (2×25 mL) and the combined organics were dried over magnesium sulfate, filtered and concentrated in vacuo to give the crude product. This material was purified via reverse-phase column chromatography (Bondapak C18, 3×(40×100 mm), gradient of H$_2$O/CH$_3$CN (+0.1% TFA)). Lyophilization of the appropriate fractions gave the pyrrolidineacetamide bis-TFA salt 15 as a white powder (0.251 g, 0.35 mmol); MS: MH+=483.

D. Pyrrolidineacetamide 15 from the previous reaction (0.205 g, 0.288 mmol) was placed in a 50 mL round-bottom flask along with a stir bar. Methylene chloride (25 mL) was added followed by a small amount of water (~0.5 mL) and TFA (2 mL). The reaction was capped and allowed to stir at ambient temperature for 19 hours at which time the solvents were removed in vacuo to yield 3-aminopyrrolidineacetamide tris-TFA salt 16 (0.204 g, 0.282 mmol). NMR(d$_6$-DMSO): δ 8.69 (d, 1H), 8.64 (d, 1H), 8.49 (s, 1H), 8.36 (br, 3H), 7.93 (d, 1H), 7.67 (t, 1H), 7.02 (d, 1H), 6.83 (m, 2H), 4.13 (s, 2H), 4.07–3.88 (m, 3H), 3.87–3.22 (m, 4H), 3.15–2.69 (m, 4H), 2.41 (m, 1H), 2.14–1.6 (m, 3H); MS: MH+=383.

E. Aminopyrrolidine acetamide 16 from the previous reaction (0.074 g, 0.102 mmol) was placed into a 50 mL round-bottom flask along with a stir bar and acetonitrile (20 mL) was added. Diisopropylethylamine (0.078 mL, 0.448 mmol) was added followed by benzenesulfonyl chloride (0.013 mL, 0.102 mmol). The flask was flushed with argon, capped and allowed to stir at ambient temperature for 3 hours at which time the solvents were removed in vacuo. The residue was purified by reverse-phase column chromatography (H$_2$O/CH$_3$CN (+0.1% TFA)). After isolation and lyophilization of the appropriate fractions, 3-[(phenylsulfonyl)amino]-N-[cis-1,2,3,4-tetrahydro-6-fluoro-1-(3-pyridinylmethyl)-2-naphthalenyl]-1-pyrrolidineacetamide bis-TFA salt 17 was obtained as a white solid (0.067 g, 0.089 mmol). NMR(d$_6$-DMSO): δ 8.62 (d, 2H), 8.47 (s, 1H), 8.25 (m, 1H), 7.92 (d, 1H), 7.83 (m, 2H), 7.66 (m, 4H), 7.02 (d, 1H), 6.84 (m, 2H), 4.18–3.73 (m, 4H), 3.72–2.72 (m, 9H), 2.07 (m, 1H), 1.98–1.67 (m, 3H); MS: MH+=523 (Scheme 32).

Scheme 32

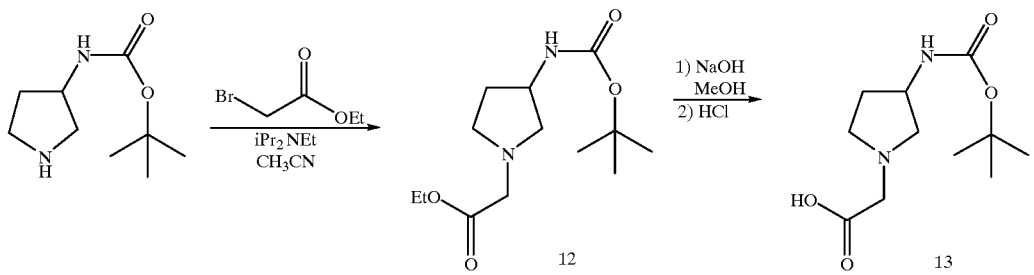

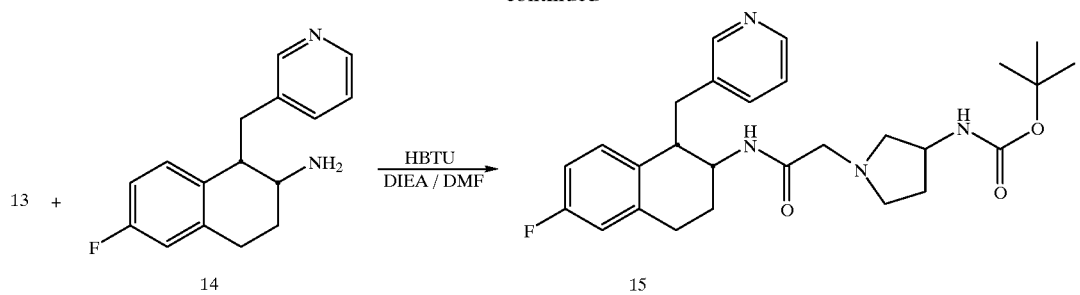

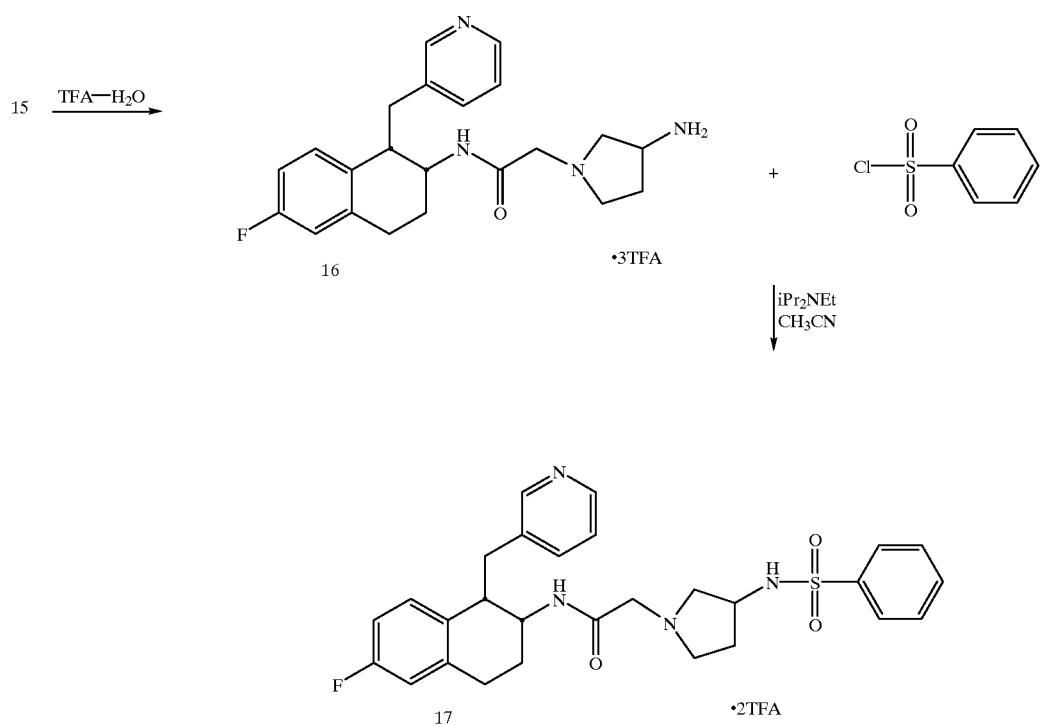

Examples 7–8

4-(2,3-Dihydro-2-oxo-1H-benzimidazol-1-yl)-N-[cis-1,2,3,4-tetrahydro-6-methoxy-1-(3-pyridinylmethyl)-2-naphthalenyl]-1-piperidineacetamide bis-hydrochloride 19

4-(2,3-Dihydro-2-oxo-1H-benzimidazol-1-yl)-N-[trans-1,2,3,4-tetrahydro-6-methoxy-1-(3-pyridinylmethyl)-2-naphthalenyl]-1-piperidineacetamide bis-hydrochloride 20

A solution of 2-(1H-benzotriazole-1-yl)-1,1,3,3-tetramethyluronium hexafluorophosphate (HBTU) (0.974 g, 2.57 mmol), 4-(2,3-dihydro-2-oxo-1H-benzimidazol-1-yl)-1-piperidineacetic acid (1.20 g, 2.57 mmol), and N,N-diisopropylethylamine (1.8 mL, 10.3 mmol) in N,N-dimethylformamide (15 mL) was stirred at room temperature for 5 min. To this mixture, 1,2,3,4-tetrahydro-6-methoxy-1-(3-pyridinylmethyl)-2-naphthalenamine bis-hydrochloride 4 (0.80 g, 2.34 mmol) was added and stirring was continued for 18 h. The solution was heated to 100° C. for 1 h. The solution was cooled and poured into a saturated solution of aqueous sodium bicarbonate. A fine green precipitate was collected by filtration, and the solid was purified by reverse phase $C_{18}$ HPLC eluted with a gradient of water/acetonitrile/trifluoroacetic acid 10/90/0.1 to 90/10/0.1. The cis product 19 was isolated as a colorless solid (0.386 g 22%): $^1$H NMR (DMSO-$d_6$) δ 1.76 (m, 4 H), 2.72–3.02 (m, 4 H), 3.16 (d, 2 H), 3.29–3.46 (m, 3 H), 3.54–3.75 (m, 2 H) superimposed on 3.72 (s, 3 H), 3.92–4.07 (m, 3 H), 4.53–4.65 (m, 1 H), 6.63 (d, 1 H), 6.70–6.77 (m, 2 H), 7.04 (br s, 3 H), 7.59 (br s, 1 H), 7.99 (t, 1 H), 8.37 (d, 1 H), 8.74 (m, 2 H), 8.96 (d, 1 H), 10.5–10.71 (br s, 1 H), and 11.03 (s, 1 H); MS m/e 512 (MH$^+$). A mixture of cis/trans isomers ~8/2 0.490 g (28%) was also obtained as well as the purified trans isomer 20 as a colorless solid (0.136 g, 8%): $^1$HNMR (DMSO-$d_6$) δ 1.70 (m, 6 H), 2.63–3.81 (m, 9 H) superimposed on 3.72 (s, 3 H), 3.83–4.00 (m, 3 H), 4.47–4.60 m, 1 H), 6.67–6.82 (m, 3 H), 7.02 (br s, 3 H), 7.21 (d, 1 H), 7.70 (t, 1 H), 8.14 (d, 1 H), 8.50–8.73 (m, 3 H), 9.70–10.10 (brs, 1 H), and 11.0 (s, 1 H);); MS m/e 512 (MH$^+$) (Scheme 33).

Scheme 33

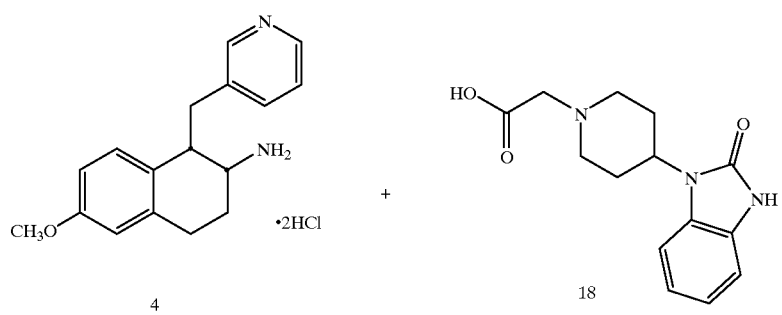

↓ HBTU
DIEA / DMF

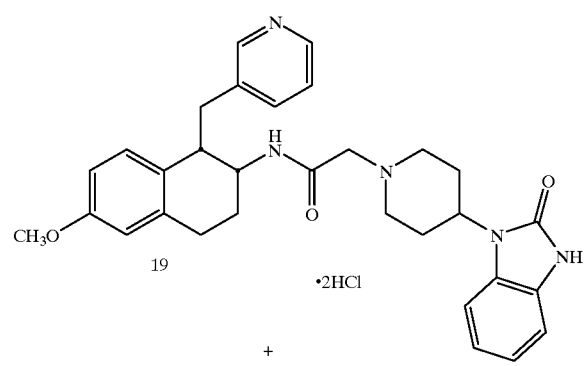

+

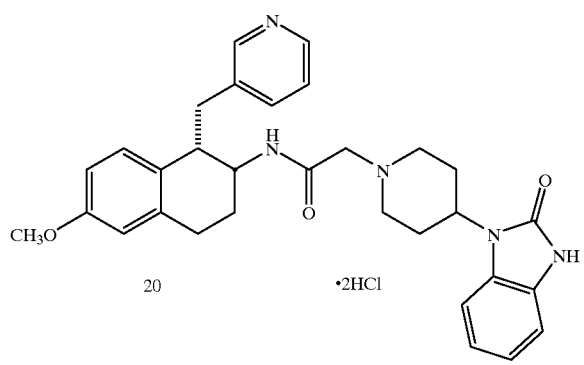

Example 9

4-Acetyl-4-phenyl-N-[cis-1,2,3,4-tetrahydro-1-(3-pyridinylmethyl)-2-naphthalenyl]-1-piperidineacetamide bis-hydrochloride 21

1,2,3,4-Tetrahydro-1-(3-pyridinylmethyl)-2-naphthalenamine bis-hydrochloride 4 (0.75 g, 2.41 mmol) was reacted with 2-(4-acetyl-4-phenyl-piperidin-1-yl)acetic acid (0.86 g, 2.65 mmol), N,N-diisopropylethylamine (2.0 mL, 11.3 mmol) and HBTU (1.01 g, 2.65 mmol) in N,N-dimethylformamide (15 mL) at room temperature for 2 h as described above in EXAMPLES 7–8. The product was collected by filtration from the aqueous work-up. This material was dissolved in isopropanol (~30 mL) and treated with a saturated solution of hydrochloric acid in isopropanol (~5 mL). The solvent was evaporated in vacuo, and the residue was triturated with diethyl ether to give 4-acetyl-4-phenyl-N-[cis-1,2,3,4-tetrahydro-1-(3-pyridinylmethyl)-2-naphthalenyl]-1-piperidineacetamide bis-hydrochloride 21 as an amorphous pale yellow solid (1.2 g, 90%): MS m/e 482 (MH$^+$) (Scheme 34).

Scheme 34

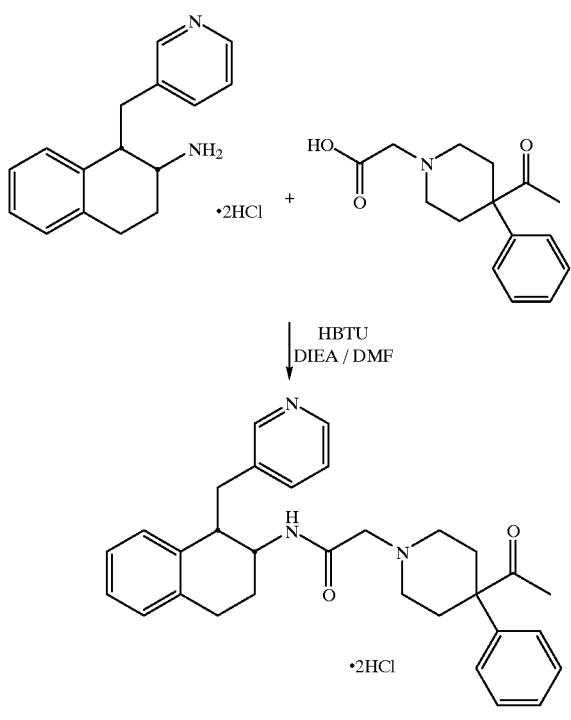

Example 10

4-Oxo-1-phenyl-N-[cis-1,2,3,4-tetrahydro-1-(3-pyridinylmethyl)-2-naphthalenyl]-1,3,8-triazaspiro[4.5]decane-8-acetamide bis-hydrochloride 22

1,2,3,4-Tetrahydro-1-(3-pyridinylmethyl)-2-naphthalenamine bis-hydrochloride 4 (0.75 g, 2.41 mmol) was reacted with 2-(1-phenyl-1,3,8-triazaspiro[4.5]decan-4-one)acetic acid (1.12 g, 2.41 mmol), N,N-diisopropylethylamine (1.68 mL, 9.63 mmol). mmol) and HBTU (0.91 g, 2.41 mmol) in N,N-dimethylformamide (15 mL) at room temperature for 4 h as described above in EXAMPLES 7–8. The product was collected by filtration from the aqueous work up. This material was dissolved in methanol (~30 mL), and treated with concentrated hydrochloric acid (~5 mL). The solvent was evaporated in vacuo, and the residue was triturated with diethyl ether to give 4-oxo-1-phenyl-N-[cis-1,2,3,4-tetrahydro-1-(3-pyridinylmethyl)-2-naphthalenyl]-1,3,8-triazaspiro[4.5]decane-8-acetamide bis-hydrochloride 22 as an amorphous tan solid (1 g, 81%): 1H NMR(DMSO-$d_6$) δ 1.93 (s, 4 H), 2.80–3.08 (m, 4 H), 3.18–3.30 (m, 2 H), 3.38–3.66 (m, 3 H), 3.70–3.89 (m, 2 H), 3.94–4.13 (m, 3 H), 4.65 (s, 2 H), 6.80 (t, 2 H), 7.00–7.29 (m, 8 H), 8.03 (t, 1 H), 8.44 (d, 1 H), 8.81 (br s, 2 H), 8.97 (d, 1 H), 9.16 (s, 1 H), 10.83 (br s, 1 H); MS m/e 510 (MH$^+$) (Scheme 35).

Scheme 35

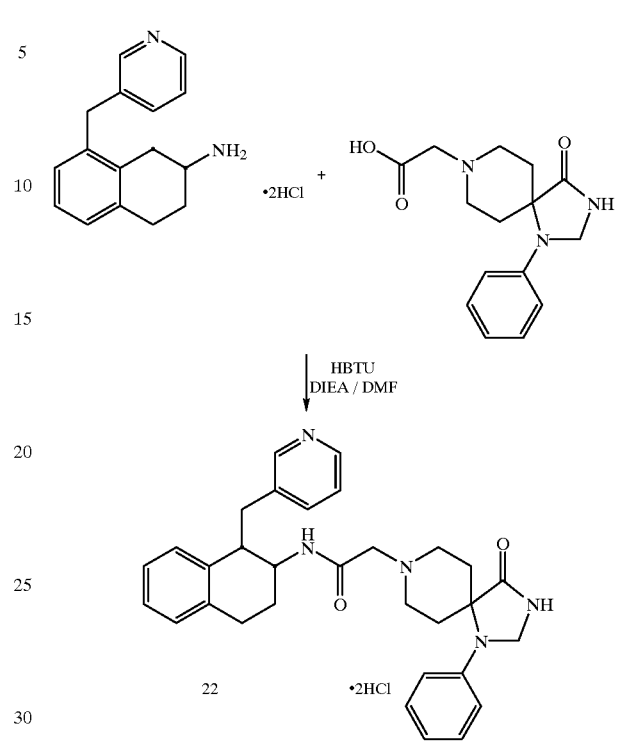

Example 11

4-(2,3-Dihydro-2-oxo-1H-benzimidazol-1-yl)-N-[cis-1,2,3,4-tetrahydro-6-hydroxy-1-(3-pyridinylmethyl)-2-naphthalenyl]-1-piperidineacetamide bis-hydrochloride 23

A solution of 4-(2,3-dihydro-2-oxo-1H-benzimidazol-1-yl)-N-[cis-1,2,3,4-tetrahydro-6-methoxy-1-(3-pyridinylmethyl)-2-naphthalenyl]-1-piperidineacetamide 19 (0.28 g, 0.37 mmol) in dichloromethane (2 mL) was added dropwise to a solution of boron tribromide (1.8 mmol) in dichloromethane (22 mL) at 0° C. After stirring the resultant solution at 0° C. for 1.5 h, methanol (~2 mL) was added and stirring was continued at 0° C. for an additional 0.5 h. The solvent was evaporated in vacuo, and the residue was purified by reverse phase $C_{18}$ HPLC using a water/acetonitrile/TFA gradient, 90/10/0.1 to 10/90/0.1, as the eluant. The product was dissolved in methanol and treated with ethanolic hydrochloric acid. The solvent was evaporated and the process repeated twice to give 4-(2,3-dihydro-2-oxo-1H-benzimidazol-1-yl)-N-[cis-1,2,3,4-tetrahydro-6-hydroxy-1-(3-pyridinylmethyl)-2-naphthalenyl]-1-piperidineacetamide bis-hydrochloride salt 23 (0.148, 68%) as a colorless solid: 1H NMR(DMSO-$d_6$) δ 1.73–2.03 (m, 4 H), 2.70–2.94 (m, 4 H), 3.05–3.20 (br s, 2 H), 3.27–3.47 (m, 3 H), 3.55–3.76 (m, 2 H), 3.92–4.15 (m, 3 H), 4.54–4.67 (m, 1H), 6.46 (d, 1H), 6.58 (s, 2 H), 7.05 (m, s, 3 H), 7.60 (br s, 1 H), 7.94 (t, 1 H), 8.30 (d, 1 H), 8.72–8.83 (m, 2 H), 8.96 (d, 1 H), 9.30 (br s, 1 H), 10.64 (br s, 1 H), and 11.05 (s, 1 H); MS m/e 512 (MH$^+$) (Scheme 36).

Scheme 36

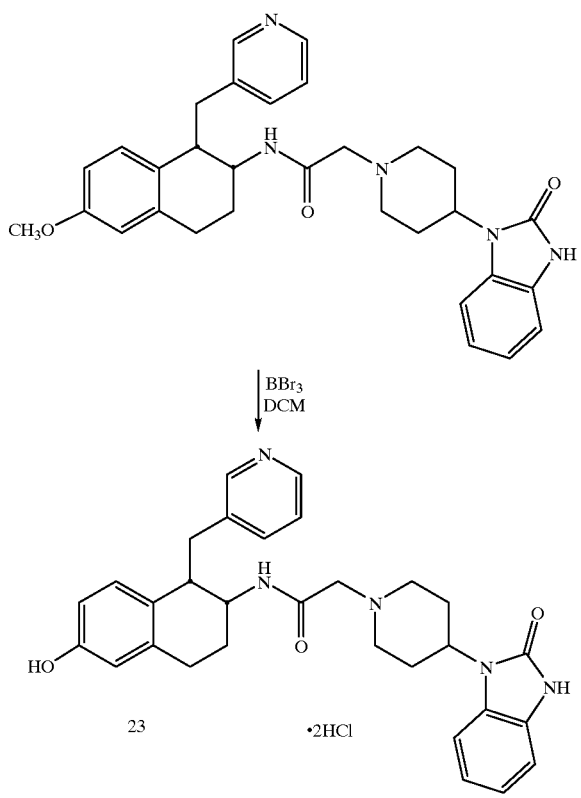

Example 12–13 trans-N-[2-(4-fluorophenyl)-3-(3-pyridinyl)propyl]-
4-[((2-fluorophenylsulfonyl)amino)methyl]-1-
cyclohexanamide hydrochloride 26 trans-N-[[[[2-(4-fluorophenyl)-3-(3-pyridinyl)
propyl]amino]methyl]-4-cyclohexyl]methyl] 2-
fluorobenzenesulfonamide bis-hydrochloride 27

A. Sodium metal (0.71 g, 30.9 mmol) was added to methanol (75 mL) and stirred at room temperature until the solid was consumed. At this time, 4-fluorophenylacetonitrile (3.5 mL, 29.3 mmol) was added and the mixture was stirred at room temperature for 10 min. 3-Pyridinecarboxaldehdye (2.77 mL, 29.3 mmol) was added and the resultant solution was heated at reflux for 2 h. The reaction was cooled to room temperature and neutralized with 2 N hydrochloric acid (16 mL, 32 mmol). The solvent was evaporated in vacuo, and the resultant residue was partitioned between water (~200 mL) and dichloromethane (~200 mL). The organic layer was dried over sodium sulfate, filtered and the solvent was evaporated in vacuo to give 2-(4-fluorophenyl)-3-pyridin-3-yl-acrylonitrile 24 as a colorless solid (6.11 g, 93%): $^1$H NMR(CDCl$_3$) d 7.16 (t, 2 H), 7.42–7.47 (m, 1 H), 7.48 (s, 1 H), 7.66–7.70 (m, 2 H), 8.47 (d, 1 H), 8.65 (d, 1 H), 8.84 (s, 1 H); MS m/e 225 (MH$^+$)

B. A suspension of 2-(4-fluoropheny)-3-pyridinyl-3-acrylonitrile 24 (1.5 g, 6.68 mmol) and platinum(IV) oxide (0.51 g, 2.24 mmol) in ethanol (60 mL) and water (15 mL) was reacted with hydrogen gas at a pressure of 65 psi for 6 h. The catalyst was removed by filtration, and the solvent was evaporated in vacuo. The residue was dissolved in diethyl ether (50 mL), and the small amount of insoluble material was removed by filtration. The ethereal solution was treated with 1 N hydrogen chloride in diethyl ether (20 mL). A yellow solid precipitated which was collected by filtration and washed generously with diethyl ether to give β-(3-pyridinylmethyl)-4-fluorophenethylamine bis hydrochloride salt 25 as a pale yellow solid (1.67 g, 82%). $^1$HNMR(DMSO-d$_6$) δ 3.03–3.21 (m, 4 H), 3.44–3.53(m, 1 H), 7.13 (t, 2 H), 7.27–7.33 (m, 2 H), 7.93 (t, 1 H), 8.27 (d, 1 H), 8.42 (br s, 3 H), 8.72–8.80 (m, 2 H); MS m/e 231 (MH$^+$).

C. A solution of 2-(1H-benzotriazole-1-yl)-1,1,3,3-tetramethyluronium hexafluorophosphate (HBTU) (1.03 g, 2.57 mmol), trans-4-[(2-fluorophenyl)sulfonylaminomethyl]cyclohexanecarboxylic acid (1.20 g, 2.57 mmol), and N,N-diisopropylethylamine (1.9 mL, 11.1 mmol) in N,N-dimethylformamide (15 mL) was stirred at room temperature for 10 min. 2-(4-Fluorophenyl)-3-pyridin-3-yl-propylamine dihydrochloride 25 (0.75 g, 2.47 mmol) was added, and the resultant solution was stirred at room temperature for 2 h. The reaction mixture was poured into water (~100 mL) and the product was extracted into dichloromethane (~100 mL). The organic layer was washed with water (3×100 mL), concentrated and the resultant residue purified via flash chromatography using methanol (5–10%) and triethylamine (0.5%) in dichloromethane as the eluant to give the desired cyclohexanamide as an oil. This material was dissolved in diethyl ether (~50 mL) and treated with 1 N hydrogen chloride in diethyl ether. A colorless solid formed which was collected by filtration, washed with ether and dried in vacuo to give N-[2-(4-fluorophenyl)-3-(3-pyridinyl)propyl]-4-[((2-fluorophenylsulfonyl)amino)methyl]-1-cyclohexanamide hydrochloride 26 as a colorless solid. $^1$H NMR(DMSO-d$_6$) δ 0.69–0.83 (m, 2 H), 1.07–1.19 (m, 3 H), 1.52–1.71 (m, 4 H), 1.94 (t, 1 H), 2.66 (br s, 2 H), 2.99–3.10 (m, 1 H), 3.17–3.43 (m, 4 H), 7.07 (t, 2 H), 7.16–7.21 (m, 2 H), 7.35–7.47 (m, 2 H), 7.66–7.95 (m, 5 H), 8.28 (d, 1 H), and 8.74 (br s, 2 H); MS m/e 528 (MH$^+$) (Scheme 37).

D. N-[2-(4-Fluorophenyl)-3-(3-pyridinyl)propyl]-4-[((2-fluorophenylsulfonyl)amino)methyl]-1-cyclohexanamide hydrochloride 26 was partitioned between a saturated solution of aqueous sodium bicarbonate and dichloromethane. The organic layer was dried over sodium sulfate and the solvent was evaporated in vacuo to give the free base as an oil. This oil (0.5 g, 0.944 mmol) was dissolved in tetrahydrofuran (~20 mL), and the resultant solution was added dropwise to a solution of borane (4.0 mmol) in tetrahydrofuran (14 mL) at ambient temperature. The solution was heated at reflux for 2 h. The resultant mixture was cooled to room temperature and several drops of water were added until unreacted borane was consumed. A 4 N solution of hydrochloric acid (2 mL) was added and the solution heated at reflux for 45 min. After the solution had cooled, 3 N aqueous sodium hydroxide was added (2.7 mL), and the mixture was concentrated in vacuo. The residue was partitioned between water (~50 mL) and dichloromethane (~50 mL). The organic layer was dried over sodium sulfate, and the solvent was evaporated in vacuo. The residue was dissolved in diethyl ether (~20 mL) and treated with 1 N hydrogen chloride in diethyl ether (~4 mL). The colorless precipitate was collected by filtration, washed generously with diethyl ether and dried in vacuo to give trans-N-[[[2-(4-fluorophenyl)-3-(3-pyridinyl)propyl]amino]methyl]-4-cyclohexyl]methyl] 2-fluorobenzenesulfonamide bis-hydrochloride 27 (0.371 g, 67%): $^1$H NMR(DMSO-d$_6$) δ

0.70–0.87 (m, 4 H), 1.22–1.36 (br s, 1 H), 1.64–1.88 (m, 6 H), 2.65–2.77 (m, 3 H), 2.99–3.33 (m, 3 H), 3.54–3.70 (m, 2 H), 7.13 (t, 2 H), 7.24–7.34 (m, 2 H), 7.37–7.48 (m, 2 H), 7.67–7.87 (m, 3 H), 7.96 (t, 1H) 8.17 (d, 1 H), 8.68 (s, 1 H), 8.70 (s, 1 H), 9.03 (brs, 1 H), and 9.24 (brs, 1 H); MS m/e 514 (MH$^+$) (Scheme 37).

room temperature for 24 h. The solution was poured into a saturated solution of aqueous sodium bicarbonate (~100 mL) and the product was extracted into dichloromethane (~100 mL). The organic layer was washed with water (5×~100 mL) and dried over sodium sulfate. The solvent was evaporated in vacuo to give the piperidineacetamide 28

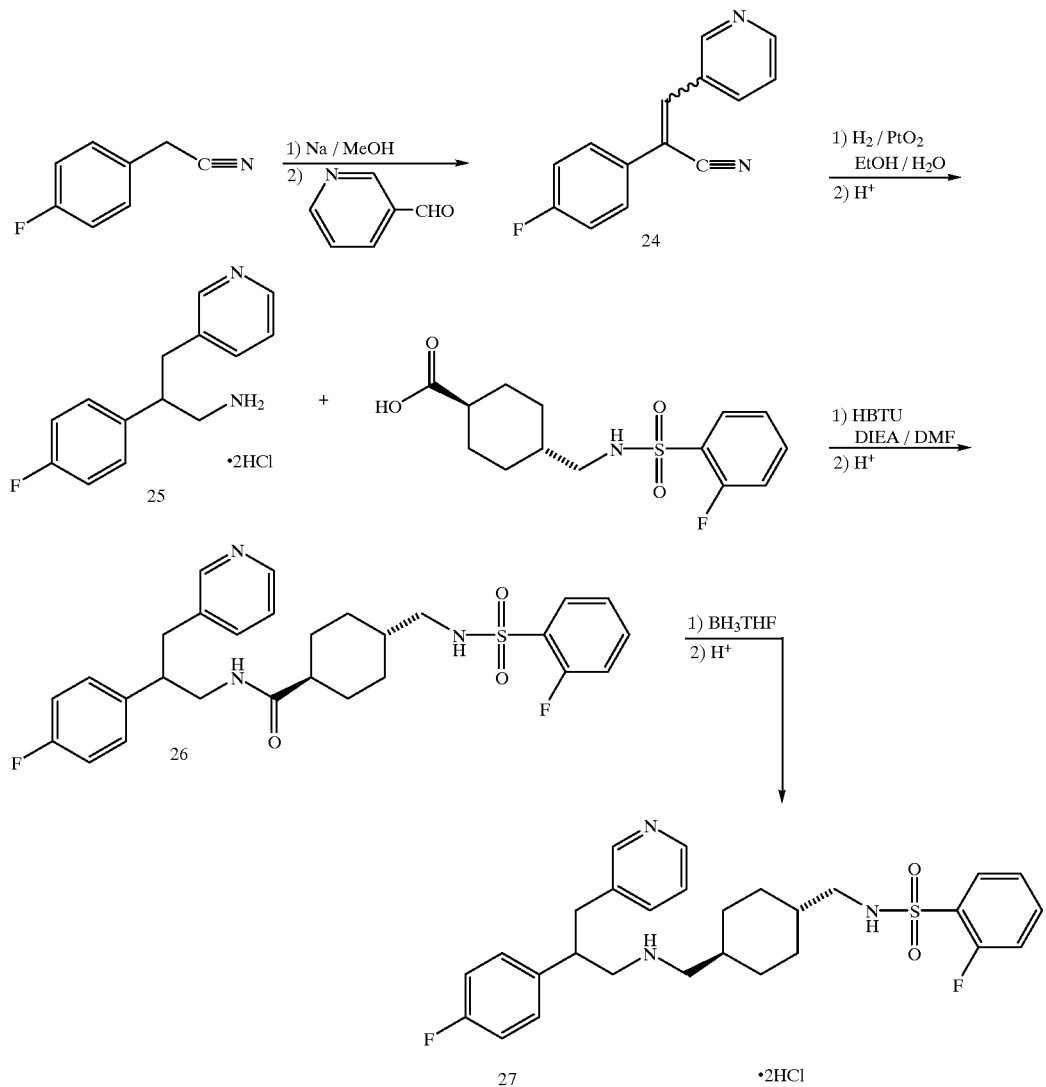

Scheme 37

Example 14

N-[2-(4-Fluorophenyl)-3-(3-pyridinyl)propyl]-4-[(2-fluorophenylsulfonyl)amino]-1-piperidineacetamide bis-trifluoroacetate 30

A. A solution of [4-(1,1-dimethylethoxy)carbonylamino-piperidin-1-yl]acetic acid (0.5 g, 1.94 mmol), 2-(1H-benzotriazole-1-yl)-1,1,3,3-tetramethyluronium hexafluorophosphate (0.73 g, 1.94 mmol), and N,N-diisopropylethylamine (1.5 mL, 8.71 mmol) in N,N-dimethylformamide (15 mL) was stirred at room temperature for 5 min. β-($^3$-Pyridinylmethyl)-4-fluorophenethylamine dihydrochloride 25 (0.586 g, 1.94 mmol) was added, and the resultant solution was stirred at as an oil, 0.52 g (57%): $^1$H NMR(CDCl$_3$) δ 0.98–1.25 (m, 2 H), 1.45 (s, 9 H), 1.71–1.79 (m, 2 H), 2.05–2.17 (m, 2 H), 2.41–2.50 (m, 2 H), 2.75–3.00 (m, 3 H), 3.04–3.17 (m, 1 H), 3.33–3.47 (m, 2 H), 3.72–3.83 (m, 1 H), 4.36 (br s, 1 H), 6.93–7.14 (m, 7 H), 7.25 (m, 1 H), 8.24 (s, 1 H), 8.39 (d, 1 H); MS m/e 471 (MH$^+$).

B. A solution of the piperidineacetamide 28 (0.46 g, 0.977 mmol) in dichloromethane (6 mL) was treated with trifluoroacetic acid (2 mL) and stirred at room temperature for 3 h. The solvent was evaporated in vacuo. The residue was dissolved in 1,2-dichloroethane (~10 mL), and the solvent evaporated in vacuo (repeated twice to remove residual trifluoroacetic acid), to give the 4-amino-1-piperidineacetamide 29 as a tris-trifluoroacetate salt, isolated as an amber glass, 0.66 g (95%): $^1$H NMR(DMSO-$d_6$); MS m/e 371 (MH$^+$).

C. 2-Fluorobenzenesulfonyl chloride (25 mg, ).126 mmol) was added to a solution of the 4-amino-1-piperidineacetamide 29 (82 mg, 0.115 mmol) and N,N-diisopropylethylamine (0.10 mL, 0.575 mmol) in acetonitrile (1 mL) at room temperature. The mixture was stirred at room temperature for 16 h and then water (0.30 mL) was added and the solution was applied to a $C_{18}$ reverse phase column for purification by HPLC. The column was eluted with a gradient of water/acetonitrile/trifluoroacetic acid to give N-[2-(4-fluorophenyl)-3-(3-pyridinyl)propyl]-4-[(2-fluorophenylsulfonyl)amino]-1-piperidineacetamide bis-trifluoroacetate 30 as a colorless solid, 28 mg (32%): $^1$H NMR(DMSO-$d_6$) δ 1.70–1.85 (m, 4 H), 2.91–3.47 (m, 10 H), 3.66–3.80 (m, 2 H), 7.07 (t, 2 H), 7.18 (m, 2 H), 7.38–7.50 (m, 2 H), 7.64 (t, 1 H), 7.71–7.85 (m, 2 H), 7.92 (d, 1 H), 8.31 (d, 1 H), 8.49 (s, 1 H), 8.57 (s, 1 H), 8.60 (s, 1 H); MS m/e 529 (MH$^+$) (Scheme 38).

Scheme 38

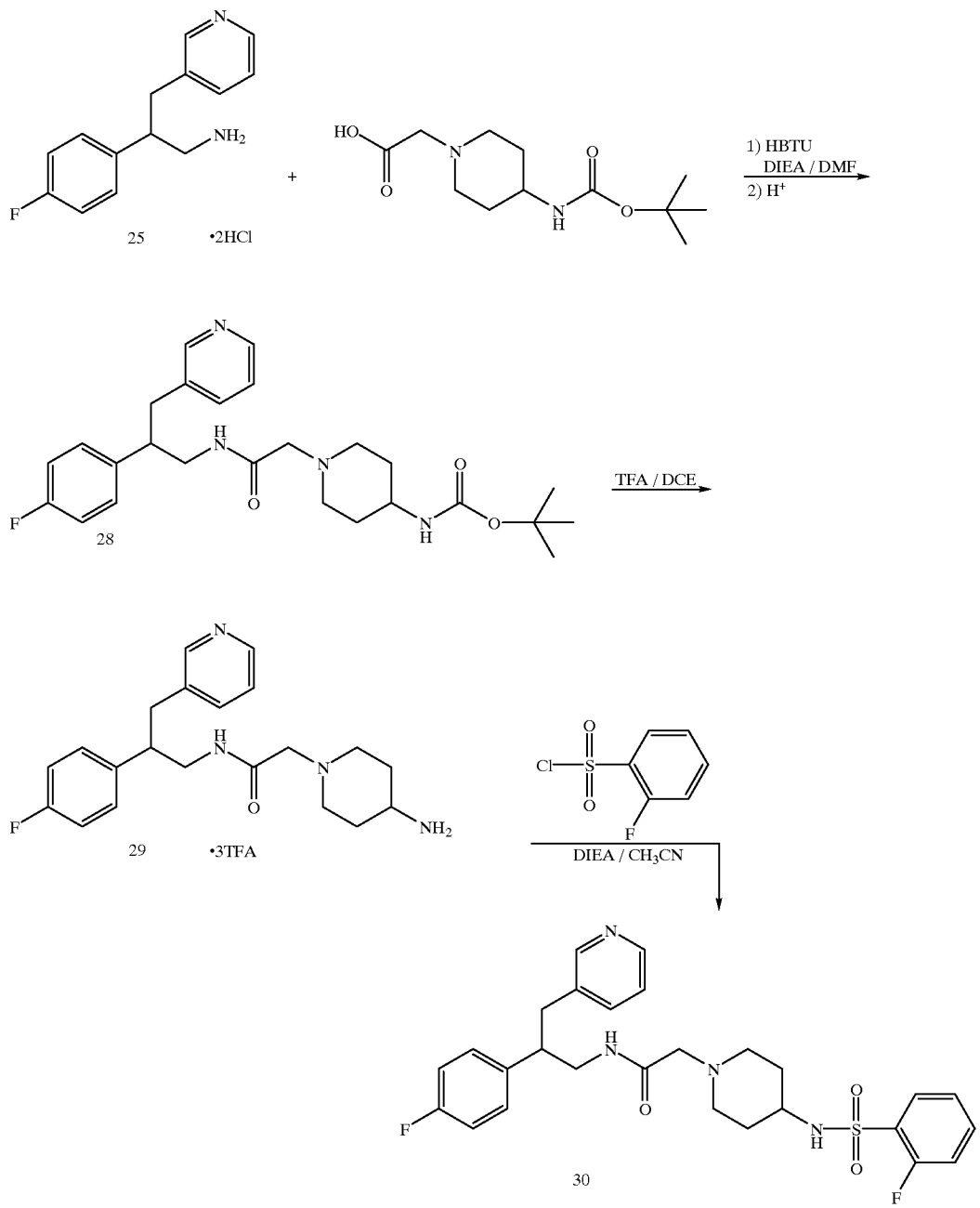

Additional compounds of this invention that were prepared using the experimental protocols described above include:

Mass Spectral Data of Compounds

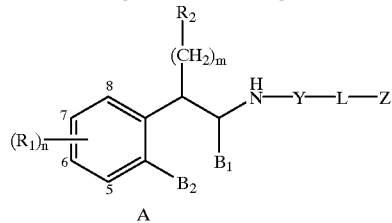

| # | R₁ | R₂ | m | B₁ | B₂ |
|---|---|---|---|---|---|
| 31 | (H) | 3-pyridyl | 1 | —CH₂— | —CH₂— |
| 19 | 6-OMe | 3-pyridyl | 1 | —CH₂— | —CH₂— |
| 20 | 6-OMe | 3-pyridyl (trans) | 1 | —CH₂— | —CH₂— |
| 23 | 6-OH | 3-pyridyl | 1 | —CH₂— | —CH₂— |
| 32 | (H) | 3-pyridyl | 1 | —CH₂— | —CH₂— |
| 33 | (H) | 3-pyridyl | 1 | —CH₂— | —CH₂— |
| 34a | (H) | 3-pyridyl (diast-A) | 1 | —CH₂— | —CH₂— |
| 34b | (H) | 3-pyridyl (diast-B) | 1 | —CH₂— | —CH₂— |
| 35 | 6-OMe | 3-pyridyl | 1 | —CH₂— | —CH₂— |
| 7a | 6-OMe | 3-pyridyl (diast-A) | 1 | —CH₂— | —CH₂— |
| 7b | 6-OMe | 3-pyridyl (diast-B) | 1 | —CH₂— | —CH₂— |
| 8a | 6-OMe | 3-pyridyl (diast-A) | 1 | —CH₂— | —CH₂— |
| 9a | 6-OMe | 3-pyridyl (diast-A) | 1 | —CH₂— | —CH₂— |
| 36 | (H) | 3-pyridyl | 1 | —CH₂— | —CH₂— |
| 37 | (H) | 3-pyridyl | 1 | —CH₂— | —CH₂— |
| 38a | (H) | 3-pyridyl (diast-A) | 1 | —CH₂— | —CH₂— |
| 38b | (H) | 3-pyridyl (diast-B) | 1 | —CH₂— | —CH₂— |
| 10 | 6-OMe | 3-pyridyl | 1 | —CH₂— | —CH₂— |
| 39 | (H) | 3-pyridyl | 1 | —CH₂— | —CH₂— |
| 40 | (H) | 3-pyridyl | 1 | —CH₂— | —CH₂— |
| 41 | (H) | 3-pyridyl | 1 | —CH₂— | —CH₂— |
| 42 | (H) | 3-pyridyl | 1 | —CH₂— | —CH₂— |
| 43a | (H) | 3-pyridyl (diast-A) | 1 | —CH₂— | —CH₂— |
| 43b | (H) | 3-pyridyl (diast-B) | 1 | —CH₂— | —CH₂— |
| 11a | 6-OH | 3-pyridyl (diast-A) | 1 | —CH₂— | —CH₂— |
| 11b | 6-OH | 3-pyridyl (diast-B) | 1 | —CH₂— | —CH₂— |
| 17 | 6-F | 3-pyridyl | 1 | —CH₂— | —CH₂— |
| 44 | 6-F | 3-pyridyl | 1 | —CH₂— | —CH₂— |
| 45 | 6-F | 3-pyridyl | 1 | —CH₂— | —CH₂— |
| 46 | 6-F | 3-pyridyl | 1 | —CH₂— | —CH₂— |
| 47 | 6-F | 3-pyridyl | 1 | —CH₂— | —CH₂— |
| 48 | 6-F | 3-pyridyl | 1 | —CH₂— | —CH₂— |
| 49 | 6-F | 3-pyridyl | 1 | —CH₂— | —CH₂— |
| 22 | (H) | 3-pyridyl | 1 | —CH₂— | —CH₂— |
| 21 | (H) | 3-pyridyl | 1 | —CH₂— | —CH₂— |
| 50 | (H) | 3-pyridyl | 1 | —CH₂— | —CH₂— |
| 51 | (H) | 3-pyridyl | 1 | —CH₂— | —CH₂— |
| 52 | 6-OMe | 3-thienyl | 1 | —CH₂— | —CH₂— |
| 53 | 6-F | 3-pyridyl | 1 | —CH₂— | —CH₂— |
| 54 | 6-F | 3-pyridyl | 1 | —CH₂— | —CH₂— |
| 55 | 6-F | 3-pyridyl | 1 | —CH₂— | —CH₂— |
| 56 | 6-F | 3-pyridyl | 1 | —CH₂— | —CH₂— |
| 57 | 6-F | 3-pyridyl | 1 | —CH₂— | —CH₂— |
| 58 | 6-F | 3-pyridyl | 1 | —CH₂— | —CH₂— |
| 59 | 6-F | 3-pyridyl | 1 | —CH₂— | —CH₂— |
| 60 | 6-F | 3-pyridyl | 1 | —CH₂— | —CH₂— |
| 61 | 6-OMe | 3-thienyl | 1 | —CH₂— | —CH₂— |
| 62 | 6-OMe | 3-thienyl | 1 | —CH₂— | —CH₂— |
| 63 | 6-OMe | 3-thienyl | 1 | —CH₂— | —CH₂— |
| 64 | 6-OMe | 3-thienyl | 1 | —CH₂— | —CH₂— |

-continued

Mass Spectral Data of Compounds

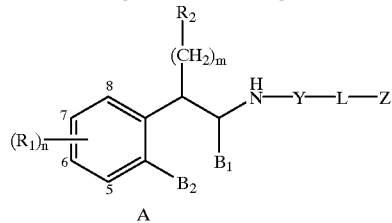

A

| # | (R₁)ₙ | R₂ | m | Y | L |
|---|---|---|---|---|---|
| 65 | (H) | 3-pyridyl | 1 | —CH₂— | —CH₂— |
| 66 | (H) | 3-pyridyl (diast-A) | 1 | —CH₂— | —CH₂— |
| 67 | 6-F | 3-pyridyl (diast-A) | 1 | —CH₂— | —CH₂— |
| 68 | (H) | 3-pyridyl | 1 | —CH₂— | —CH₂— |
| 69 | 6-OMe | 5(4)-imidazolyl | 1 | —CH₂— | —CH₂— |
| 70 | 6-F | 3-pyridyl (diast-A) | 1 | —CH₂— | —CH₂— |
| 71 | 6-F | 3-pyridyl (diast-B) | 1 | —CH₂— | —CH₂— |
| 72 | (H) | 3-pyridyl | 1 | —CH₂— | —CH₂— |
| 73 | 6-OMe | 5(4)-imidazolyl | 1 | —CH₂— | —CH₂— |
| 74 | 6-OMe | 3-thienyl | 1 | —CH₂— | —CH₂— |
| 75 | 6-OMe | 4-Cl—phenyl | 1 | —CH₂— | —CH₂— |
| 76 | 6-OMe | 4-Cl—phenyl | 1 | —CH₂— | —CH₂— |
| 77 | 6-F | vinyl | 1 | —CH₂— | —CH₂— |
| 78 | 6-F | vinyl | 1 | —CH₂— | —CH₂— |
| 79 | 6-OMe | vinyl | 1 | —CH₂— | —CH₂— |
| 80 | 6-OMe | vinyl | 1 | —CH₂— | —CH₂— |
| 81 | 6-OH | vinyl | 1 | —CH₂— | —CH₂— |
| 82 | 6-OMe | (H) | 0 | —CH₂— | —CH₂— |
| 83 | 6-OH | (H) | 0 | —CH₂— | —CH₂— |
| 84 | 6-OMe | (H) | 0 | —CH₂— | —CH₂— |
| 85 | 6-OH | (H) | 0 | —CH₂— | —CH₂— |
| 86 | 6-OMe | 3-pyridyl | 1 | H | H |
| 87 | 6-OH | 3-pyridyl | 1 | H | H |
| 88 | 6-OMe | 3-pyridyl | 1 | H | H |
| 89 | 6-OMe | 3-pyridyl | 1 | H | H |
| 90 | 6-OH | 3-pyridyl | 1 | H | H |
| 91 | 6-OH | 3-pyridyl | 1 | H | H |
| 26 | 6-F | 3-pyridyl | 1 | H | H |
| 27 | 6-F | 3-pyridyl | 1 | H | H |
| 92 | 6-F | 3-pyridyl | 1 | H | H |
| 30 | 6-F | 3-pyridyl | 1 | H | H |
| 93 | (H) | 3-pyridyl | 1 | —CH₂— | —CH₂— |
| 94 | 6-OMe | (H) | 0 | H | H |
| 95 | 6-OMe | (H) | 0 | H | H |
| 96 | 6-OH | (H) | 0 | H | H |

| # | Y | L | Z | MH⁺ | Calc M |
|---|---|---|---|---|---|
| 31 | C=O | —CH₂—N(piperidine)— | 1-(benzimidazol-2(3H)-one-yl) | 496 | 495 |
| 19 | C=O | —CH₂—N(piperidine)— | 1-(benzimidazol-2(3H)-one-yl) | 526 | 525 |

-continued
Mass Spectral Data of Compounds
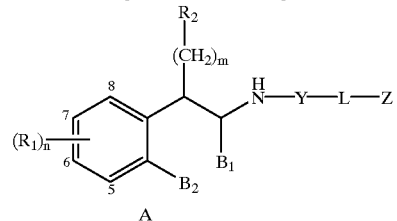
| | | | | | |
|---|---|---|---|---|---|
| 20 | C=O | -CH₂-N(piperidine) | benzimidazol-2-one (N-linked) | 526 | 525 |
| 23 | C=O | -CH₂-N(piperidine) | benzimidazol-2-one (N-linked) | 512 | 511 |
| 32 | C=O | CH(NH₂)-(CH₂)₄- | -NH-SO₂-(2-F-C₆H₄) | 525 | 524 |
| 33 | C=O | CH(NH₂)-(CH₂)₄- | -NH-SO₂-C₆H₅ | 507 | 506 |
| 34a | C=O | CH(NH₂)-(CH₂)₄- | -NH-SO₂-C₆H₅ | 507 | 506 |
| 34b | C=O | CH(NH₂)-(CH₂)₄- | -NH-SO₂-C₆H₅ | 507 | 506 |
| 35 | C=O | CH(NH₂)-(CH₂)₄- | -NH-SO₂-(2-F-C₆H₄) | 555 | 554 |
| 7a | C=O | CH(NH₂)-(CH₂)₄- | -NH-SO₂-(2-F-C₆H₄) | 555 | 554 |

-continued
Mass Spectral Data of Compounds
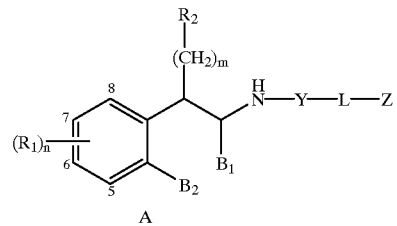
| | | | | | |
|---|---|---|---|---|---|
| 7b | C=O | NH₂ (chain) | N-SO₂-Ph-F (2-F) | 555 | 554 |
| 8a | —CH₂— | NH₂ (chain) | N-SO₂-Ph-F (2-F) | 541 | 540 |
| 9a | —CH₂— | NH₂ (chain) | N-SO₂-Ph-F (2-F) | 527 | 526 |
| 36 | C=O | NHC(O)CH₃ (chain) | N-SO₂-Ph-F (2-F) | 567 | 566 |
| 37 | C=O | NHC(O)CH₃ (chain) | N-SO₂-Ph | 549 | 548 |
| 38a | C=O | NHC(O)CH₃ (chain) | N-SO₂-Ph | 549 | 548 |
| 38b | C=O | NHC(O)CH₃ (chain) | N-SO₂-Ph | 549 | 548 |

-continued
Mass Spectral Data of Compounds
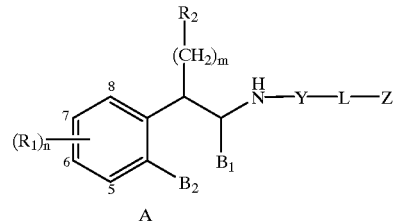
| 10 | C=O | NHAc hexyl | NHSO2(2-F-C6H4) | 597 | 596 |
| 39 | C=O | NHC(O)Ph hexyl | NHSO2Ph | 611 | 610 |
| 40 | C=O | NHC(O)NHEt hexyl | NHSO2Ph | 578 | 577 |
| 41 | C=O | NHC(O)NH2 hexyl | NHSO2Ph | 550 | 549 |
| 42 | C=O | NHC(=NH)NH2 hexyl | NHSO2Ph | 549 | 548 |
| 43a | C=O | N(CH3)2 hexyl | NHSO2Ph | 535 | 534 |
| 43b | C=O | N(CH3)2 hexyl | NHSO2Ph | 535 | 534 |

-continued
Mass Spectral Data of Compounds
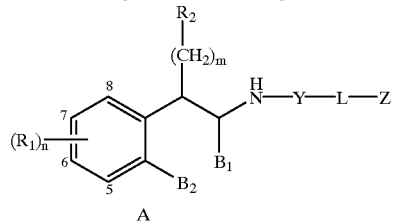
| | | | | | |
|---|---|---|---|---|---|
| 11a | C=O | | | 583 | 582 |
| 11b | C=O | | | 583 | 582 |
| 17 | C=O | | | 523 | 522 |
| 44 | C=O | | | 501 | 500 |
| 45 | C=O | | | 516 | 515 |
| 46 | C=O | | | 517 | 516 |
| 47 | C=O | | | 515 | 514 |
| 48 | C=O | | | 537 | 536 |
| 49 | C=O | | | 555 | 554 |

-continued
Mass Spectral Data of Compounds
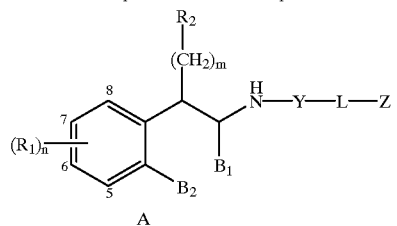
| | | | | | |
|---|---|---|---|---|---|
| 22 | C=O | 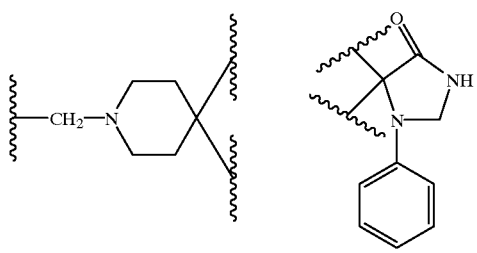 | | 510 | 509 |
| 21 | C=O | 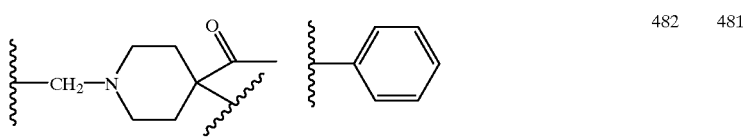 | | 482 | 481 |
| 50 | C=O | 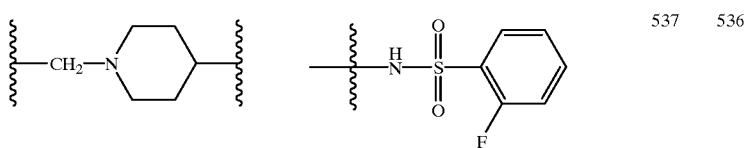 | | 537 | 536 |
| 51 | C=O | 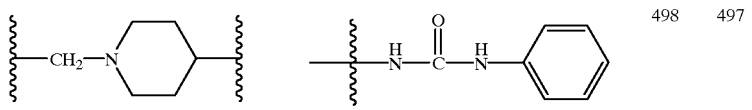 | | 498 | 497 |
| 52 | C=O | 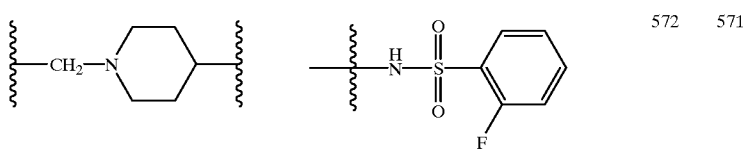 | | 572 | 571 |
| 53 | C=O | 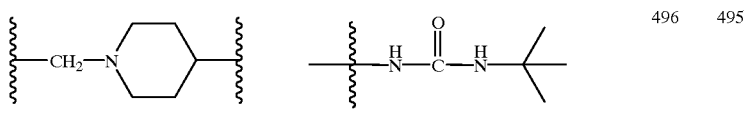 | | 496 | 495 |
| 54 | C=O | 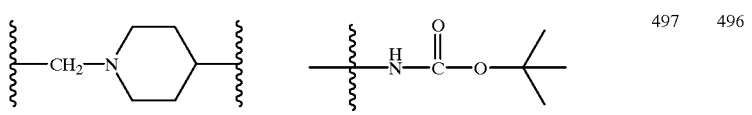 | | 497 | 496 |
| 55 | C=O | 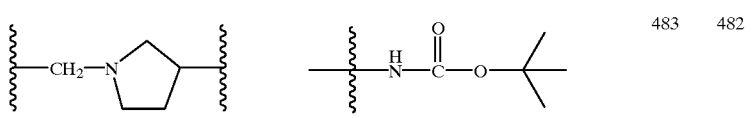 | | 483 | 482 |

-continued
Mass Spectral Data of Compounds
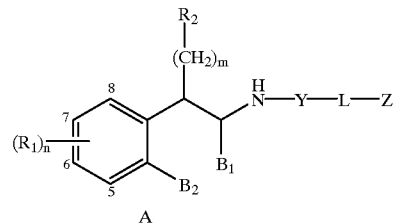
| # | A | | | | |
|---|---|---|---|---|---|
| 56 | C=O | -CH2-N-pyrrolidine | -N(H)-C(O)-O-tBu | 483 | 482 |
| 57 | C=O | -CH2-N-pyrrolidine | -N(H)-C(O)-O-tBu | 483 | 482 |
| 58 | C=O | -CH2-N-pyrrolidine | -N(H)-SO2-Ph | 523 | 522 |
| 59 | C=O | -CH2-N-pyrrolidine | -N(H)-SO2-Ph | 523 | 522 |
| 60 | C=O | -CH2-N-pyrrolidine | -N(H)-C(O)-Ph | 487 | 486 |
| 61 | C=O | -CH2-N-piperidine | benzimidazolone-N | 531 | 530 |
| 62 | C=O | -CH2-N-piperidine | benzimidazolone-N | 517 | 516 |
| 63 | C=O | -CH(NH2)-(CH2)4- | -N(H)-SO2-(2-F-Ph) | 560 | 559 |

-continued
Mass Spectral Data of Compounds
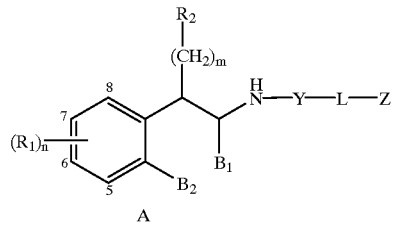
| | | | | | |
|---|---|---|---|---|---|
| 64 | —CH₂— | NH₂ (chain) | N-H-S(=O)₂-Ph-F (ortho) | 546 | 545 |
| 65 | —CH₂— | NH₂ (chain) | N-H-S(=O)₂-Ph | 493 | 492 |
| 66 | —CH₂— | NH₂ (chain) | N-H-S(=O)₂-Ph | 493 | 492 |
| 67 | —CH₂— | NH₂ (chain) | N-H-S(=O)₂-Ph-F (ortho) | 529 | 528 |
| 68 | —CH₂— | NH—Et (chain) | N-H-S(=O)₂-Ph | 521 | 520 |
| 69 | —CH₂— | NH₂ (chain) | N-H-S(=O)₂-Ph | 530 | 529 |
| 70 | C=O | NH₂ (chain) | N-H-S(=O)₂-Ph-F (ortho) | 543 | 542 |
| 71 | C=O | NH₂ (chain) | N-H-S(=O)₂-Ph-F (ortho) | 543 | 542 |

-continued
Mass Spectral Data of Compounds
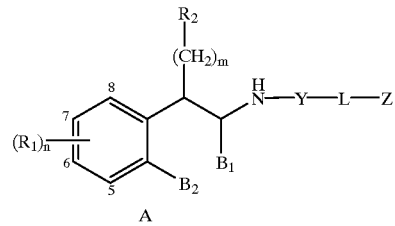
| 72 | C=O | (structure: NHC(O)NH-Ph on chain) | -NH-SO2-Ph | 626 | 625 |
| 73 | C=O | -CH2-piperidine- | benzimidazol-2(3H)-one-N- | 515 | 514 |
| 74 | C=O | NHC(O)CH3 on chain | -NH-SO2-(2-F-Ph) | 602 | 601 |
| 75 | C=O | NH2 on chain | -NH-SO2-(2-F-Ph) | 588 | 587 |
| 76 | —CH2— | NH2 on chain | -NH-SO2-(2-F-Ph) | 574 | 573 |
| 77 | C=O | NH2 on chain | -NH-SO2-Ph | 474 | 473 |
| 78 | —CH2— | NH2 on chain | -NH-SO2-Ph | 460 | 459 |

-continued
Mass Spectral Data of Compounds
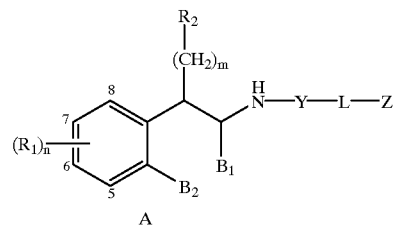
| | | | | | |
|---|---|---|---|---|---|
| 79 | C=O | -CH₂-N(piperidine)- | benzimidazolone | 475 | 474 |
| 80 | -CH₂- | -CH₂-N(piperidine)- | benzimidazolone | 461 | 460 |
| 81 | -CH₂- | -CH₂-N(piperidine)- | benzimidazolone | 447 | 446 |
| 82 | C=O | -CH₂-N(piperidine)- | benzimidazolone | 435 | 434 |
| 83 | C=O | -CH₂-N(piperidine)- | benzimidazolone | 421 | 420 |
| 84 | -CH₂- | cyclohexyl-CH₂- | -NH-SO₂-(2-F-phenyl) | 461 | 460 |

-continued
Mass Spectral Data of Compounds
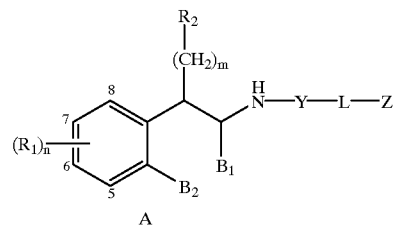
| 85 | —CH₂— | cyclohexyl-CH₂ | NHSO₂-(2-F-C₆H₄) | 447 | 446 |
| 86 | C=O | CH₂-piperidinyl | benzimidazolone-N | 500 | 499 |
| 87 | C=O | CH₂-piperidinyl | benzimidazolone-N | 486 | 485 |
| 88 | C=O | cyclohexyl-CH₂ | NHSO₂-(2-F-C₆H₄) | 540 | 539 |
| 89 | —CH₂— | cyclohexyl-CH₂ | NHSO₂-(2-F-C₆H₄) | 526 | 525 |
| 90 | C=O | cyclohexyl-CH₂ | NHSO₂-(2-F-C₆H₄) | 526 | 525 |
| 91 | —CH₂— | cyclohexyl-CH₂ | NHSO₂-(2-F-C₆H₄) | 512 | 511 |

-continued
Mass Spectral Data of Compounds
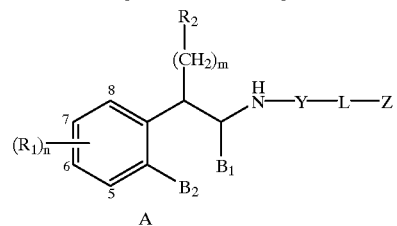
| | | | | | |
|---|---|---|---|---|---|
| 26 | C=O | cyclohexyl-CH₂ | NH-SO₂-C₆H₄-F | 528 | 527 |
| 27 | —CH₂— | cyclohexyl-CH₂ | NH-SO₂-C₆H₄-F | 514 | 513 |
| 92 | C=O | CH₂-piperidine | NH-C(O)-C₆H₅ | 475 | 474 |
| 30 | C=O | CH₂-piperidine | NH-SO₂-C₆H₄-F | 529 | 528 |
| 93 | C=O | CH₂-piperazine | C₆H₄-OCH₃ | 471 | 470 |
| 94 | C=O | cyclohexyl-CH₂ | NH-SO₂-C₆H₄-F | 449 | 448 |
| 95 | —CH₂— | cyclohexyl-CH₂ | NH-SO₂-C₆H₄-F | 435 | 434 |
| 96 | —CH₂— | cyclohexyl-CH₂ | NH-SO₂-C₆H₄-F | 421 | 420 |

IN VITRO ASSAYS

NPY5 HTS Centrifugation Assay

The compounds described in this invention were evaluated for binding to the human neuropeptide Y5 receptor.

Stable Transfection

The human NPY5 receptor cDNA (Genbank Accession number U66275) was inserted into the vector pClneo (Invitrogen) and transfected into human embryonic kidney cells (HEK-293) via Calcium phosphate method (Cullen 1987). Stably transfected cells were selected with G-418 (600 ug/mL). Stably transfected cells served as the source for the membranes for the NPY5 receptor binding assay.

Membrane Preparation

NPY5-transfected HEK293 cells were grown to confluence in 150 cm$^2$ culture dishes. Cells were washed once with phosphate-buffered saline (Gibco Cat#14040–133). Cells were then incubated in phosphate-buffered saline without Calcium and without Magnesium, supplemented with 2 mM EDTA. Cells were incubated for 10 minutes at room temperature and the cells were collected by repetitive pipeting. Cells were formed into pellets and then frozen at −80 until needed. Frozen pellets were homogenized with a polytron at full speed for 12 seconds in a homogenization buffer (20 mM Tris HCl, 5 mM EDTA, pH 7.4). Homogenates were centrifuged for 5 minutes at 4C at 200 g. Supernatants were transferred to corex tubes and centrifuged for 25 minutes at 28,000 g. Pellets were re-suspended in Binding (2 mM HEPES, 10 mM NaCl, 0.22 mM KH$_2$PO$_4$, 1.3mM CaCl$_2$, 0.8 mM MgSO$_4$, pH 7.4). Membranes were kept on ice until use.

A competition binding assay, known to those skilled in the art, was used in which compounds of formula A compete with $^{125}$I-PYY for binding to cell membranes. In simple terms, the less $^{125}$I-PYY bound to the membranes implies that a compound is a good inhibitor (competitor). Bound $^{125}$I-PYY is determined by centrifugation of membranes, aspirating supernatant, washing away residual $^{125}$I-PYY and subsequently counting the bound sample in a g-counter.

Procedure for Radioligand binding assay

Compounds to be tested were prepared as 10x stocks in binding buffer and added first to assay tubes (RIA vials, Sarstedt). Twenty (20) μL of each 10× compound stock is pipeted into vials and 80 μL of $^{125}$I-PYY (NEN catalog number NEX240), which has been diluted to a concentration of 200 pM in 0.25% BSA in binding buffer, is added to the compound tubes (final concentration of $^{125}$I-PYY is 80 pM). To each tube is added 100 μL of membranes and the mixture is agitated by pipeting 2 times. Samples are incubated for 1 hr at room temperature. Aluminum cast plates (Sarstedt) containing the vials are then centrifuged 10 minutes at 3200 rpm in a Sorvall RT6000. Supernatant is then aspirated. To each vial 400 μL PBS is added and this is then aspirated again. Vials are then put in carrier polypropylene 12×75 tube and counted in gamma counter (Packard). Non-specific binding is determined in the presence of 300 nM NPY. Percent inhibition of $^{125}$I-PYY binding is calculated by subtracting non-specific binding from the test samples (compound (I)), taking these counts and dividing by total binding, and multiplying by 100.

Binding Affinities of Compounds A for the Human NPY Y5 Receptor (expressed as % Inhibition of $^{125}$I-PYY Binding)

TABLE 2

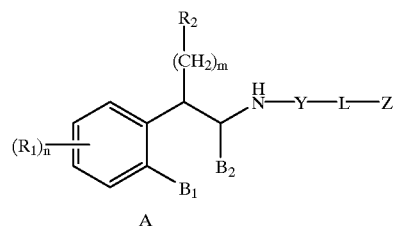

| # | % Inh @ 3 uM | % Inh @ 300 nM |
| --- | --- | --- |
| 7a | 97 | 69 |
| 7b | 67 | 11 |
| 8 | 100 | 96 |
| 9 | 98 | 104 |
| 10 | 96 | 60 |
| 17 | 102 | 98 |
| 19 | 101 | 69 |
| 20 | 96 | 88 |
| 21 | 98 | 83 |
| 22 | 70 | 32 |
| 23 | 100 | 96 |
| 26 | 110 | 108 |
| 27 | 110 | 105 |
| 30 | 110 | 100 |
| 31 | 100 | 91 |
| 32 | 100 | 62 |
| 33 | 96 | 52 |
| 34a | 97 | 87 |
| 34b | 99 | 61 |
| 35 | 96 | 54 |
| 36 | 95 | 22 |
| 37 | 102 | 89 |
| 38a | 104 | 80 |
| 38b | 101 | 59 |
| 39 | 95 | 70 |
| 40 | 92 | 21 |
| 41 | 94 | 54 |
| 42 | 85 | 21 |
| 43a | 93 | 54 |
| 43b | 86 | 62 |
| 44 | 98 | 93 |
| 45 | 95 | 68 |
| 46 | 107 | 90 |
| 47 | 98 | 91 |
| 48 | 103 | 97 |
| 49 | 95 | 85 |
| 50 | 108 | 103 |
| 51 | 102 | 85 |
| 52 | 100 | 96 |
| 53 | 92 | 84 |
| 54 | 100 | 99 |
| 55 | 106 | 96 |
| 56 | 94 | 88 |
| 57 | 93 | 87 |
| 58 | 91 | 93 |
| 59 | 93 | 90 |
| 60 | 109 | 86 |
| 61 | 87 | 66 |
| 62 | 103 | 74 |
| 63 | 71 | 33 |
| 64 | 103 | 91 |
| 65 | 98 | 79 |
| 66 | 102 | 98 |
| 67 | 99 | 102 |
| 68 | 108 | 109 |
| 69 | 56 | 26 |
| 70 | 92 | 93 |
| 71 | 73 | 59 |
| 72 | 73 | 41 |
| 73 | 63 | 32 |
| 74 | 100 | 89 |

TABLE 2-continued

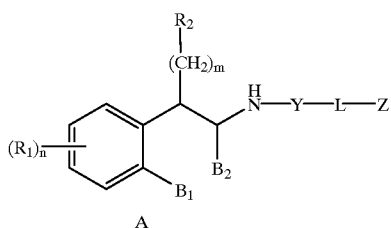

| # | % Inh @ 3 uM | % Inh @ 300 nM |
|---|---|---|
| 75 | 78 | 28 |
| 76 | 91 | 45 |
| 77 | 84 | 56 |
| 78 | 75 | 65 |
| 79 | 99 | 69 |
| 80 | 82 | 47 |
| 81 | 94 | 89 |
| 82 | 85 | 63 |
| 83 | 92 | 72 |
| 84 | 93 | 79 |
| 85 | 100 | 96 |
| 86 | 91 | 88 |
| 87 | 96 | 97 |
| 88 | 103 | 104 |
| 89 | 100 | 103 |
| 90 | 88 | 93 |
| 91 | 100 | 104 |
| 92 | 104 | 92 |
| 93 | 97 | 81 |
| 94 | 98 | 93 |
| 95 | 102 | 96 |
| 96 | 98 | 91 |

IN VIVO ASSAYS

Rodent Feeding Model

Measurement of Food Intake in Food-Deprived Rats

Male Long-Evans rats (180–200 grams) are housed individually and are maintained on a once-a-day feeding schedule (i.e. 10 a.m. until 4 p.m.) for five days following quarantine to allow the animals to acclimate to feeding on powdered chow (#5002 PMI Certified Rodent Meal) during the allotted time. The chow is made available in an open jar, anchored in the cage by a wire, with a metal follower covering the food to minimize spillage. Water is available ad-libitum.

Animals are fasted for 18 hours prior to testing. At the end of the fasting period, animals are administered either compounds of the invention or vehicle. Vehicle and test compounds are administered either orally (5 mL/kg) 60 minutes prior to the experiment, or 30 minutes prior when given subcutaneously (1 mL/kg) or intraperitoneally (1 mL/kg). Compounds of the invention are administered orally as a suspension in aqueous 0.5% methylcellulose-0.4% Tween 80, or intraperitoneally as a solution or suspension in PEG 200; compound concentrations typically range from 1 mg/kg to 100 mg/kg, preferably from 10–30 mg/kg. Food intake is measured at 2, 4, and 6 hours after administration by weighing the special jar containing the food before the experiment and at the specified times. Upon completion of the experiment, all animals are given a one-week washout period before retesting.

Percent reduction of food consumption is calculated subtracting the grams of food consumed by the treated group from the grams of food consumed by the control group divided by the grams of food consumed by the control group, multiplied by 100.

$$\% \text{ change} = \frac{\text{Treatment} - \text{Vehicle}}{\text{Vehicle}} \times 100$$

A negative value indicates a reduction in food consumption and a positive value indicates an increase in food consumption.

| Compound | Dose (mg/kg) (#rats) | Food Consumption (grams) | | | |
|---|---|---|---|---|---|
| | | 2 hrs (% chg.) | 4 hrs (% chg.) | 6 hrs (% chg.) | 2–6 hrs (% chg.) |
| Vehicle PEG-2000 | N = 6 | 8.85 g | 13.97 g | 22.85 g | 14.00 g |
| 70 | 30 (i.p.) N = 7 | 1.30 g (−85.3%) | 3.44 g (−75.4%) | 6.14 g (−73.1%) | 4.84 g (−65.4%) |

What is claimed is:

1. A compound of the formula:

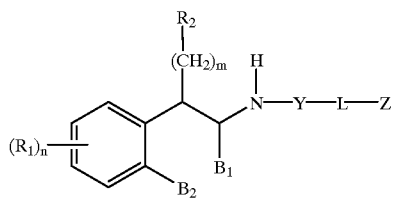

in which:

$R_1$ is independently selected from the group consisting of hydrogen; hydroxy; halo; $C_{1-8}$alkyl; substituted $C_{1-8}$alkyl; $C_{1-8}$alkoxy; substituted $C_{1-8}$alkoxy; trifluoroalkyl; $C_{1-8}$alkylthio; substituted $C_{1-8}$alkylthio; $C_{3-6}$cycloalkyl; $C_{3-8}$cycloalkoxy; nitro; amino; $C_{1-6}$alkylamino; $C_{1-8}$dialkylamino; $C_{4-8}$cycloalkylamino; cyano; carboxy; $C_{1-5}$alkoxycarbonyl; $C_{1-5}$alkylcarbonyloxy; formyl; carbamoyl; phenyl; and substituted phenyl;

n is 1–2;

$B_1$ is hydrogen;

$B_2$ is hydrogen; or $B_1$ and $B_2$ are methylene and joined together to form a five or six membered ring;

m is 0–3;

$R_2$ is pyridyl

L is selected from the group consisting of
$C_{1-8}$alkylene; $C_{2-20}$alkenylene; $C_{2-10}$alkynylene; $C_{3-7}$cycloalkylene; $C_{3-7}$cycloalkyl$C_{1-4}$alkylene; aryl$C_{1-4}$alkylene;
α-amino$C_{4-7}$alkylene;

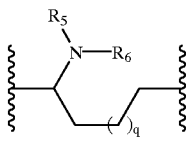

101

(N-methylene)pyrrolidin-3-yl;

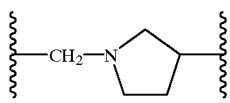

Y is methylene or carbonyl;

Z is selected from the group consisting of:

aryl;

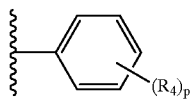

N-sulfonamido;

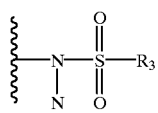

N-(aryl)sulfonamido;

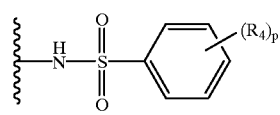

arylamido;

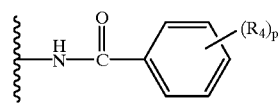

arylureido;

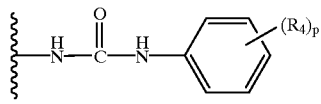

arylacetamido:

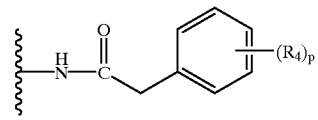

(aryloxy)carbonylamino;

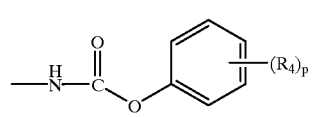

102

2,3-dihydro-2-oxo-1H-benzimidazol-1-yl;

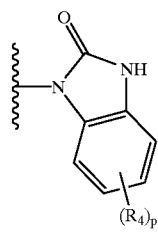

and 1-aryl-2,3-dihydro4-oxo-imidazol-5,5-diyl;

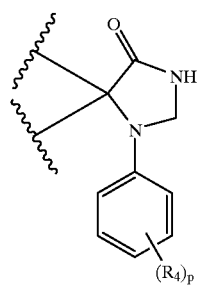

$R_3$ is independently selected from the group consisting of $C_{1-6}$ alkyl; substituted $C_{1-8}$alkyl; cycloalkyl; substituted cycloalkyl; naphthyl; substituted naphthyl; heteroaryl; and substituted heteroaryl;

$R_4$ is independently selected from the group consisting of hydrogen; $C_{1-8}$alkyl; $C_{1-8}$alkoxy; substituted $C_{1-8}$alkoxy; hydroxy; halogen; cyano; nitro; amino; $C_{1-8}$alkylamino; and $C_{1-8}$dialkylamino;

$R_5$ is independently selected from the group consisting of hydrogen;

$C_{1-8}$alkyl; $C_1$alkylcarbonyl; aroyl; carbamoyl; amidino; $C_{1-8}$ alkyl;

$C_{1-8}$alkylaminocarbonyl; (arylamino)carbonyl; and aryl $C_{1-8}$ alkylcarbonyl;

$R_6$ is independently selected from hydrogen and $C_{1-8}$ alkyl;

p is 1–3;

q is 1–3;

and enantiomers, diastereomers and pharmaceutically acceptable salts thereof;

provided that when L is $C_{1-6}$alkylene; $C_{2-10}$ alkenylene; $C_{2-10}$ alkynylene;

$C_{3-7}$cycloalkylene; $C_{3-7}$cycloalkyl $C_{1-4}$alkylene; aryl $C_{1-4}$ alkylene; or -amino$C_{4-7}$alkylene; then Z is phenyl, N-sulfonamido or N-(aryl)sulfonamido;

when L is (N-methylene)pyrrolidin-3-yl; then Z is N-sulfonamido; N-(aryl)sulfonamido; 2,3-dihydro-2-oxo-1H-benzimidazol-1-yl; benzamido; phenylureido; phenylacetamido or (phenoxy)carbonylamino;

and when $B_1$ and $B_2$ are both methylene thus forming a six membered ring and when L is $C_{1-10}$alkylene; $C_{2-10}$alkeneylene; $C_{2-10}$ alkenylene; or aryl$C_{1-4}$alkylene; then Z is other than N-sulfonamido, N-(aryl)sulfonamido or phenyl.

2. A compound of claim 1 selected from the group consisting of:
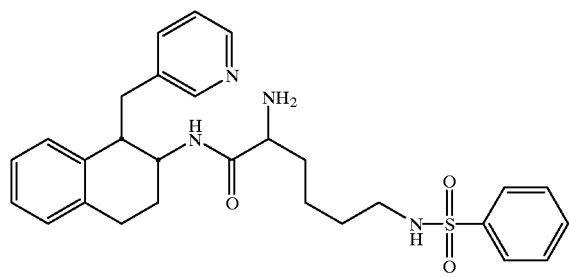
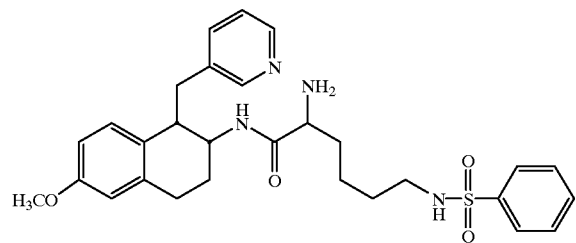
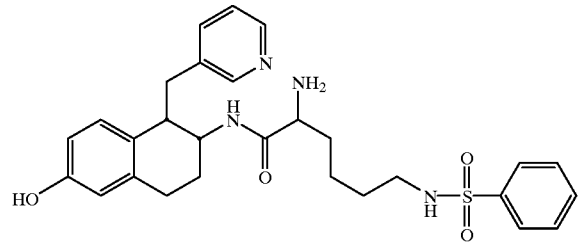
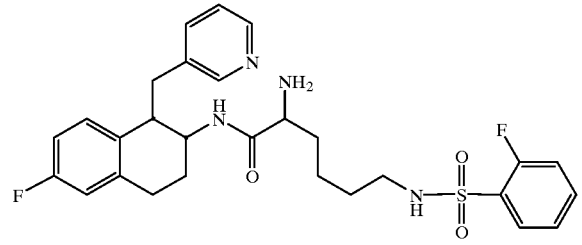
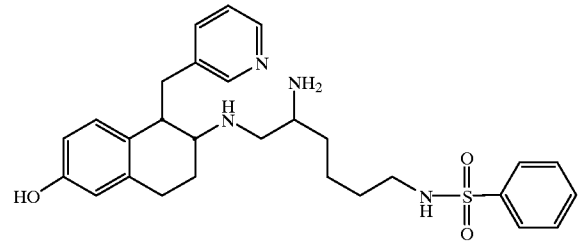
and
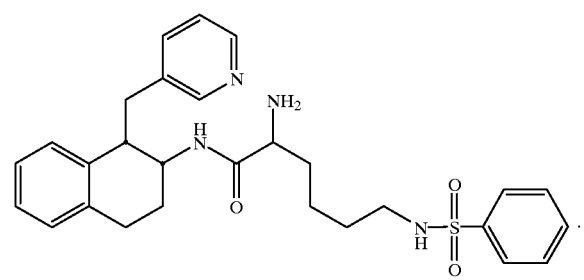
3. A compound of claim 1 selected from the group consisting of:
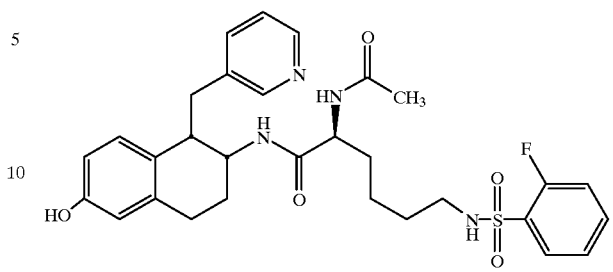
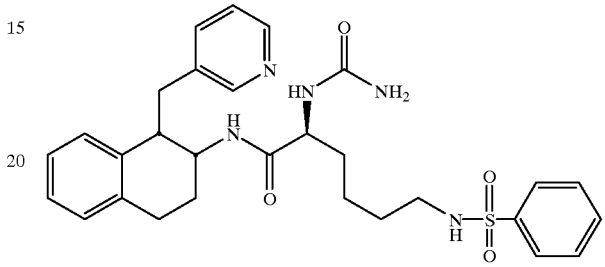
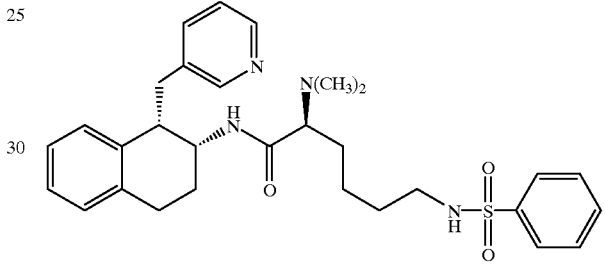
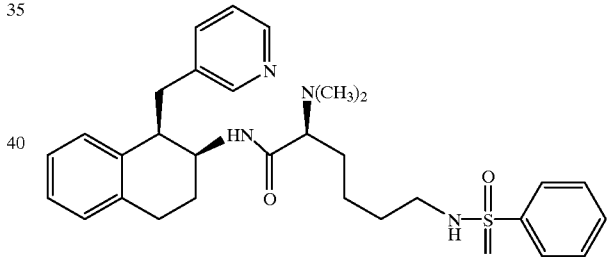
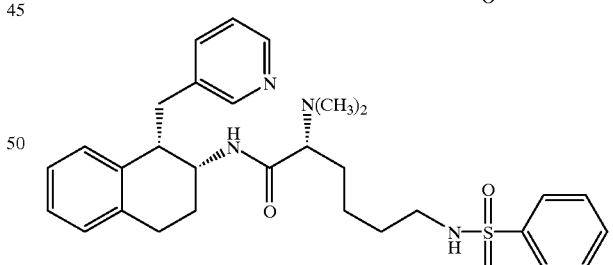
and
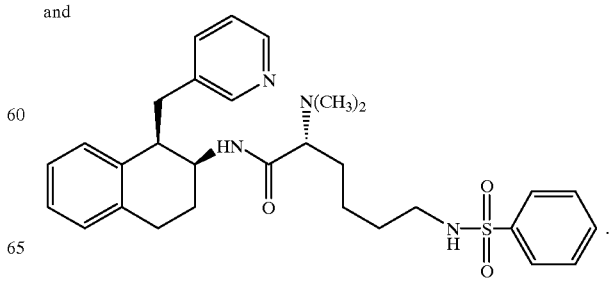

4. A compound of claim 1 selected from the group consisting of:

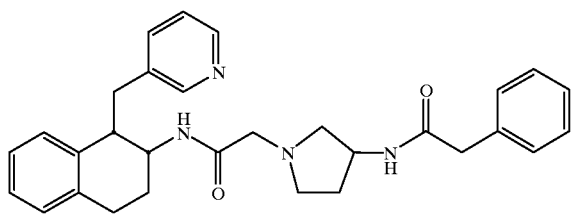

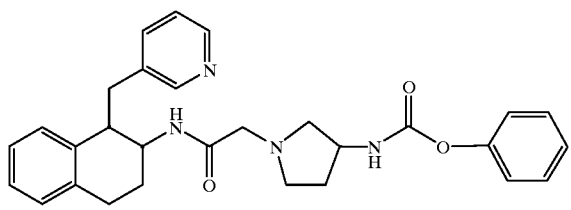

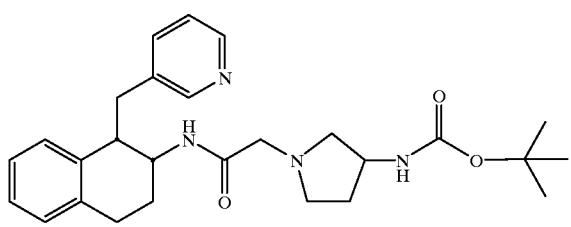

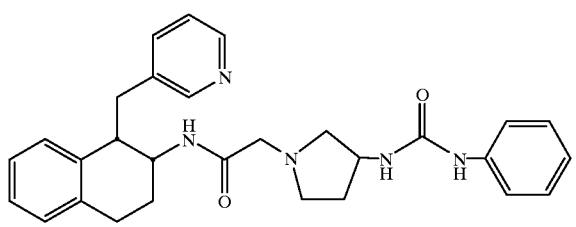

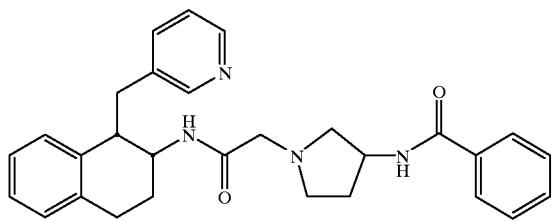

and

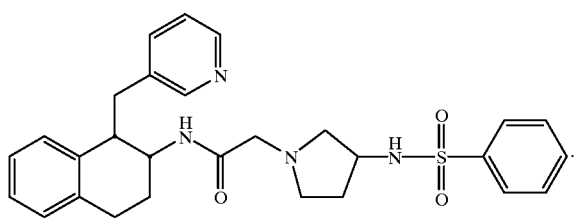

5. A compound of claim 1 selected from the group consisting of:

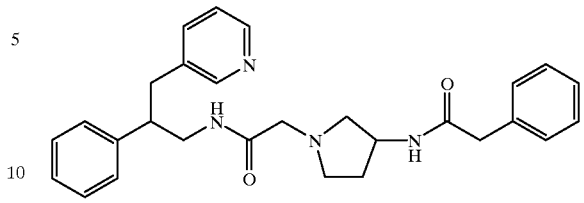

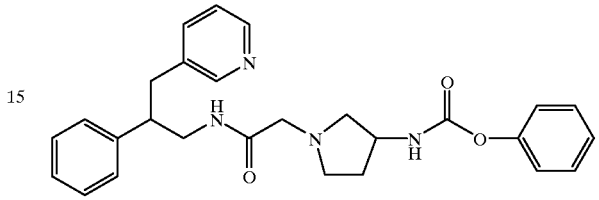

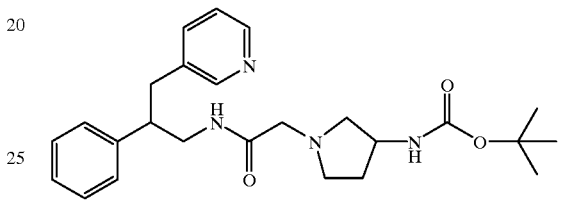

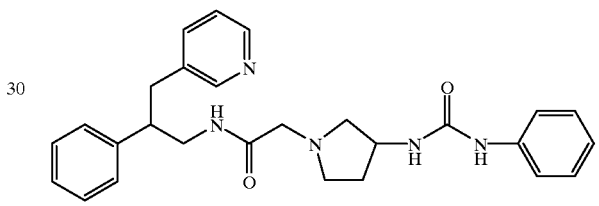

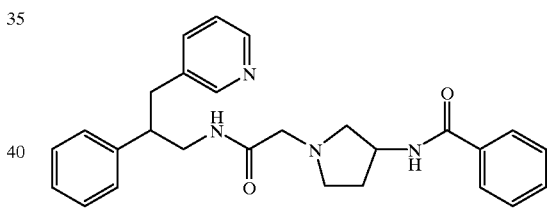

and

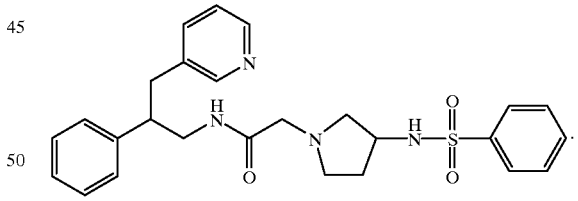

6. A compound of claim 1 selected from the group consisting of:
  2-Amino-6-[(2-fluorophenylsulfonyl)amino]-N-[cis-1,2,3,4-tetrahydro-6-methoxy-1-(3-pyridinylmethyl)-2-naphthenyl]-(2S)-hexanamide bis-hydrochloride,
  N-[5-amino-6-[[cis-1,2,3,4-tetrahydro-6-methoxy-1-(3-pyridinylmethyl)-2-naphthalenyl]amino]hexyl]-2-fluorobenzenesulfonamide tris-hydrochloride,
  N-[5-amino-6-[[cis-1,2,3,4-tetrahydro-6-hydroxy-1-(3-pyridinylmethyl)-2-naphthalenyl]amino]hexyl]-2-fluorobenzenesulfonamide tris-hydrochloride,
  (2S)-2-(Acetylamino)-6-[(2-fluorophenylsulfonyl)amino]-N-[cis-1,2,3,4-tetrahydro-6-methoxy-1-(3-pyridinylmethyl)-2-naphthenyl]hexanamide bis-hydrochloride, (2S)-2-(Acetylamino)-6-[(2-fluorophenylsulfonyl)amino]-N-[cis-1,2,3,4-tetrahydro-6-hydroxy-1-(3-pyridinylmethyl)-2-naphthenyl]hexanamide bis-hydrochloride, 3-[(Phenylsulfonyl)amino]-N-[cis-1,2,3,4-tetrahydro-6-fluoro-1-(3-pyridinylmethyl)-2-naphthalenyl]-1-pyrrolidineacetamide bis-trifluoroacetate, 4-Oxo-1-phenyl-N-[cis-1,2,3,4-tetrahydro-1-(3-pyridinylmethyl)-2-naphthalenyl]-1,3,8-triazaspiro[4.5]decane-8-acetamide bis-hydrochloride, trans-N-[2-(4-fluorophenyl)-3-(3-pyridinyl)propyl]-4-[((2-fluorophenylsulfonyl)amino)methyl]-1-cyclohexanamide hydrochloride, trans-N-[[[[[2-(4-fluorophenyl)-3-(3-pyridinyl)propyl]amino]methyl]-4-cyclohexyl]methyl]2-fluorobenzenesulfonamide bis-hydrochloride.

7. A method of treating disorders and diseases associated with NPY receptor subtype 5 comprising administering to a mammal in need of such treatment a therapeutically effective amount of a compound of claim 1.

8. A pharmaceutical composition for the treatment of diseases or disorders associated with the NPY Y5 receptor subtype comprising a therapeutically effective amount of a compound of claim 1 and a pharmaceutically acceptable carrier.

9. A pharmaceutical composition according to claim 8 for the treatment of disorders or disease states caused by eating disorders, obesity, bulimia nervosa, diabetes, memory loss, epileptic seizures, migraine, sleep disturbances, pain, sexual/reproductive disorders, depression and anxiety.

* * * * *

UNITED STATES PATENT AND TRADEMARK OFFICE
CERTIFICATE OF CORRECTION

PATENT NO. : 6,380,224 B1
DATED : April 30, 2002
INVENTOR(S) : Scott L. Dax et al.

It is certified that error appears in the above-identified patent and that said Letters Patent is hereby corrected as shown below:

Column 100,
Line 56, change "$C_{2-20}$alkenylene" to read -- $C_2$-$C_{10}$alkenylene --

Column 102,
Line 29, change "$C_{1-6}$alkyl" to read -- $C_{1-8}$alkyl --
Line 40, change "$C_{1-}$alkylcarbonyl" to read -- $C_{1-8}$alkylcarbonyl --
Line 56, change "amino$C_{4-7}$alkylene" to read -- α-amino $C_{4-7}$alkylene --
Lines 60-64 change

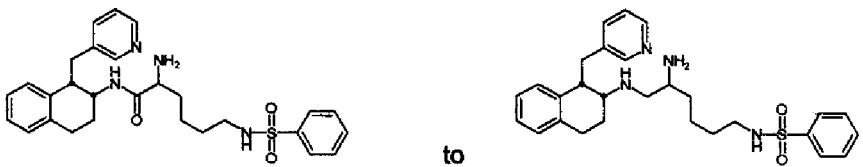

to

Signed and Sealed this

Eleventh Day of January, 2005

JON W. DUDAS
*Director of the United States Patent and Trademark Office*